US012698276B2

(12) United States Patent
Mobashery et al.

(10) Patent No.: US 12,698,276 B2
(45) Date of Patent: Aug. 4, 2026

(54) ANTIBACTERIAL PICOLINAMIDE COMPOUNDS

(71) Applicant: University of Notre Dame Du Lac, South Bend, IN (US)

(72) Inventors: Shahriar Mobashery, South Bend, IN (US); Mayland Chang, South Bend, IN (US); Enrico Speri, South Bend, IN (US)

(73) Assignee: University of Notre Dame du Lac, South Bend, IN (US)

(*) Notice: Subject to any disclaimer, the term of this patent is extended or adjusted under 35 U.S.C. 154(b) by 776 days.

(21) Appl. No.: 18/003,166

(22) PCT Filed: Jun. 28, 2021

(86) PCT No.: PCT/US2021/039381
§ 371 (c)(1),
(2) Date: Dec. 23, 2022

(87) PCT Pub. No.: WO2022/005976
PCT Pub. Date: Jan. 6, 2022

(65) Prior Publication Data

US 2023/0271950 A1 Aug. 31, 2023

Related U.S. Application Data

(60) Provisional application No. 63/045,453, filed on Jun. 29, 2020.

(51) Int. Cl.
*C07D 413/12* (2006.01)
*A61P 31/04* (2006.01)

(52) U.S. Cl.
CPC ............ *C07D 413/12* (2013.01); *A61P 31/04* (2018.01)

(58) Field of Classification Search
CPC ............................... C07D 413/12; A61P 31/04
See application file for complete search history.

(56) References Cited

U.S. PATENT DOCUMENTS

2007/0197553 A1* 8/2007 Jaeschke ................. A61P 29/02 544/333
2012/0277208 A1 11/2012 Hayakawa et al.

FOREIGN PATENT DOCUMENTS

CN 102558149 A 7/2012
CN 107903208 4/2018
EP 3892618 A1 10/2021
KR 100703598 B1 4/2007
WO 2007093542 A1 8/2007
WO 2009083553 A1 7/2009
WO 2010017179 A1 2/2010
WO 2013033068 A1 3/2013
WO 2019199496 A1 10/2019
WO WO-2020147705 A1 * 7/2020 ........... C07D 475/00

OTHER PUBLICATIONS

Chemical Abstracts STN Registry Database, record for RN 2249330-33-2, "5-(4-Methoxyphenyl)-N-(4-methyl-4H-1,2,4-triazol-3-yl)-3-pyridinecarboxamide", Entered into STN on Nov. 18, 2018. (Year: 2018).*
Bouley et al., "Discovery of Antibiotic (E)-3-(3-Carboxyphenyl)-2-(4-cyanostyryl)quinazolin-4(3H)-one," J Am Chem Soc., 137(5):1738-1741, Feb. 2015.
Carter et al., "The Role of Toxin A and Toxin B in the Virulence of Clostridium difficile," Trends Microbiol., 20(1):21-29, Jan. 2012.
International Search Report and Written Opinion of the ISA/US in PCT/US2021/039381, dated Dec. 16, 2021, 10pgs.
Speri e tal., "Discovery of a Potent Picolinamide Antibacterial Active against Clostridioides difficile," ACS Infect Dis., 6(9):2362-2368, Aug. 2020.
Speri et al., "Cinnamonitrile Adjuvants Restore Susceptibility to β-Lactams against Methicillin-Resistant *Staphylococcus aureus*," ACS Med Chem Lett., 10(8):1148-1153, Jul. 2019.
Chemical Abstracts Plus STN Registry Database, Record for AN 2018: 736424, 2018, (2018).
Extended Search Report and Written Opinion of the European Patent Office dated Jun. 20, 2024 in EP Application No. 21833830.9; 9pgs.
Speri et al., "Structure-Activity Relationship for the Picolinamide Antibacterials that Selectively Target Clostridioides difficile," ACS Med. Chem. Lett., 12, 991-995, May 2021.
Speri et al., "Supporting Information for Structure-Activity Relationship for the Picolinamide Antibacterials that Selectively Target Clostridioides difficile," ACS Med. Chem. Lett., S1-S78, May 2021.

* cited by examiner

*Primary Examiner* — Clinton A Brooks
(74) *Attorney, Agent, or Firm* — Haukaas Fortius PLLC; Michael H. Haukaas; Raymond F. Horvath

(57) ABSTRACT

Here we report the discovery of 2-(4-(3-(trifluoromethoxy) phenoxy)picolinamido)benzo[d]oxazole-5-carboxylate as an antibacterial with potent and selective activity against *C. difficile*. Its $MIC_{50}$ and $MIC_{90}$ values, documented across 101 strains of *C. difficile*, are 0.12 and 0.25 μg/mL, respectively. The compound is effective against *C. difficile* both at the logarithmic (vegetative) and stationary phases of growth. It targets cell-wall biosynthesis, as assessed both by macromolecular biosynthesis assays and by scanning-electron microscopy. Animals infected with a lethal dose of *C. difficile* and treated with compound 1 had better survival compared to treatment with vancomycin, which is the front-line antibiotic used for severe recurrent *C. difficile* infection.

19 Claims, 3 Drawing Sheets

ANTIBACTERIAL PICOLINAMIDE COMPOUNDS

RELATED APPLICATIONS

This application is a National Stage filing under 35 U.S.C. § 371 of International Application No. PCT/US2021/039381 filed Jun. 28, 2021, which claims the benefit of U.S. Provisional Patent Application No. 63/045,453, filed Jun. 29, 2020, which applications are incorporated herein by reference.

GOVERNMENT SUPPORT

This invention was made with government support under grants AI104987 and AI116548 awarded by the National Institutes of Health. The government has certain rights in the invention.

BACKGROUND OF THE INVENTION

*Clostridioides difficile* is a Gram-positive, anaerobic, spore-forming bacterium. It is currently designated as an urgent health problem causing life-threatening diarrhea. An estimated 223,900 hospitalizations with *C. difficile* infection (CDI) occurred in the United States in 2017, with approximately 12,800 deaths. One-third of the patients experience recurring infection leading to increased morbidity and mortality. Furthermore, *C. difficile* produces spores that are resistant to antibiotics and can remain dormant for many months and years. The disruption of the normal gut flora due to use of broad-spectrum antibiotics facilitates the colonization and proliferation of *C. difficile* in the large intestine. Treatments for CDI include metronidazole (MTZ), vancomycin (VAN), and fidaxomicin (FDX). However, MTZ is toxic and it also kills beneficial gut bacteria. Fidaxomicin (FDX) is a narrow-spectrum bactericidal antibiotic effective against *C. difficile*, however its use is limited due to its high cost and decreased efficacy against the highly virulent BI/NAP1/027 strain. Fecal microbiota transplant has been explored as CDI treatment. However, it is not standardized, and it has safety concerns such as the risk of transferring pathogenic organisms, or autoimmune or metabolic disorders from donors to recipients. Several antimicrobial agents have been reported recently against *C. difficile*. Major challenges that have not been overcome for these agents are disruption of normal gut flora, the development of resistance, and a failure to reduce recurrence.

Accordingly, there is a need for better treatments for *C. difficile* infections that are safe and effective.

SUMMARY

Herein we disclose the discovery of potent picolinamide antibacterials that are active against *Clostridioides difficile*. Accordingly, this disclosure provides a compound of Formula I.

(I)

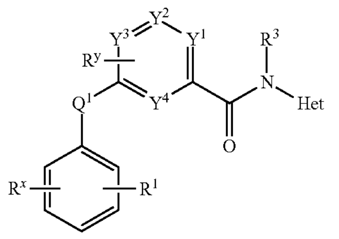

or a salt thereof, wherein

Het is

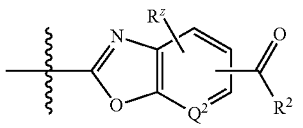

or

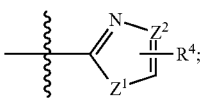

$Q^1$ is O, absent, S, or $NR^w$;

$Q^2$ is CH or N;

each $R^w$ is independently H, $-(C_1\text{-}C_6)$alkyl, or a protecting group;

$R^x$, $R^y$, and $R^z$ are each independently H, halo, OH, CN, $CO_2H$, $NO_2$, $-(C_1\text{-}C_6)$alkyl, $-CO_2(C_1\text{-}C_6)$alkyl, $-O(C_1\text{-}C_6)$alkyl, or $-OC(=O)(C_1\text{-}C_6)$alkyl;

$R^1$ is $OR^a$, $SR^a$, halo, CN, $NO_2$, $-(C_1\text{-}C_6)$alkyl, $NR^w$, or heterocyclyl, wherein each $R^a$ is independently $CF_3$, $-(C_1\text{-}C_6)$alkyl, $-C(=O)(C_1\text{-}C_6)$alkyl, or H;

$R^2$ is OH, $-O(C_1\text{-}C_6)$alkyl, $-O(C_3\text{-}C_6)$cycloalkyl, or $-CCH$;

$R^3$ is H, $-(C_1\text{-}C_6)$alkyl or $-(C_3\text{-}C_6)$cycloalkyl;

$R^4$ is H, $-(C_1\text{-}C_6)$alkyl, or $-C(=O)R^5$ wherein $R^5$ is OH, $N(CH_3)_2$, $-O(C_1\text{-}C_6)$alkyl, or heterocyclyl;

$Y^1$, $Y^2$, $Y^3$, and $Y^4$ are each independently CH or N wherein at least one of $Y^1$ to $Y^4$ is N;

$Z^1$ is O, N, S, or CH; and $Z^2$ is CH, O, or N;

wherein each $(C_1\text{-}C_6)$alkyl moiety is independently saturated or unsaturated and optionally substituted.

This disclosure also provides a method for treating a bacterial infection comprising administering to a subject in need thereof an effective antibacterial amount of a compound or composition disclosed above wherein the bacterial infection is thereby treated.

The invention provides novel compounds of Formula I and Formula II, intermediates for the synthesis of compounds of Formula I and Formula II, as well as methods of preparing compounds of Formula I and II. The invention also provides compounds of Formula I and II that are useful as intermediates for the synthesis of other useful compounds. The invention provides for the use of compounds of Formula I and Formula II for the manufacture of medicaments useful for the treatment of bacterial infections in a mammal, such as a human.

The invention provides for the use of the compositions described herein for use in medical therapy. The medical therapy can be treating a bacterial infection. The invention also provides for the use of a composition as described herein for the manufacture of a medicament to treat a disease in a mammal, for example, a Gram-positive bacterial infection in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
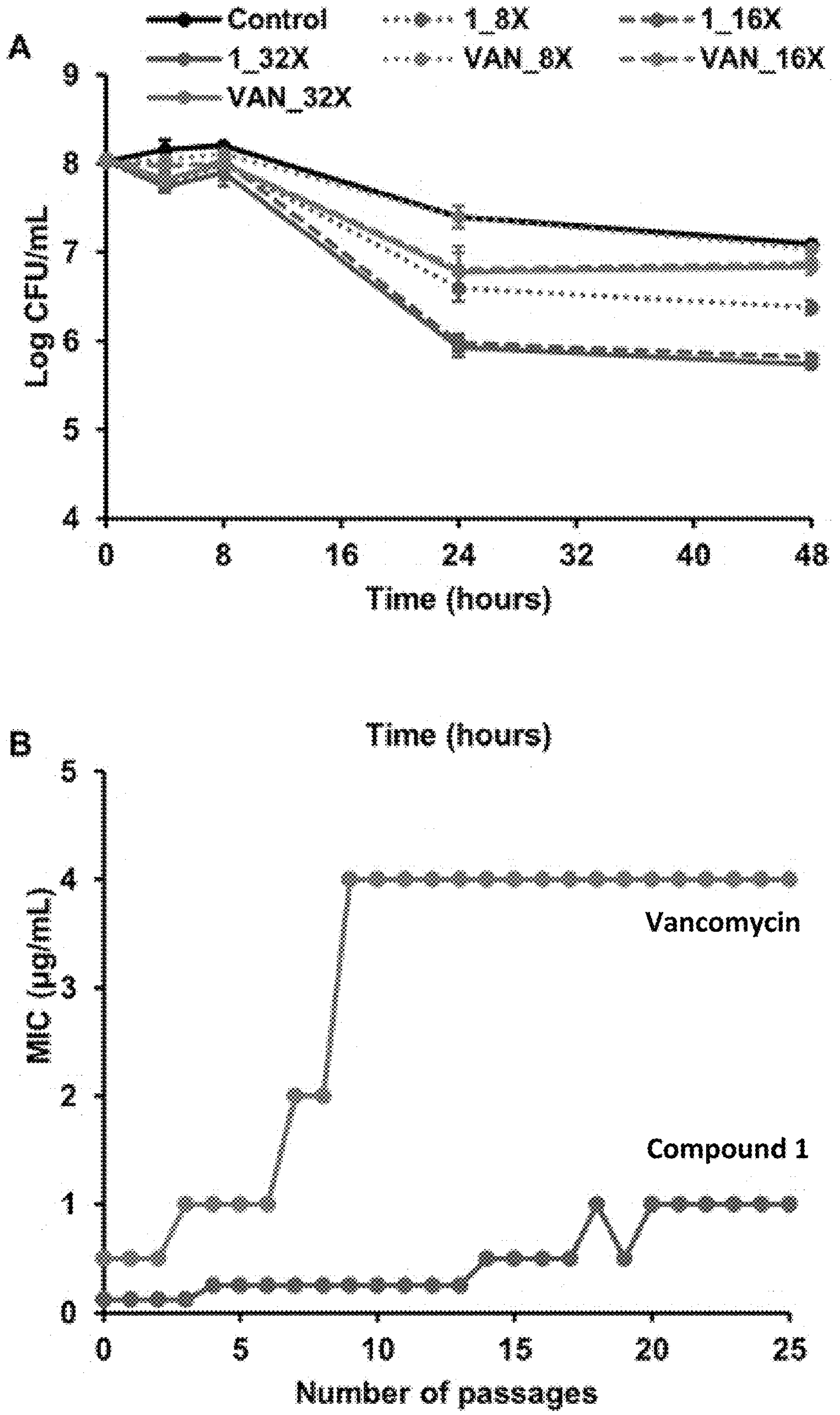
FIG. 1. Anti-*C. difficile* activity of compound 1. (A) Compound 1 reduces stationary-phase *C. difficile* growth better than VAN in the time-kill assay. (B) Serial passage of *C. difficile* ATCC 43255 in the presence of sub-MIC concentrations of 1 and of VAN.

We report the discovery of 2-(4-(3-(trifluoromethoxy)-phenoxy)picolinamido)benzo[d]oxazole-5-carboxylate (compound 1). This compound exhibits potent antibacterial activity against *C. difficile* without significant activity against other major gut bacteria. Compound 1 was identified in the course of research on the cinnamonitrile potentiators of β-lactam antibiotics against methicillin-resistant *Staphylococcus aureus* (MRSA). While the cinnamonitrile potentiators do not exhibit antibacterial activity, insertion of an oxazole moiety into this structural template imparted antibacterial activity. Further structural elaboration of the picolinamide moiety significantly altered the structural template from the cinnamonitriles, leading to compound 1. Compound 1 is a potent and uniquely selective anti-*C. difficile* antibacterial.

(1)

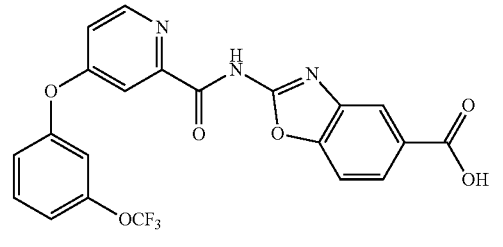

or a salt thereof.

Additional information and data supporting the invention can be found in the following publication by the inventors: *ACS Infect. Dis.* 2020, 6, 2362-2368 and its Supporting Information, which is incorporated herein by reference in its entity.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic.

Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of +5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated.

Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of a compound of the disclosure into a subject by a method or route that results in at least partial localization of the compound to a desired site. The compound can be administered by any appropriate route that results in delivery to a desired location in the subject.

The compound and compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value.

The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983); for heterocyclic synthesis see Hermanson, Greg T., Bioconjugate Techniques, Third Edition, Academic Press, 2013.

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below or otherwise described herein. The alkyl can also be optionally partially or fully unsaturated. As such, the recitation of an alkyl group can include an alkenyl group or an alkynyl group. The alkyl can be a monovalent hydrocarbon radical, as described and exemplified above, or it can be a divalent hydrocarbon radical (i.e., an alkylene).

An alkylene is an alkyl group having two free valences at a carbon atom or two different carbon atoms of a carbon chain. Similarly, alkenylene and alkynylene are respectively an alkene and an alkyne having two free valences at two different carbon atoms.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" or "heterocyclyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered.

Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted with a substituent described below.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms, wherein the ring skeleton comprises a 5-membered ring, a 6-membered ring, two 5-membered rings, two 6-membered rings, or a 5-membered ring fused to a 6-membered ring. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

As used herein, the term "substituted" or "substituent" is intended to indicate that one or more (for example, in various embodiments, 1-10; in other embodiments, 1-6; in some embodiments 1, 2, 3, 4, or 5; in certain embodiments, 1, 2, or 3; and in other embodiments, 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, haloalkyl, hydroxyalkyl, aryl, heteroaryl, heterocyclyl, cycloalkyl, alkanoyl, alkoxycarbonyl, amino, alkylamino, dialkylamino, carboxyalkyl, alkylthio, alkylsulfinyl, and alkylsulfonyl. Substituents of the indicated groups can be those recited in a specific list of substituents described herein, or as one of skill in the art would recognize, can be one or more substituents selected from alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Suitable substituents of indicated groups can be bonded to a substituted carbon atom include F, Cl, Br, I, OR', OC(O)N(R')2, CN, CF3, OCF3, R', O, S, C(O), S(O), methylenedioxy, ethylenedioxy, N(R')2, SR', SOR', SO2R', SO2N(R')2, SO3R', C(O)R', C(O)C(O)R', C(O)CH2C(O)R', C(S)R', C(O)OR', OC(O)R', C(O)N(R')2, OC(O)N(R')2, C(S)N(R')2, (CH2)0-2NHC(O)R', N(R')N(R')C(O)R', N(R')N(R')C(O)OR', N(R')N(R')CON(R')2, N(R')SO2R', N(R')SO2N(R')2, N(R')C(O)OR', N(R')C(O)R', N(R')C(S)R', N(R')C(O)N(R')2, N(R')C(S)N(R')2, N(COR')COR', N(OR')R', C(=NH)N(R')2, C(O)N(OR')R', or C(=NOR')R' wherein R' can be hydrogen or a carbon-based moiety (e.g., ($C_1$-$C_6$)alkyl), and wherein the carbon-based moiety can itself be further substituted. When a substituent is monovalent, such as, for example, F or Cl, it is bonded to the atom it is substituting by a single bond. When a substituent is divalent, such as O, it is bonded to the atom it is substituting by a double bond; for example, a carbon atom substituted with O forms a carbonyl group, C=O.

Embodiments of the Technology

This disclosure provides a compound of Formula I:

(I)

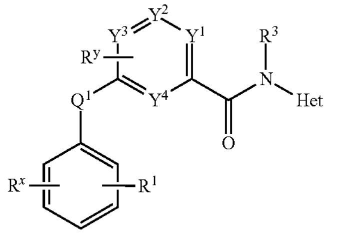

or a salt thereof, wherein

Het is

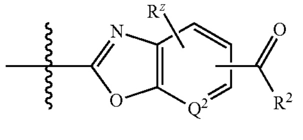

or

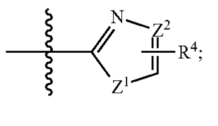

$Q^1$ is O, absent, S, or $NR^w$;

$Q^2$ is CH or N;

each $R^w$ is independently H, —($C_1$-$C_6$)alkyl, or a protecting group;

$R^x$, $R^y$, and $R^z$ are each independently H, halo, OH, CN, $CO_2H$, $NO_2$, —($C_1$-$C_6$)alkyl, —$CO_2$($C_1$-$C_6$)alkyl, —O($C_1$-$C_6$)alkyl, or —OC(=O)($C_1$-$C_6$)alkyl;

$R^1$ is $OR^a$, $SR^a$, halo, CN, $NO_2$, —($C_1$-$C_6$)alkyl, $NR^w$, or heterocyclyl, wherein each $R^a$ is independently $CF_3$, —($C_1$-$C_6$)alkyl, —C(=O)($C_1$-$C_6$)alkyl, or H;

$R^2$ is OH, —O($C_1$-$C_6$)alkyl, —O($C_3$-$C_6$)cycloalkyl, or —CCH;

$R^3$ is H, —($C_1$-$C_6$)alkyl or —($C_3$-$C_6$)cycloalkyl;

$R^4$ is H, —($C_1$-$C_6$)alkyl, or —C(=O)$R^5$ wherein $R^5$ is OH, $N(CH_3)_2$, —O($C_1$-$C_6$)alkyl, or heterocyclyl;

$Y^1$, $Y^2$, $Y^3$, and $Y^4$ are each independently CH or N wherein at least one of $Y^1$ to $Y^4$ is N;

$Z^1$ is O, N, S, or CH; and $Z^2$ is CH, O, or N;

wherein each ($C_1$-$C_6$)alkyl moiety is independently saturated or unsaturated and optionally substituted.

In various embodiments, Het is

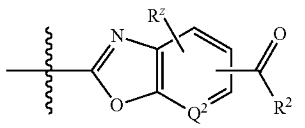

In various embodiments, $Q^2$ is CH. In various embodiments, $R^x$, $R^y$, and $R^z$ are H. In various embodiments, $Y^1$ is N, and $Y^2$, $Y^3$, and $Y^4$ are CH. In various embodiments, $R^1$ is $OR^a$. In various embodiments, $R^1$ and $R^x$ are both halo. In various embodiments, $R^y$ is halo. In various embodiments, halo is fluoro. In various embodiments, $R^z$ is H. In various embodiments, the heterocycle represented by $Y^1$ to $Y^4$ is a pyridyl, pyridazinyl, pyrimidinyl, or pyrazinyl.

In various embodiments, Het is the heterocycle represented by the 5-membered ring. In various embodiments, $Q^1$ is O. Het is an oxazolyl, isoxazolyl, pyrazolyl, oxadiazolyl, imidazolyl, oxathiazolyl, or triazolyl. In various embodiments, at least one of $Z^1$ or $Z^2$ is O, S, or N.

In another embodiment, the compound of Formula I is represented by Formula II:

(II)

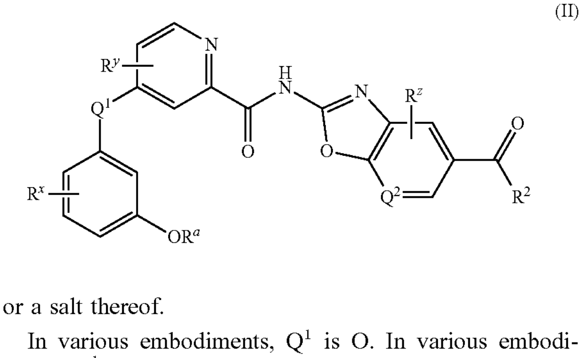

or a salt thereof.

In various embodiments, $Q^1$ is O. In various embodiments, $Q^1$ is absent. In various embodiments, $R^a$ is $CF_3$. In various embodiments, $R^2$ is OH. In some embodiments, the compound is 2-(4-(3-(trifluoromethoxy) phenoxy) picolinamido)benzo[d]oxazole-5-carboxylic acid (1):

(1)

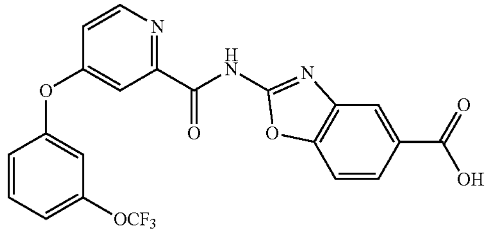

or a salt thereof.

Also, this disclosure provides a pharmaceutical composition comprising a compound disclosed herein and a pharmaceutically acceptable diluent, carrier, or excipient.

In various embodiments of the composition, the compound is 2-(4-(3-(trifluoromethoxy) phenoxy)picolinamido) benzo[d]oxazole-5-carboxylic acid (1).

Additionally, this disclosure provides a method for treating a bacterial infection comprising administering to a subject in need thereof an effective antibacterial amount of a compound or composition disclosed herein, wherein the bacterial infection is thereby treated.

In some embodiments, the bacterial infection is a *Clostridioides difficile* (*C. difficile*) infection. In various embodiments, the compound selectively inhibits the growth or proliferation of *C. difficile*. In various embodiments, a minimum concentration to inhibit the growth or proliferation of 50% (or 90%) of *C. difficile* ($MIC_{50}$ or $MIC_{90}$) is about 1 μg/mL or less.

In various embodiments, The $MIC_{50}$ or $MIC_{90}$ is about 0.01 μg/mL to about 10 μg/mL, about 0.1 μg/mL, about 0.2 μg/mL, about 0.3 μg/mL, about 0.4 μg/mL, about 0.5 μg/mL, about 0.6 μg/mL, about 0.7 μg/mL, about 0.8 μg/mL, about 0.9 μg/mL, about 1.5 μg/mL, about 2 μg/mL, about 3 g/mL, about 4 μg/mL, or about 5 μg/mL.

In various embodiments, an effective antibacterial amount of the compound administered as a single dose (or the total daily dose) is about 50 mg/kg or less. In various embodiments, an individual; dose or total daily dose is about 100 mg/kg or less, about 90 mg/kg, about 80 mg/kg, about 70 mg/kg, about 60 mg/kg, about 50 mg/kg, about 40 mg/kg, about 30 mg/kg, about 25 mg/kg, about 20 mg/kg, about 15 mg/kg, about 10 mg/kg, about 9 mg/kg, about 8 mg/kg, about 7 mg/kg, about 6 mg/kg, about 5 mg/kg, about 4 mg/kg, about 3 mg/kg, about 2 mg/kg, or about 1 mg/kg. In various embodiments, the dose is administered once per day, twice per day or three times per day.

In various embodiments of the method, the compound is 2-(4-(3-(trifluoromethoxy) phenoxy)picolinamido)benzo[d] oxazole-5-carboxylic acid (1). In various embodiments, the compound inhibits peptidoglycan biosynthesis.

Results and Discussion

Compound 1 was synthesized by the eight-step convergent synthesis shown in Scheme 1. 3-(Trifluoromethoxy) phenol (2) was allowed to react with 4-chloropicolinonitrile in the presence of potassium carbonate, followed by conversion of the nitrile in 3 to the carboxylic acid (4). Separately, we synthesized methyl 2-aminobenzo[d]oxazole-5-carboxylate (5, Scheme 1B). Reaction of cyanogen bromide (8) with imidazole produced di(1H-imidazol-1-yl)methanimine (9). Ring-closing double-nucleophilic attack of methyl 3-amino-4-hydroxybenzoate on 9 gave the desired intermediate 5. Coupling of 5 with 4 in the presence of propylphosphonic anhydride ($T_3P$®) gave 6. Saponification of the ester moiety in 6 with sodium hydroxide and subsequent work up gave the carboxylic acid 7. The sodium salt of 1 was obtained by reaction of 7 with aqueous sodium bicarbonate.

Scheme 1. Synthesis of compounds 1 and 5.

A

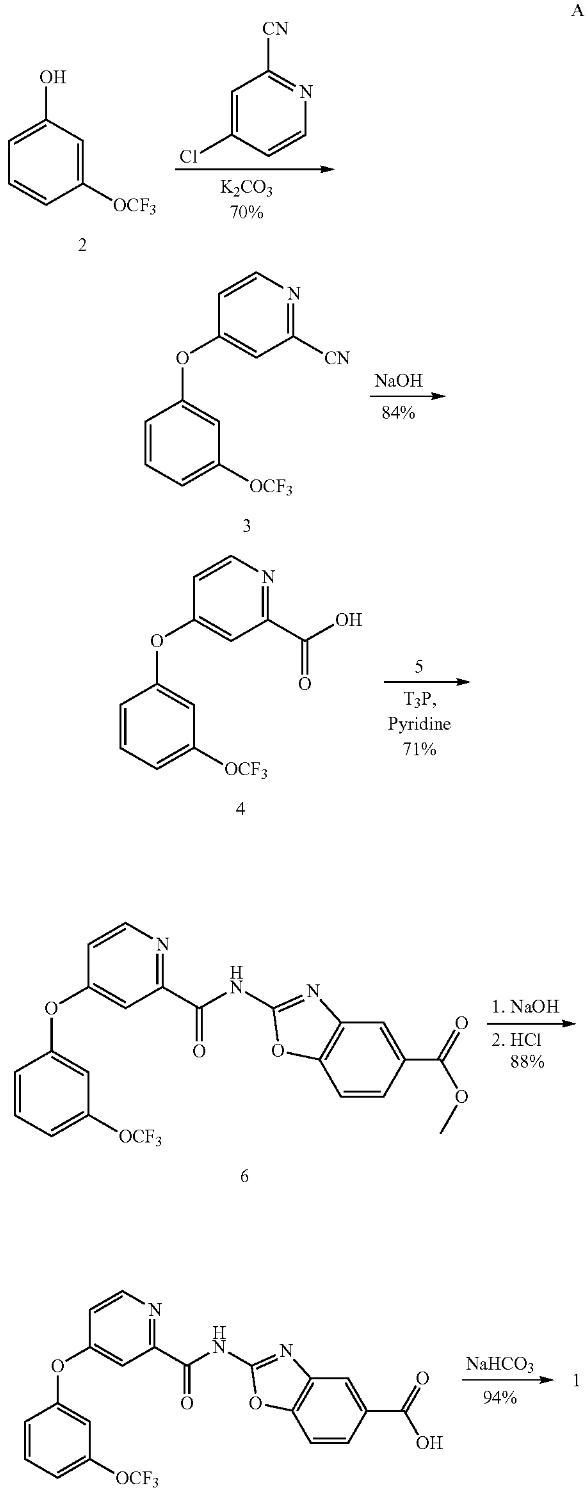

2

3

4

6

7

-continued

B

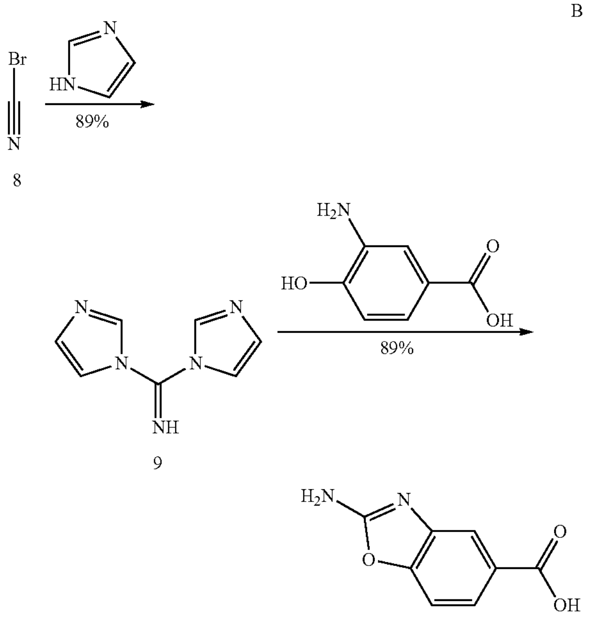

8

9

5

Compound 1 was evaluated against *C. difficile* ATCC 43255, a strain that produces toxins A (Ted A) and B (TedB), both instigators for bad outcome in CDI. The minimum inhibitory concentration (MIC) for 1 is 0.125 μg/mL. This value is 2-fold higher than FDX, and 4-fold and 2-fold lower than VAN and MTZ, respectively (Table 1). The activity of compound 1 was evaluated against 101 *C. difficile* strains, including both clinical and laboratory strains, and VAN-, MTZ-, and FDX-resistant strains (Table 9). The $MIC_{50}$ and $MIC_{90}$ values (MIC for 50% or 90% of all the strains, respectively) are excellent, at 0.12 and 0.25 μg/mL, respectively. As assessed by these MIC values, compound 1 has similar potency as FDX, but better potency than the first-line antibiotics VAN and MTZ. The minimum bactericidal concentration (MBC) for 1 is 4 μg/mL, or 64-fold higher than its MIC. Hence (by definition) 1 is bacteriostatic.

TABLE 1

MIC values in μg/mL for compound 1, VAN, MNZ, and FDX against *C. difficile*, MRSA, and major gut bacteria.

| Bacterial Strain | 1 | VAN | MTZ | FDX |
|---|---|---|---|---|
| *C. difficile* ATCC43255[a] | 0.125 | 0.5 | 0.25 | 0.06 |
| *C. difficile* BAA-1870[b] | 0.125 | 2 | 0.5 | 0.25 |
| *C. difficile* 26675[c] | 0.25 | 1 | 4 | 4 |
| *C. difficile* 23828[d] | 0.25 | 2 | 0.5 | >8 |
| *C. difficile* 23691[e] | 0.125 | 4 | 0.5 | 4 |
| $MIC_{50}$ (101 strains) | 0.12 | 0.5 | 0.5 | 0.06 |
| $MIC_{90}$ (101 strains) | 0.25 | 2 | 1 | 0.25 |
| *S. aureus* ATCC29213 | 64 | 1 | >128 | 8 |
| *E. faecium* NCTC7171 | >128 | 0.5 | >128 | 2 |
| MRSA NRS70 | 16 | 2 | >128 | 8 |
| MRSA NRS119 | 16 | 2 | >128 | 2 |
| *Bacteroides fragilis*[f] | 2 | 16 | 0.5 | >32 |
| *Bifidobacterium longum*[g] | 16 | 0.25 | 0.5 | <0.01 |
| *Corynebacterium* spp.[h] | 8 | 0.25 | >32 | <0.06 |
| *Fusobacterium nucleatum*[i] | 4 | 0.25 | 2 | <0.06 |
| *Lactobacillus reuteri*[j] | 4 | >32 | >32 | >32 |
| *Lactobacillus gasseri*[k] | >16 | 1 | >32 | 2 |
| *Veillonella* sp. HM-49[l] | 16 | >32 | 2 | 8 |

TABLE 1-continued

MIC values in μg/mL for compound 1, VAN, MNZ, and FDX against *C. difficile*, MRSA, and major gut bacteria.

| Bacterial Strain | 1 | VAN | MTZ | FDX |
|---|---|---|---|---|
| *Eubacterium* sp.[m] | 8 | 2 | 1 | 16 |
| Fecal microbiota preparation[n] | >128 | >128 | >128 | >128 |

VAN: vancomycin.
MTZ: metronidazole.
FDX: fidaxomicin.
[a]isolated from abdominal wound, TcdA+, TcdB+;
[b]NAP1, BI 8, ribotype 27, toxinotype IIIb, TcdA+, TcdB+, CDT+ (binary toxin);
[c]clinical isolate resistant to MTZ;
[d]clinical isolate resistant to FDX;
[e]clinical isolate resistant to VAN;
[f]Strain HM-709, Gram-negative, anaerobic bacterium that is commensal and critical to host immunity; a minor component of the human gut microflora (<1%);
[g]Strain HM-846, anaerobic, Gram-positive bacterium commonly found in the normal human intestinal microflora isolated from human feces, non-sporulating,
[h]Strain HM-784, Gram-positive, aerobic or facultatively anaerobic bacterium that occurs in the mucosa and normal skin flora of humans and animals;
[i]Strain HM-992, anaerobic, non-sporulating, Gram-negative bacterium commonly found in the gastrointestinal tract;
[j]Strain HM-102, Gram-positive, anaerobic bacteria commonly found in the normal human gastrointestinal tract, commonly used as a probiotic to maintain balance of gut microbial flora;
[k]Strain HM-644, Gram-positive, facultative, anaerobe bacterium commonly found in the normal human gastrointestinal tract, commonly use in yogurt production as a probiotic to suppress *Helicobacter pylori* infections;
[l]Gram-negative, non-sporulating bacterium commonly found in the intestinal tract of humans and animals;
[m]Strain HM-178, anaerobic, non-sporulating, Gram-positive bacterium commonly found in the gastrointestinal flora of humans and animals.
[n]Fecal microbiota preparation obtained from OpenBiome tested at 1000-fold dilution.

Compound 1 is poorly active against MRSA (128-fold lower activity), in contrast to VAN and FDX (Table 1). As broad-spectrum antibiotics can disrupt the normal gut flora allowing for *C. difficile* to become established, we evaluated the selectivity of compound 1 toward *C. difficile* ATCC 43255 compared to major gut bacterial flora. Compound 1 was generally more selective (16- to 1000-fold, Table 1) than VAN (0.5- to 64-fold), MTZ (2- to 512-fold), and FDX (0.25- to 512-fold).

The in vitro cytotoxicity of 1 was evaluated by XTT (2,3-bis-(2-methoxy-4-nitro-5-sulfophenyl)-2H-carboxanilide) assay using HeLa cells. The $IC_{50}$ value of 179±4 μg/mL was >700-fold above its $MIC_{90}$. As antibiotics for the treatment of CDI need to be poorly absorbed so as to achieve high concentrations in the gut, we determined the levels of compound 1 in plasma and feces after 20 mg/kg single oral administration to mice. Concentrations of 1 were non-quantifiable in plasma. The levels in feces were 13 μg/g (equivalent to 13 μg/mL, assuming a density of 1 g/mL), >100-fold higher than the MIC for *C. difficile* ATCC 43255, indicating that desirable high concentrations for effective antibacterial activity are reached in the gut.

Antibacterial activity typically manifests in the logarithmic phase of the bacterial growth, and not in the slow-growing cells of the stationary phase of growth. We investigated the effect of compound 1 on stationary-phase *C. difficile* using time-kill assays. Compound 1 reduced *C. difficile* stationary-phase growth by 2 $\log_{10}$, whereas VAN decreased it by a mere 1 $\log_{10}$ (FIG. 1A). Another attribute of antibiotics is selection for resistance. We investigated resistance development against compound 1 by serial passage evaluation of MIC values, and in comparison to VAN. The MIC values for compound 1 increased from 0.125 to 1 μg/mL whereas those for VAN changed from 0.5 to 4 μg/mL (FIG. 1B). In both cases the increase was 8-fold. However, the MIC values for compound 1 were 4-fold lower.

Figure 2:
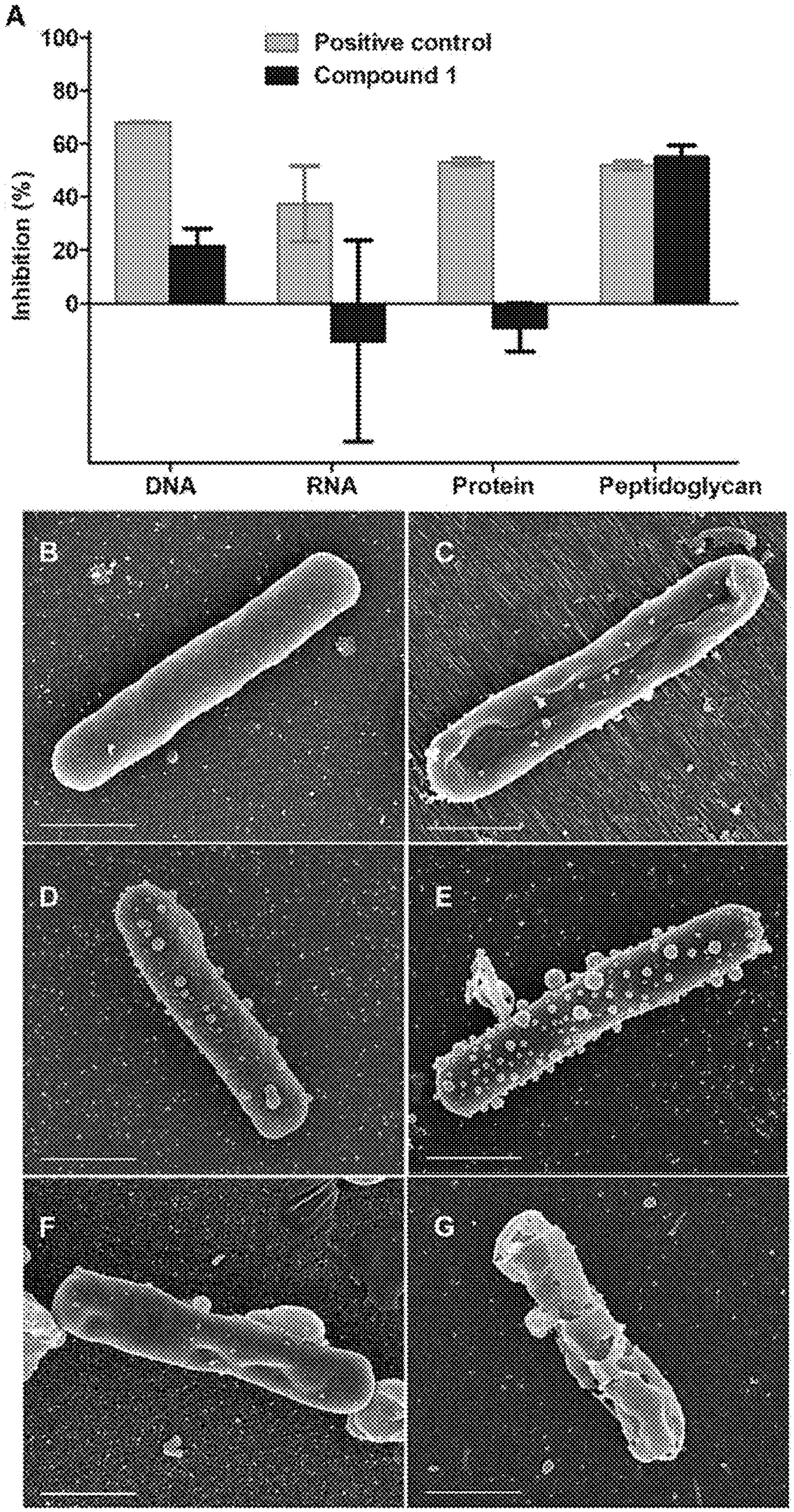
FIG. 2. Mechanism of action of compound 1. (A) Macromolecular biosynthesis assays: Compound 1 was incubated with *C. difficile* ATCC43255 at 0.5×MIC. The positive controls are ciprofloxacin (DNA, MIC 8 μg/mL), rifaximin (RNA, MIC 0.03 μg/mL), linezolid (protein, MIC 2 μg/mL), and oxacillin (peptidoglycan, MIC 8 μg/mL). The incubation time was 60 min for DNA, 120 min for peptidoglycan synthesis and RNA, and 180 min for protein synthesis. (B-G) Imaging of *C. difficile* ATCC42355 vegetative cells (logarithmic growth) by scanning electron microscopy. (B) *C. difficile* ATCC43255 untreated control, (C) VAN-treated at 4×MIC; compound 1 treated at (D) 4×MIC, (E) 8×MIC, (F) 16×MIC, (G) 32×MIC.

The mechanism of action of 1 was investigated using macromolecular synthesis assays. These assays measure the incorporation of radioactive precursors ([2,8-$^3$H]-adenine, [5,6-$^3$H]-uridine, 1-[3,4,5-$^3$H(N)]-leucine, and N-acetyl-d-[6-$^3$H]glucosamine) respectively into DNA, RNA, protein, and peptidoglycan. As shown in FIG. 2A, compound 1 inhibits cell-wall peptidoglycan biosynthesis (55±4%). This value was similar to the value (51±1%) for *C. difficile* exposed to the cell-wall-active antibiotic oxacillin, which served as a positive control. Minimal levels of inhibition were observed for DNA, RNA, and protein synthesis. We confirmed that compound 1 targets peptidoglycan biosynthesis by imaging *C. difficile* bacteria by scanning-electron microscopy (FIG. 2B-G). This analysis visualizes the cell wall as the outermost layer of the cell envelope of Gram-positive bacteria such as *C. difficile*. The surface of untreated *C. difficile* ATCC43255 (FIG. 2B) is unperturbed, but is altered upon exposure to VAN (FIG. 2C). Upon exposure to 1 (FIG. 2D shows *C. difficile* at 4×MIC; FIGS. 2E-2G show the effects of increased levels of 1) bleb formation on the surface was evident (FIGS. 2D and 2E). At higher concentrations of 1 decisive damage to the cell wall (FIG. 2F) culminates in the destruction of the bacterium (FIG. 2G).

Figure 3:
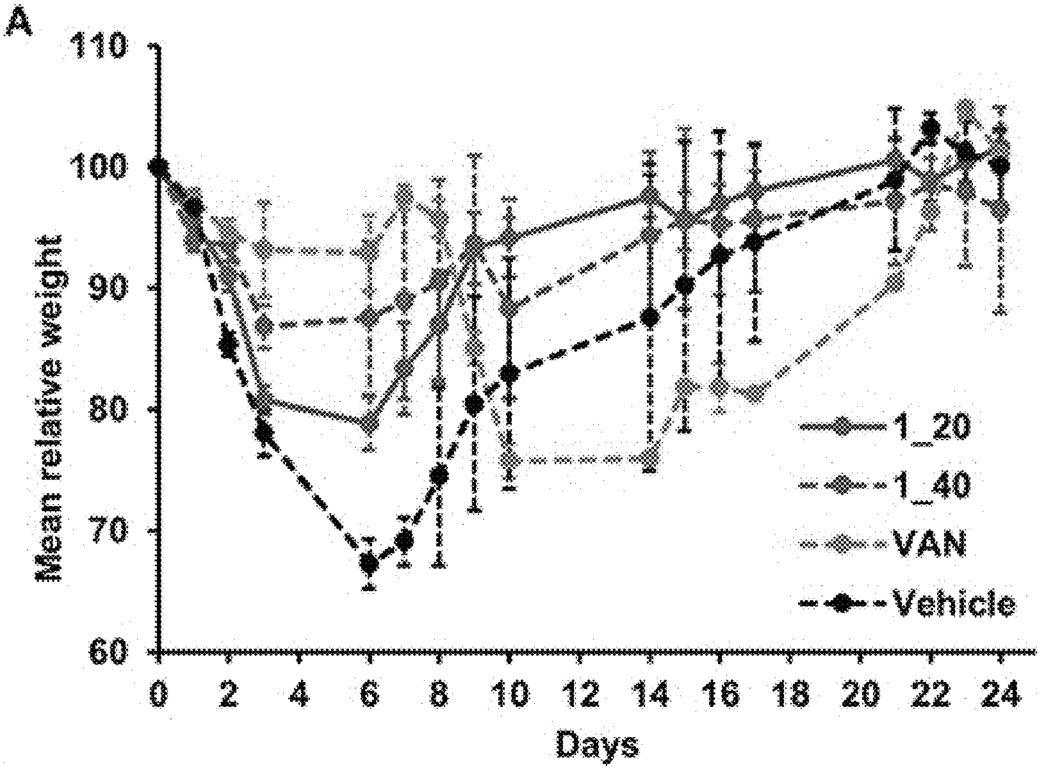
FIG. 3. Efficacy of compound 1 in a mouse model of recurrent CDI. (A) Body weights (n=10 mice per group); recurrence of infection is observed in the VAN-treated group on days 10 to 15. (B) Survival plot, n=10 mice per group.
Figure 3:
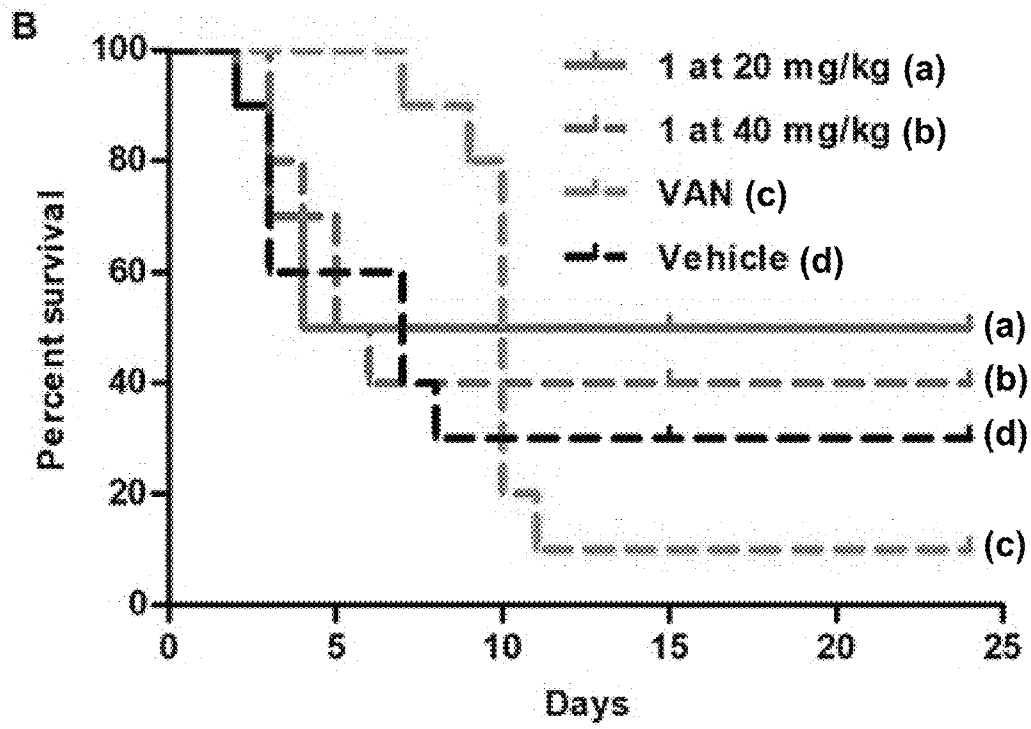

Next, compound 1 was evaluated in a mouse model of recurrent CDI. This model uses an antibiotic cocktail containing kanamycin, gentamicin, colistin, MTZ, VAN, and clindamycin to perturb the gut microbiota, followed by infection with *C. difficile* ATCC 43255. Oral dosing with compound 1 was once a day for 5 days, with VAN as positive control and vehicle as negative control. This model results in recurrence of infection in VAN-treated mice, as seen by loss of body weight on days 10-15 (FIG. 3A). At the end of the study animals receiving compound 1 showed similar survival of the mice (FIG. 3B) compared to VAN.

Notwithstanding the availability of MTZ, VAN, and FDX for treatment of CDI, recurrence of infection takes place in 25% of patients treated with these antibiotics. Over 12,000 annual deaths from CDI occur in the US alone, leading to designation of these infections as an urgent health problem. Compound 1 is a potent anti-*C. difficile* agent with in vivo activity that holds promise in addressing this clinical need.

Structure-Activity Relationship for the Picolinamide Antibacterials that Selectively Target *Clostridioides difficile*

We discovered the isonicotinamide antibacterial 4 during the structure-activity relationship (SAR) exploration on the cinnamonitrile class of antibiotic adjuvants (compounds 1 and 2, Scheme 2) against methicillin-resistant *Staphylococcus aureus* (MRSA). Cinnamonitrile 1, a protein kinase(s) inhibitor, showed promise as an adjuvant for β-lactam antibiotics and also exhibited modest antibacterial activity. Since azoles are common among protein kinase inhibitors, the oxazole was introduced as a favored moiety (compound 3, Scheme 2). Upon insertion of the oxazole, the resulting series of molecules showed respectable Gram-positive antibacterial activity (minimum inhibitory concentration (MIC) ≤4 mg·$L^{-1}$ against MRSA strain NRS70). Further modifications of 3—amide linker, pyridine core, and removal of the bridging oxygen—led to the potent isonicotinamide antibacterial 4.

Scheme 2. Evolution of the structural template of the cinnamonitrile class of protentiators into the isonicotinamide antibacterial 4.

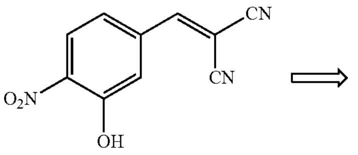

1
MIC against NRS70:
32 mg-L$^{-1}$

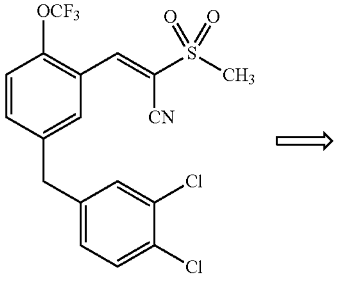

2
8 mg-L$^{-1}$

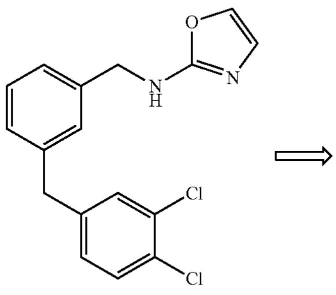

3
4 mg-L$^{-1}$

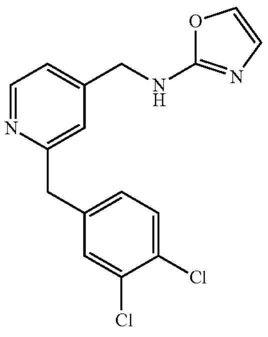

4
0.25 mg-L$^{-1}$

Compound 4 was evaluated against the ESKAPE panel (*Enterococcus faecium, Staphylococcus aureus, Klebsiella pneumoniae, Acinetobacter baumannii, Pseudomonas aeruginosa*, and *Enterobacter* species). These bacteria account for the majority of human problematic infections. The compound was active only against the Gram-positive members of the panel (*E. faecium* and *S. aureus*). We further evaluated 4 against *C. difficile* ATCC 43255, also a Gram-positive bacterium, and obtained an MIC of 0.25 mg-L$^{-1}$. These results provided the impetus for an SAR investigation around this structural template. We report herein the preparation and evaluation of 108 analogs of compound 4 (Scheme 3), of which the prototype picolinamide 1 was reported recently (*ACS Infect. Dis.* 2020, 6, 2362). As will be outlined, several of these analogs exhibited exceptional activities against *C. difficile*, both in potency of the antibiotics and in selectivity toward the organism. The aforementioned selectivity in targeting *C. difficile* is extremely important, as it would avoid gut dysbiosis and mitigates recurrent infections, which are at the root of the bad outcome in the clinical setting.

Scheme 3. Left, the four sites of structure modification for the SAR study as highlighted by the boxes.

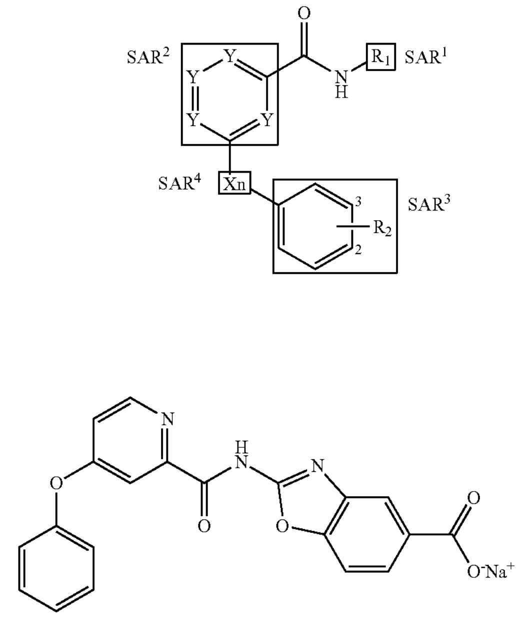

Y = C, N
$X_0$ = No bridging linker
$X_1$ = O

Chemistry. The initial compound of interest, 4, was prepared in three steps following the general Scheme 4A. The first step was a Suzuki-Miyaura coupling reaction between the chloro-cyanopyridine and a benzeneboronic acid 6, using $Pd(PPh_3)_4$ as catalyst and potassium carbonate as a base, yielding the cyano-derivative 7. Alkaline hydrolysis of the nitrile gave the carboxylic acid 8. A coupling reaction between 8 and 1,3-oxazol-2-amine (or other amines) using propanephosphonic anhydride (T3P) as the coupling reagent led to derivatives 9. The preparation of compounds possessing the diarylether moiety followed a similar synthetic route (Scheme 4B). We used the general synthetic route to derivative 5 for syntheses of compounds 112-119.

Scheme 4. Synthetic Routes for Accessing (A) Biaryl and (B) Biarylether Derivatives.

A

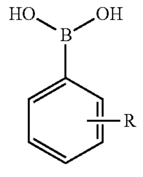

6

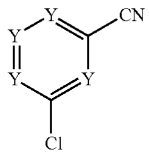

Y = C, N

Pd(PPh$_3$)$_4$

K$_2$CO$_3$ 61-79%

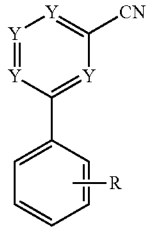

7

NaOH 57-97%

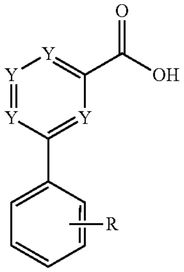

8

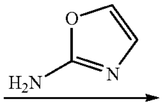

T$_2$P,

Pyridine 8-64%

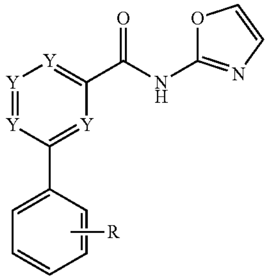

9

B

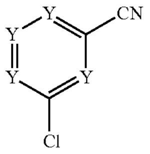

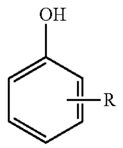

10

Y = C, N

K$_2$CO$_3$ 70-87%

-continued

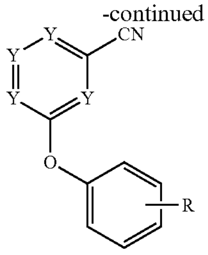

11

NaOH 83-96%

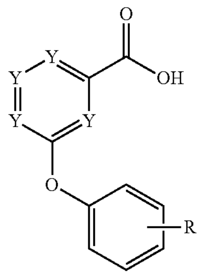

12

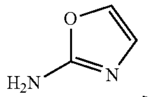

T$_3$P,

Pyridine 20-49%

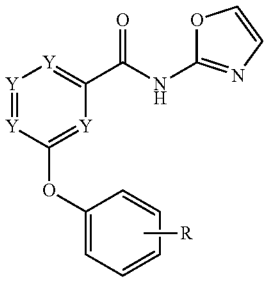

13

Biological Evaluation. The syntheses produced 108 analogs corresponding to diversification at four structural regions (Scheme 3, left structure with four different colored boxes). A representative *C. difficile* strain (ATCC43255) along with MRSA strain NRS70 were chosen for MIC evaluation (Table 2-5, SAR$^1$ to SAR$^4$). A selected few were further tested against methicillin-sensitive *S. aureus* (MSSA) and *E. faecium* (Table 10). Compounds with MICs of ≤8 mg·L$^{-1}$ against *C. difficile* were considered active.

SAR$^1$ involved modifications of the oxazole ring in lead compound 4, a main substructure that defines the antibacterial activity of the isonicotinamides. The removal of the oxazole (compound 20) or other minor alterations (compounds 16-19) led to total loss of the activity against *C. difficile* and MRSA (MIC≥64 mg-L$^{-1}$), while small structure modification (compounds 14, 15, and 23), or a fused aromatic ring (compounds 21 and 22), sustained or enhanced activity. As compound 23 showed activity against MRSA and *C. difficile*, a set of variations (compounds 24-31) were made and tested. A majority of these compounds retained activity against both bacteria, albeit with poor selectivity.

TABLE 2

Activity of Picolinamides Analogs against MRSA and *C. difficile* (SAR[1]).

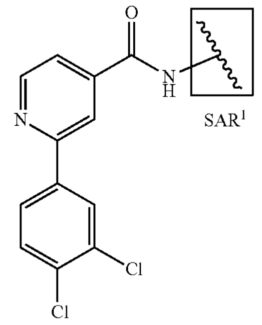

| | SAR[1] | $R_1$ | MIC ($mg \cdot L^{-1}$) MRSA[a] | *C. difficile*[b] |
|---|---|---|---|---|
| 4 | 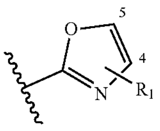 | H | 0.25 | 0.25 |
| 14 | | 4-Methyl | 0.06 | 0.25 |
| 15 | | 4-$CO_2Et$ | 1 | 0.125 |
| 16 | 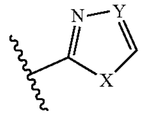 | X = S, Y = CH | ≥256 | ≥128 |
| 17 | | X = N, Y = CH | ≥256 | ≥128 |
| 18 | | Y = O, X = CH | ≥256 | ≥128 |
| 19 | 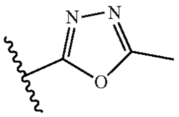 [SMILES: *c1nnc(C)o1] | — | ≥256 | 64 |
| 20 | $—CH_3$ | — | ≥256 | 64 |
| 21 | 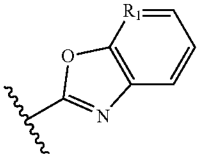 | CH | 1 | 1 |
| 22 | | N | 0.25 | 0.0625 |
| 23 | 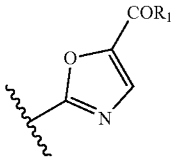 | OEt | 0.06 | 0.0625 |
| 24 | | OH | 64 | 128 |
| 25 | | $O(CH_2)_5C≡CH$ | 0.06 | 0.25 |
| 26 | | $O(CH_2)_6OH$ | 0.25 | 0.25 |
| 27 | | $O(CH_2)_6NHBoc$ | 16 | 8 |
| 28 | | $N(Me)_2$ | 4 | 0.5 |
| 29 | | Morpholin-1-yl | 2 | 0.125 |
| 30 | | 4-Boc-piperazin-1-yl | 2 | 0.25 |
| 31 | | Piperazin-1-yl•2HCl | 16 | 8 |

[a]NRS70 strain, resistant to erythromycin and spectinomycin;
[b]ATCC 43255, ribotype 087.

The SAR study then focused on optimizing the phenyl ring ($SAR^3$) with respect to the central pyridine ring ($SAR^2$), while leaving the oxazole group intact (Table 3). Table 3 shows the effect of substitution on the phenyl ring and its selective replacement. The presence of halides on the phenyl ring (32-48, 54) gave potent antibacterial activity, while many of the other substituents increased the MIC (49-53, 55, 56, 58-61). Replacement of the phenyl ring with an N-morpholinyl ring (62) abolished antibacterial activity, whereas its replacement by a small hydrophobic substituent such as $CF_3$ retained moderate antibacterial activity (63-65).

Further optimization focused on the modification of the pyridine segment. The resulting isonicotinamide series introduced a fluorine group in the pyridine at position 3 (66-69) and position 5 (70-74). The resulting MIC values were similar to their non-fluorinated counterparts. Various heterocyclic modifications were also studied in $SAR^2$ and $SAR^3$, each with halides on the phenyl ring. The 2,5-substituted picolinamide (75-80), nicotinamide (81 and 82), pyrimidine (83-85), and pyrazine derivatives (86) were less active.

TABLE 3
Activity of Picolinamides Analogs against MRSA and *C. difficile* ($SAR^2$ and $SAR^3$).
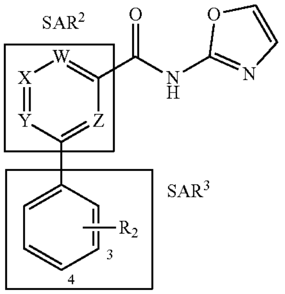
| | $SAR^2$ | $SAR^3$ | MIC (mg · $L^{-1}$) MRSA[a] | *C. difficile*[b] | Selectivity[c] |
|---|---|---|---|---|---|
| 4 | 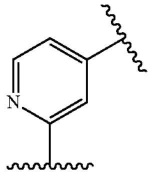 [SMILES: *c1ccnc(*)c1] | 3,4-Cl | 0.25 | 0.25 | 1 |
| 32 | | 4-Cl | 1 | 0.50 | 2 |
| 33 | | 3-Cl | 0.25 | 0.50 | 0.5 |
| 34 | | 2-Cl | 8 | 4 | 2 |
| 35 | | 3,4-F | 2 | 1 | 2 |
| 36 | | 4-F | 4 | 2 | 2 |
| 37 | | 3-F | 2 | 1 | 2 |
| 38 | | 2-F | 1 | 4 | 0.25 |
| 39 | | 3-F, 4-Cl | 0.0625 | 0.125 | 0.5 |
| 40 | | 3-Cl, 4-F | 0.25 | 0.25 | 1 |
| 41 | | 3,5-Cl | 0.0625 | 0.0625 | 1 |
| 42 | | 3,5-F | 8 | 0.50 | 16 |
| 43 | | 3-Cl, 5-F | 0.0625 | 0.12 | 0.5 |
| 44 | | 4-$CF_3$ | 1 | 0.25 | 4 |
| 45 | | 3-$CF_3$ | 0.25 | 0.25 | 1 |
| 46 | | 4-$OCF_3$ | 1 | 0.125 | 8 |
| 47 | | 3-$OCF_3$ | 0.0625 | 0.25 | 0.25 |
| 48 | | 4-Br | 0.25 | 0.50 | 0.5 |
| 49 | | 4-$NO_2$ | 64 | 1 | 64 |
| 50 | | 3-$NO_2$ | ≥256 | 2 | ≥128 |
| 51 | | 4-OMe | 8 | 4 | 2 |
| 52 | | 4-OiPr | 4 | 2 | 2 |
| 53 | | 3,4-OMe | 64 | 16 | 4 |
| 54 | | 3-Cl, 4-OMe | 1 | 0.50 | 2 |
| 55 | | 3-CN | 32 | 4 | 8 |
| 56 | | 4-OBn | 8 | 4 | 2 |
| 57 | | 3-OBn | 1 | 0.50 | 2 |
| 58 | | 4-NHBoc | 8 | 8 | 1 |
| 59 | | 3-NHBoc | 4 | 8 | 0.5 |
| 60 | | H | 8 | 8 | 1 |
| 61 | | 3-quinolinyl | 16 | 4 | 4 |
| 62 | | N-morpholinyl | 128 | 128 | 1 |
| 63 | | —$CF_3$ | 16 | 4 | 4 |
| 64 | | $OCH_2CF_3$ | 4 | 2 | 2 |
| 65 | | $O(CH_2)_2CF_3$ | 8 | 4 | 2 |
| 66 | 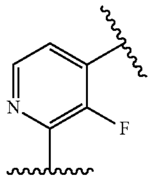 [SMILES: *c1ccnc(*)c1F] | 3,4-Cl | 2 | 0.25 | 8 |
| 67 | | 3-Cl, 4-F | 1 | 1 | 1 |
| 68 | | 3,4-F | 4 | 2 | 2 |
| 69 | | 3-Cl | 2 | 1 | 2 |
| 70 | 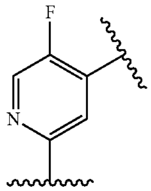 [SMILES: *c1cc(*)c(F)cn1] | 3,4-Cl | 0.0625 | 0.125 | 0.5 |
| 72 | | 3,4-F | 4 | 0.50 | 8 |
| 73 | | 3-Cl, 4-F | 2 | 0.50 | 4 |
| 74 | | 4-Cl, 3-F | 2 | 0.25 | 8 |

TABLE 3-continued

Activity of Picolinamides Analogs against MRSA and *C. difficile* ($SAR^2$ and $SAR^3$).

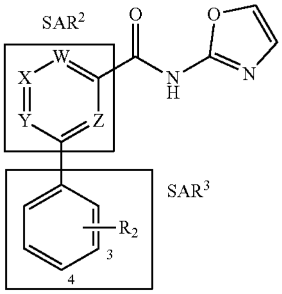

| | $SAR^2$ | $SAR^3$ | MIC ($mg \cdot L^{-1}$) MRSA[a] | *C. difficile*[b] | Selectivity[c] |
|---|---|---|---|---|---|
| 75 | 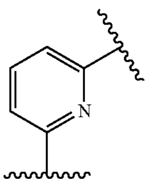 [SMILES: *c1cccc(*)n1] | 3,4-Cl | 2 | ≥16 | ≤0.125 |
| 76 | | 3-Cl | 4 | 8 | 0.5 |
| 77 | | 3-Cl, 4-F | 8 | 8 | 1 |
| 78 | | 4-Cl, 3-F | 128 | ≥16 | ≤8 |
| 79 | | 4-F | 32 | ≥16 | ≤2 |
| 80 | | 3,4-F | 64 | ≥16 | ≤4 |
| 81 | 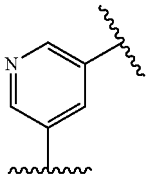 [SMILES: *c1cncc(*)c1] | 3-Cl, 4-F | 8 | 2 | 4 |
| 82 | | 3,4-F | 8 | 4 | 2 |
| 83 | 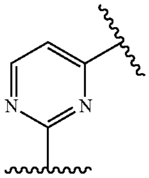 [SMILES: *c1ccnc(*)n1] | 3,4-Cl | 0.50 | 1 | 0.5 |
| 84 | | 3-Cl | 4 | 4 | 1 |
| 85 | | $3-CF_3$ | 2 | 2 | 1 |
| 86 | 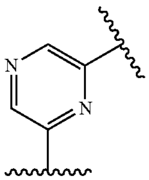 [SMILES: *c1cncc(*)n1] | 3,4-Cl | 4 | 8 | 0.5 |
| 87 | 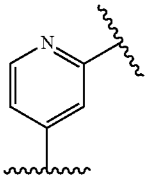 [SMILES: *c1ccnc(*)c1] | 3,4-Cl | 128 | 0.125 | 1024 |
| 88 | | 4-Cl | 128 | 4 | 32 |
| 89 | | 4-F | 64 | 1 | 64 |
| 90 | | 3,4-F | 128 | 0.50 | 256 |
| 91 | | 3-Cl, 4-F | 128 | 0.25 | 512 |
| 92 | | 4-Cl, 3-F | 128 | 0.25 | 512 |
| 93 | | 3-F | 64 | 0.50 | 128 |
| 94 | | 3,5-F | 64 | 1 | 64 |
| 95 | | $4-OCF_3$ | 128 | 0.25 | 512 |
| 96 | | $3-OCF_3$ | ≥256 | 0.50 | ≥512 |
| 97 | | $4-CF_3$ | 128 | 0.25 | 512 |
| 98 | | $3-CF_3$ | 64 | 0.50 | 128 |

[a]NRS70 strain, resistant to erythromycin and spectinomycin;
[b]ATCC 43255, ribotype 087;
[c]selectivity is defined as $MIC_{MRSA}/MIC_{C.\ difficile}$.

Introduction of an ether linkage between the pyridine core and the phenyl ring resulted in MIC values for *C. difficile* of ≤1 $mg \cdot L^{-1}$ (Table 4). The picolinamides (106-111) had significantly higher selectivity for *C. difficile* than the isonicotinamides (99-105). Unfortunately, the introduction of the ether linkage did not increase the antibacterial activity of the picolinamides. These SAR studies led us to introduce a carboxylate, either as a salt or as an ester (compounds 112-119; Table 5), which improved water solubility of the family while still maintaining potent activity against *C. difficile* (0.12 mg·$L^{-1}$ for 5 and 0.50 mg·$L^{-1}$ for 116).

The most compelling modification was 3,5-substitution of the picolinamide (87-98). This substitution imparted the desired selectivity toward *C. difficile* compared to MRSA. Picolinamide 87, a constitutional isomer of compound 4, was inactive against MRSA (MIC=128 mg $L^{-1}$) yet active against *C. difficile* (MIC=0.125 mg $L^{-1}$). This exquisite selectivity of 1024-fold was achieved by the mere repositioning of one nitrogen atom. Moreover, compounds 87-98 lacked activity against MSSA and *E. faecium* (Table 10).

X-Ray Crystal Structure for 87. Confirmation of the structure of picolinamide 87 was obtained by X-ray crystallography. The crystal structure of compound 87 has been deposited to the Cambridge Crystallographic Data Centre, deposition number CCDC2050429. Crystallization of 87 produced colorless block-like crystals.

In Vitro Cytotoxicity. The XTT (2,3-bis-(2-methoxy-4-nitro-5-sulfophenyl)-2H-carboxanilide) assay with HeLa cells was performed on representative compounds (Table 6). Most of the compounds tested had $IC_{50}$ values>64 mg-$L^{-1}$ (except for picolinamides 94 and 114, and isonicotinamide 99). Compound 87 had $IC_{50}$ of 95.2±1.0 mg-$L^{-1}$, 760-fold higher than its MIC (0.125 mg-$L^{-1}$).

TABLE 6

XTT $IC_{50}$ of Selected Picolinamides Analogs with HeLa Cells.

| | $IC_{50}$ (mg · $L^{-1}$) |
|---|---|
| 4 | 79.9 ± 1.0 |
| 5 | 179.3 ± 3.6 [a] |
| 87 | 95.2 ± 1.0 |
| 89 | 170.2 ± 2.5 |
| 90 | NT at 64 [b] |
| 92 | NT at 256 [b] |
| 93 | NT at 64 [b] |
| 94 | 40.1 ± 1.6 |
| 97 | 135 ± 8.6 |
| 98 | 114.8 ± 2.2 |
| 99 | 37.0 ± 1.0 |
| 106 | 105.9 ± 2.1 |
| 107 | 88.0 ± 2.3 |
| 108 | 93.3 ± 1.7 |
| 109 | 77.4 ± 2.3 |
| 110 | 91.6 ± 1.3 |

TABLE 6-continued

XTT $IC_{50}$ of Selected Picolinamides Analogs with HeLa Cells.

| | $IC_{50}$ (mg · $L^{-1}$) |
|---|---|
| 114 | 53.3 ± 3.6 |
| 116 | NT at 128 [b] |
| 118 | 79.9 ± 6.3 |
| 119 | 123.6 ± 3.3 |

[a] Reported previously (*ACS Infect. Dis.* 2020, 6, 2362) and included here for comparison.
[b] NT, no detectable toxicity at the specified concentration.

Picolinamide 87 Selectively Targets *C. difficile*. The picolinamide core in $SAR^2$ had exquisite selectivity against *C. difficile* compared to MRSA. We evaluated the activity of selected compounds against 20 additional strains of *C. difficile* (Table 7). The MIC values for the non-selective isonicotinamide compound (4) ranged from 0.0625 to 0.5 mg $L^{-1}$. The MIC values for the *C. difficile*-selective picolinamide compounds (5, 87, and 108) ranged from 0.0625 to 1 mg·$L^{-1}$. Both type of compounds showed consistent antibacterial effects on *C. difficile* strains, even for those resistant to MTZ, VAN, and FDX. We also evaluated the activity of the picolinamides against the common gut bacteria: *Bacteroides fragilis, Bijfidobacterium longum, Corynebacterium* spp., *Fusobacterium nucleatum, Lactobacillus reuteri, Lactobacillus gasseri, Veillonella* sp., and *Eubacterium* sp. An optimum antibacterial will target selectively the pathogenic bacterium and not the natural gut flora. Picolinamides 5 and 87 were more selective than 4 and more selective than the clinically used antibiotics VAN, MTZ, and FDX. Its selectivity is evident especially with respect to *Bifidobacterium longum*, a major gut bacterium that is reported to help repress CDI.

For the purpose of comparison, the currently clinically used antibiotics, vancomycin and fidaxomicin have selectivities of 4- and 128-fold, respectively, toward *C. difficile* ATCC43255 relative to MRSA NRS7 (Table 7). Recurrence of CDI for the less selective vancomycin is 25%, while that for the somewhat more selective fidaxomicin is 15%. Picolinamide 87 is >1000-fold selective. As gut dysbiosis contributes to CDI recurrence, the importance of this high selectivity is self-evident. Selectivity in targeting *C. difficile* emerges as an important attribute as mere potency (low MIC) might become less significant given that a compound such as 87 has already a remarkably very low/potent MIC of 0.125 mg·$L^{-1}$. (nanomolar range).

TABLE 7

MIC Values (mg · $L^{-1}$) for MTZ, VAN, FDX, and Compounds 4, 5, 87, and 108 against *C. difficile*, MRSA NRS70, and Major Gut Bacteria.

| | MTZ | VAN | FDX | 4 | 5[a] | 87 | 108 |
|---|---|---|---|---|---|---|---|
| *C. difficile* | | | | | | | |
| BAA-1870 | 0.5 | 2 | 0.25 | ≤0.25 | 0.125 | 0.25 | 0.5 |
| BAA-1804 | 0.25 | 1 | <0.25 | 0.0625 | 0.125 | 0.125 | 0.25 |
| BAA-1803 | 0.5 | 2 | 1 | 0.5 | 0.0625 | 0.25 | 0.5 |
| BAA-1801 | 0.125 | 0.25 | 0.125 | 0.25 | 0.125 | 0.25 | 0.25 |
| BAA-1812 | 0.25 | 0.5 | 0.015 | 0.125 | 0.125 | 0.25 | 1 |
| BAA-1814 | 0.25 | 0.5 | 0.03 | 0.125 | 0.125 | 0.125 | 0.25 |
| ATCC43598 | 0.125 | 1 | 0.01 | 0.0625 | 0.125 | 0.25 | 0.5 |
| NR49310 | 0.125 | 0.5 | ≤0.01 | 0.0625 | 0.125 | 0.125 | 0.5 |
| NR49294 | 0.25 | 0.25 | 0.01 | 0.0625 | 0.0625 | 0.25 | 0.25 |
| NR49305 | 0.25 | 0.5 | 0.01 | 0.125 | 0.0625 | 0.25 | 0.25 |
| ATCC43255 | 0.25 | 0.5 | 0.0625 | 0.25 | 0.125 | 0.125 | 1 |
| NR49318 | 0.25 | 0.25 | 0.125 | 0.125 | 0.06 | 0.25 | 0.5 |
| NR49292 | 0.25 | 0.25 | 0.5 | 0.125 | 0.125 | 0.25 | 0.25 |
| NR49302 | 0.125 | 0.5 | 0.03 | 0.0625 | 0.0625 | 0.25 | 1 |
| 26675 (MR) [b] | 4 | 1 | 4 | 0.25 | 0.25 | 0.5 | 1 |
| 27173 (MR) [b] | 4 | 0.5 | 0.01 | 0.125 | 0.125 | 0.5 | 0.5 |

TABLE 7-continued

MIC Values (mg · $L^{-1}$) for MTZ, VAN, FDX, and Compounds 4, 5, 87, and 108 against *C. difficile*, MRSA NRS70, and Major Gut Bacteria.

| | MTZ | VAN | FDX | 4 | 5[a] | 87 | 108 |
|---|---|---|---|---|---|---|---|
| 27081 (FR) [c] | 0.5 | 1 | >8 | 0.125 | 0.125 | 0.5 | 0.25 |
| 23828 (FR) [c] | 0.5 | 2 | >8 | 0.125 | 0.25 | 0.25 | 1 |
| 24923 (VR) [d] | 0.25 | 8 | 0.0625 | 0.125 | 0.125 | 0.5 | 0.25 |
| 24531 (VR) [d] | 0.5 | 4 | 0.01 | 0.125 | 0.25 | 0.25 | 0.25 |
| 23691 (VR) [d] | 0.5 | 4 | 4 | 0.25 | 0.125 | 0.5 | 0.25 |
| MRSA NRS70 | >128 | 2 | 8 | 0.25 | 16 | 128 | 64 |
| Selectivity [e] | >512 | 4 | 128 | 1 | 128 | 1024 | 64 |
| Major Gut Bacteria | | | | | | | |
| *Bacteroides fragilis* [f] | 1 | 16 | >32 | 1 | 4 | 4 | 8 |
| *Bifidobacterium longum* [g] | 1 | 0.25 | <0.01 | >16 | 16 | >16 | 16 |
| *Corynebacterium* spp. [h] | >32 | 0.5 | <0.0625 | 0.5 | 8 | 16 | >16 |
| *Fusobacterium nucleatumi* [h] | 2 | 0.25 | <0.0625 | 8 | 4 | 8 | 8 |
| *Lactobacillus reuteri* [j] | >32 | >32 | >32 | 8 | 4 | 4 | 4 |
| *Lactobacillus gasseri* [k] | >32 | 1 | 2 | >16 | >16 | >16 | >16 |
| *Veillonella* sp. [l] | 2 | >32 | 8 | 4 | 16 | 16 | 16 |
| *Eubacterium* sp. [m] | 1 | 2 | 16 | >16 | 16 | 8 | 8 |

[a]Data reported previously (*ACS Infect. Dis.* 2020, 6, 2362) and included for comparison.

[b] MR = metronidazole-resistant.

[c] FR = fidaxomicin-resistant.

[d] VR = vancomycin-resistant.

[e] Selectivity is defined as $MIC_{MRSA\ NRS70}/MIC_{C.\ difficile\ ATCC43255}$.

[f] Strain HM-709, a Gram-negative, anaerobic bacterium that is commensal and critical to host immunity and a minor component of the human gut microflora (<1%).

[g] Strain HM-846, an anaerobic, nonsporulating Gram-positive bacterium commonly found in the normal human intestinal microflora isolated from human feces.

[h] Strain HM-784, an aerobic or facultatively anaerobic Gram-positive bacterium that occurs in the mucosa and normal skin flora of humans and animals.

[i]Strain HM-992, an anaerobic, nonsporulating Gram-negative bacterium commonly found in the gastrointestinal tract.

[j] Strain HM-102, an anaerobic Gram-positive bacterium commonly found in the normal human gastrointestinal tract, and used frequently as a probiotic to maintain the balance of gut microbial flora.

[k] Strain HM-644, a facultative, anaerobic Gram-positive bacterium commonly found in the normal human gastrointestinal tract, used frequently in yogurt production as a probiotic to suppress *Helicobacter pylori* infections.

[l] Strain HM-49, a nonsporulating Gram-negative bacterium commonly found in the intestinal tract of humans and animals.

[m] Strain HM-178, an anaerobic, nonsporulating Gram-positive bacterium commonly found in the gastrointestinal flora of humans and animals.

In vivo Pharmacokinetics (PK). For the treatment of CDI, compounds that are poorly or not absorbed and achieve high concentrations in the gut are desirable. We selected compounds 4, 87, 107, 108, and 116 for in vivo PK studies in mice based on their potency, safety profile, solubility, and selectivity against *C. difficile*. Both plasma and feces were collected and analyzed for levels of the compounds and compared to those of compound 5. While all the compounds showed non-quantifiable concentrations in plasma, levels in feces were higher (Table 8). The selected compounds showed 2- to 50-fold higher concentrations in the feces over the MIC values.

TABLE 8

Drug Concentrations in Fecal Samples of Selected Compounds.

| | MIC mg · $L^{-1}$ | Selectivity | Dose mg · $kg^{-1}$ | mg $kg^{-1}$ feces | Conc. feces /MIC |
|---|---|---|---|---|---|
| 4 | 0.25 | 1 | 20 | 2.8 | 11 |
| 5 [a] | 0.125 | 128 | 20 | 13 | 108 |
| 87 | 0.125 | 1024 | 10 | 0.79 | 6.6 |
| 107 | 1 | >256 | 20 | 2.4 | 2.4 |
| 108 | 1 | 64 | 20 | 49 | 49 |
| 116 | 0.50 | 128 | 20 | 3.7 | 7.4 |

[a] Reported previously; included for ease of comparison.

Conclusion. The lack of selective antibiotics for the treatment of CDI contributes to gut dysbiosis and recurrence of CDI. The picolinamide family of antibacterials shows exquisite potency and selectivity in targeting *C. difficile*. Starting with isonicotinamide 4, a compound that is equally active against MRSA and *C. difficile*, structure optimization gave the new picolinamide 87 with >1,000-fold selectivity for *C. difficile* compared to MRSA (Strain NRS70). Compound 87 shows exceptional selectivity against *C. difficile* while lacking activity against other, normal Gram-positive and Gram-negative gut microbiota. As gut dysbiosis contributes to CDI recurrence, the picolinamides have the potential for treatment of recurrent CDI.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard- or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.50% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 $mg/m^2$, conveniently 10 to 750 $mg/m^2$, most conveniently, 50 to 500 $mg/m^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective antibacterial agents and have higher potency and/or reduced toxicity as compared to vancomycin (VAN), metronidazole (MTZ), or fidaxomicin (FDX). Preferably, compounds of the invention are more potent and less toxic than VAN, MTZ, or FDX, and/or avoid a potential site of catabolic metabolism encountered with VAN, MTZ, or FDX, i.e., have a different metabolic profile than VAN, MTZ, or FDX.

The invention provides therapeutic methods of treating a bacterial infection in a mammal, which involve administering to a mammal having a bacterial infection an effective amount of a compound or composition described herein. A mammal includes a primate, human, rodent, canine, feline, bovine, ovine, equine, swine, caprine, bovine and the like. A bacterial infection can refer to a Gram-positive or Gram-negative bacterial infection.

The ability of a compound of the invention to treat a bacterial infection may be determined by using assays well known to the art. For example, the design of treatment protocols, toxicity evaluation, data analysis, quantification of cell kill. In addition, ability of a compound to treat a bacterial infection may be determined using the Tests as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Synthesis of Compounds

Scheme 5: Synthetic route for compound 1.

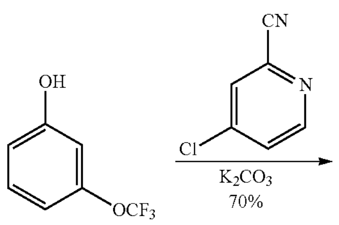

2

-continued

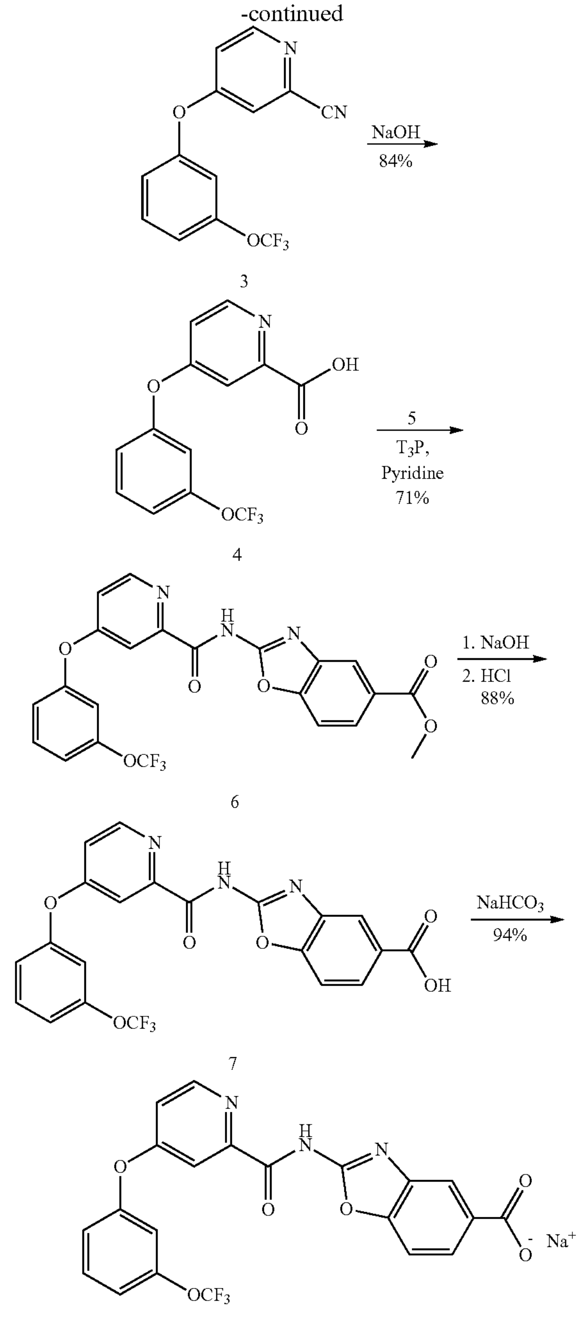

3, 4, 6, 7, 1

4-(3-(Trifluoromethoxy)phenoxy)picolinonitrile (3). Compound 2 (4.24 g, 23.8 mmol), 4-chloropyrimidine-2-carbonitrile (3.0 g, 21.7 mmol), $K_2CO_3$ (23.8 mmol), and dry dimethylformamide (DMF, 40 mL) were added to a 125 mL oven-dried round-bottom flask and heated at 120° C. for 1 hour. The reaction mixture was cooled and concentrated under reduced pressure. Ethyl acetate (120 mL) was added and the organic phase was washed with water (2×120 mL) and brine (120 mL). The organic layer was dried over anhydrous $Na_2SO_4$. The suspension was filtered and the filtrate was evaporated under reduced pressure to give the crude product. Purification by silica-gel chromatography (gradient elution from 9:1 hexane/EtOAc to EtOAc) afforded the desired 3 as a colorless liquid in 70% yield (4.25 g). $^1H$ NMR (400 MHz, DMSO-$d_6$) δ ppm 8.62 (d, J=5.6 Hz, 1H), 7.76 (d, J=2.7 Hz, 1H), 7.60-7.67 (m, 1H), 7.32-7.37 (m, 2H), 7.30 (ddd, J=1.0, 2.3, 8.3 Hz, 1H), 7.26 (dd, J=2.6, 5.8 Hz, 1H); $^{13}C$ NMR (101 MHz, DMSO-$d_6$) δ ppm 164.1, 154.0, 153.2, 149.41 (q, J=6 Hz), 134.4, 132.1, 122.5 (q, J=259 Hz), 119.7, 118.7, 118.4, 118.0, 117.0, 115.6, 114.1; $^{19}F$ NMR (376 MHz, DMSO-$d_6$) δ ppm −57.15; HRMS (m/z): $[M+H]^+$, calcd for $C_{13}H_8F_3N_2O_2$, 281.0536; found, 281.0536.

4-(3-(Trifluoromethoxy)phenoxy)picolinic acid (4). Compound 3 (2.80 g, 10 mmol), ethanol (40 mL), and water (20 mL) were added to a 250 mL round-bottom flask. Sodium hydroxide (1.00 g, 25.1 mmol) was added. The reaction was stirred at reflux overnight. The solution was let to cool to room temperature. The solvent was evaporated under reduced pressure to half of its volume. The desired product precipitated from the solution upon adjustment of pH to 3.0. The precipitate was filtered and washed with water (3×10 mL). The solid was dried (high vacuum overnight) to give 4 as a white solid in 84% yield (2.51 g). $^1H$ NMR (400 MHz, DMSO-$d_6$) δ ppm 10.78 (br s, 1H), 8.67 (d, J=5.9 Hz, 1H), 7.68 (t, J=8.3 Hz, 1H), 7.57 (d, J=2.5 Hz, 1H), 7.26-7.46 (m, 4H); $^{13}C$ NMR (101 MHz, DMSO-$d_6$) δ ppm 165.8, 164.5, 154.1, 150.3, 149.3 (q, J=7 Hz), −132.2, 122.5 (q, J=258 Hz), 120.0, 118.7-118.6, 115.4, 114.3, 113.1; $^{19}F$ NMR (376 MHz, DMSO-$d_6$) δ ppm −56.94. HRMS (m/z): $[M+H]^+$, calcd for $C_{13}H_9F_3NO_4$, 300.0478; found, 300.0482.

Scheme 6: Synthetic route for compound 5.

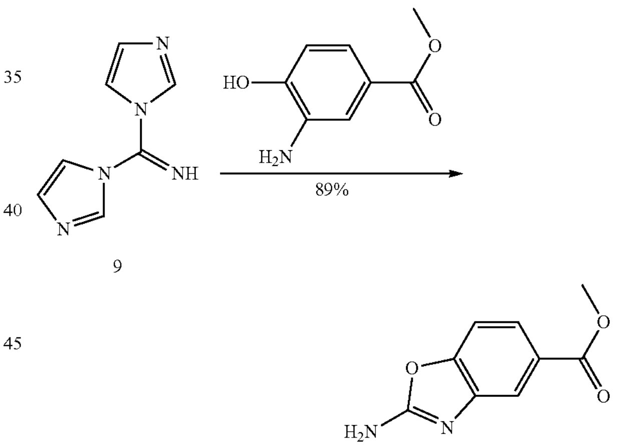

9, 5

Methyl 2-aminobenzo[d]oxazole-5-carboxylate (5). Methyl 3-amino-4-hydroxybenzoate (1 g, 6 mmol), compound 9 (1.74 g, 10.8 mmol) and 70 mL of dry tetrahydrofuran (THF) were added to an oven-dried round-bottom flask, under an atmosphere of nitrogen. The solution was then aged at reflux for 2 h. The solvent was removed under reduced pressure. The resultant crude product was purified by silica-gel column chromatography (EtOAc/hexane 1:9 to EtOAc) affording a light yellow-colored powder. Yield 1.12 g, 89%. $^1H$ NMR (400 MHz, DMSO-$d_6$) δ ppm 7.72 (d, J=1.7 Hz, 1H), 7.67 (d, J=1.7 Hz), 7.65-7.64 (m, 2H, 7.44 (d, J=8.3 Hz, 1H), 3.84 (s, 3H); $^{13}C$ NMR (101 MHz, DMSO-$d_6$) δ ppm 166.3, 163.7, 151.3, 144.0, 125.3, 122.1, 115.8, 108.4, 52.0; HRMS (m/z): $[M+H]^+$, calcd for $C_9H_9N_2O_3$, 193.0608; found, 193.0620.

Methyl 2-(4-(3-(trifluoromethoxy)phenoxy)picolinamido)benzo[d]oxazole-5-carboxylate (6). Compounds 4 (1.80 g, 6.00 mmol) and 5 (1.73 g, 9.00 mmol), pyridine (2 mL), and EtOAc (4 mL) were added to a 20 mL glass vial under an atmosphere of argon. The heterogeneous mixture was cooled to −20° C. and 50% propane phosphonic acid anhydride in dimethylformamide (T3P 50% DMF, 6 mL) was slowly added. The resulting solution was warmed to room temperature. The mixture was stirred overnight. The solution was chilled to −5° C. and 1.5 mL of a 0.5 M aqueous HCl was added, followed by stirring for 1 h. The resultant precipitate was filtered and rinsed with water (3×5 mL). The solid was taken up into EtOAc (20 mL) and was washed with a saturated solution of sodium bicarbonate (10 mL) and brine (10 mL). The removal under reduced pressure of the organic solvent afforded the product as a white solid in 71% yield (2.02 g). $^1$H NMR (400 MHz, DMSO-$d_6$) δ ppm 12.14 (br s, 1H), 8.70 (d, J=5.6 Hz, 1H), 8.18 (d, J=1.7 Hz, 1H), 7.97 (dd, J=1.8, 8.4 Hz, 1H), 7.81 (d, J=8.6 Hz, 1H), 7.68 (dd, J=9 Hz, 9 Hz, 1H), 7.62 (d, J=2.7 Hz, 1H), 7.27-7.47 (m, 4H), 3.89 (s, 3H); $^{13}$C NMR (101 MHz, DMSO-$d_6$) δ ppm 165.9, 165.1, 161.9, 155.8, 154.3, 151.1, 150.9, 150.7, 149.4, 132.1, 126.5, 122.5 (q, J=258 Hz), 120.0, 119.6, 118.7, 118.5, 115.9, 114.3, 111.0, 110.5, 52.3; $^{19}$F NMR (376 MHz, DMSO-$d_6$) δ ppm −56.92; HRMS (m/z): $[M+H]^+$, calcd for $C_{22}H_{15}F_3N_3O_6$, 474.0907; found, 474.0909.

2-(4-(3-(Trifluoromethoxy)phenoxy)picolinamido)benzo[d]oxazole-5-carboxylic acid (7). To a solution of sodium hydroxide (338 mg, 8.4 mmol) in 20 mL of dioxane and 20 mL of water was added 6 (1 g, 2.1 mmol). The reaction mixture was stirred at 60° C. for 3 h. The solvent was evaporated under reduced pressure. The resulting solid was taken up in water (10 mL). HCl conc. was added dropwise until pH was 3.0, resulting in precipitation of the desired carboxylic acid. This precipitate was recovered by filtration and dried under high vacuum to give 7 as a white solid in 88% yield (848 mg): $^1$H NMR (400 MHz, DMSO-$d_6$) δ ppm 13.09 (br s, 1H), 12.17 (br s, 1H), 8.70 (d, J=5.6 Hz, 1H), 8.16 (d, J=2.0 Hz, 1H), 7.96 (dd, J=1.7, 8.3 Hz, 1H), 7.78 (d, J=8.6 Hz, 1H), 7.69 (t, J=8.2 Hz, 1H), 7.62 (d, J=2.7 Hz, 1H), 7.42-7.46 (m, 1H), 7.30-7.42 (m, 3H); $^{13}$C NMR (101 MHz, DMSO-$d_6$) δ ppm 166.8, 165.1, 161.9, 155.7, 154.1, 150.9, 150.5, 149.3 (q, J=2 Hz), 132.1, 127.6, 122.4 (q, J=258 Hz), 119.9, 119.4, 118.6, 118.4, 115.8, 114.3, 110.9, 110.2; $^{19}$F NMR (376 MHz, DMSO-$d_6$) δ ppm −56.91; HRMS (m/z): $[M+H]^+$, calcd for $C_{21}H_{13}F_3N_3O_6$, 460.0751; found, 460.0725.

Sodium 2-(4-(3-(trifluoromethoxy)phenoxy)picolinamido)benzo[d]oxazole-5-carboxylate (1). The carboxylic acid 7 (325 mg, 0.7 mmol) was dissolved in 6 mL of dimethylformamide (DMF) and was added to a 25-mL round-bottom flask. A 1.15 mL portion of a 50 g $L^{-1}$ of sodium bicarbonate in water (0.7 mmol) was added dropwise during 5 min, and the solution was stirred at room temperature for 2 h. The organic solvent was removed under reduced pressure. The solid was filtered and washed with methanol (0.5 mL). The material was dried under high vacuum to produce compound 1 as a white solid in 94% yield (316 mg). $^1$H NMR (400 MHz, DMSO-$d_6$) δ ppm 12.71 (br s, 1H), 8.56 (d, J=5.4 Hz, 1H), 8.00-8.14 (m, 1H), 7.73 (dd, J=2.0, 8.3 Hz, 1H), 7.59-7.71 (m, 2H), 7.38-7.44 (m, 1H), 7.33-7.38 (m, 2H), 7.30 (ddd, J=0.9, 2.2, 8.2 Hz, 1H), 7.09-7.19 (m, 1H); $^{13}$C NMR (101 MHz, DMSO-$d_6$) δ ppm 167.8, 164.0, 154.7, 150.7, 149.9, 149.2 (q, J=2 Hz), 143.0, 131.9, 123.4, 122.5 (q, J=258 Hz), 119.7, 118.6, 117.8, 114.0, 113.8, 111.1, 108.0; $^{19}$F NMR (376 MHz, DMSO-$d_6$) δ ppm −56.85; HRMS (m/z): $[M+H]^+$, calcd for $C_{21}H_{12}F_3N_3NaO_6$, 482.0570; found, 482.0572.

Example 2. In-Vitro and In-Vivo Experimental

Antibiotics. Clindamycin, ciprofloxacin, oxacillin, rifaximin, kanamycin, gentamicin, colistin, vancomycin and metronidazole were purchased from Sigma-Aldrich (St. Louis, MO); linezolid was purchased from AmplaChem Inc., (Carmel, IN); and fidaxomicin was obtained from BOC Sciences (Shirley, NY).

Bacterial strains. A total of 101 *C. difficile* strains were used in the study. Of the isolates, 86 were from Biodefense and Emerging Infections Research Resources Repository (BEI Resources, Manassas, VA), eight from American Type Culture Collection (ATCC, Manassas, VA) and seven resistant *C. difficile* isolates were obtained from Cleveland VA Medical Center. Other gut bacteria strains were obtained from BEI. MRSA strains NRS70 (N315) and NRS119 were obtained through the Network on Antimicrobial Resistance in *Staphylococcus aureus* (NARSA). ATCC 29213 and *E. faecium* NCTC7171 (ATCC 19434) were purchased from ATCC (ATCC; Manassas, VA). All the strains were cultured and stored according to the supplier instructions.

Minimum inhibitory concentrations (MIC). MICs for *C. difficile* strains and the common gut bacteria were determined using broth microdilution techniques as reported earlier using *brucella* broth supplemented with hemin and vitamin K or supplemented BHIS broth. *Lactobacillus* MRS broth was used for *lactobacillus* strains. Sodium lactate was supplemented in the media for *Veillonella* sp. The test compounds were added in 2-fold serial dilutions and the bacteria were added to a final concentration of $5\times10^5$ CFU $mL^{-1}$. All incubations, unless specified otherwise, were carried out at 24 h or 48 h at 37° C. in an anaerobic chamber (Whitley DG250 workstation, Microbiology International, Frederick, MD). *Corynebacterium* and *Lactobacillus* species were incubated aerobically. $MIC_{50}$ and $MIC_{90}$ values for compound 1 against 101 *C. difficile* strains were determined.

XTT assay. Cytotoxicity assays were performed in triplicate against HeLa cells (ATCC CCL-2). The $IC_{50}$ values were calculated by nonlinear regression with GraphPad Prism 5 (San Diego, CA).

Pharmacokinetics (PK) study. Mice (n=2 per time point) were given a single 100 μL solution of 5 mg/mL of compound 1 (equivalent to 20 mg/kg). Terminal blood was collected in heparinized syringes by cardiac puncture at 30 min, 1 h, 2 h, 4 h, and 8 h. The two mice at the 8-h time point were place in metabolism cages for collection of feces. Compound 1 was dissolved in 5% DMSO/95% water with 96 mg/mL of sodium bicarbonate. Blood was centrifuged at 1,000 g for 20 min at 4° C. and plasma was separated and stored at −80° C. until analysis. A 45-μL aliquot of plasma was mixed with 5 μL of $H_2O$:ACN (1:1) and was quenched with 100 μL of acetonitrile containing 20 μM of internal standard (compound 10). The sample was centrifuged at 21,000 g for 15 min at 4° C. to precipitate the proteins, and the resulting supernatant was analyzed by UPLC-TQD detector using multiple-reaction monitoring (MRM). Calibration curves for compound 1 were prepared from 0 to 102.4 μM using a control mouse plasma (50 μL). Peak area ratios relative to internal standard and linear regression was used from which the concentrations in plasma samples from the PK study were determined.

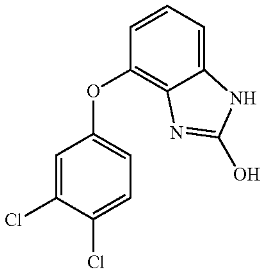

An average of 250 mg of feces were collected at 8 h from two mice, and subsequently homogenized with 6 times the feces volume (1,500 μL of $H_2O$:ACN 1:1) using a Bullet Blender (Next Advance, Inc., Troy, NY). The homogenate was centrifuged at 21,000 g for 5 min. The fecal supernatant (72 μL) was mixed with 8 μL of a solution of $H_2O$:ACN (1:1) and 40 μL of 50 μM of the internal standard in ACN with 0.5% formic acid. A calibration curve was prepared from 0 μM to 102.4 μM in control mouse feces. Plasma and feces were analyzed on a Waters TQD tandem quadrupole detector (Waters Corporation, Milford, MA) using a YMC-Triart C18 100 mm×2.0 mm column (3μ, YMC Co. Ltd, Kyoto, Japan). The chromatographic conditions consisted of elution with 30% $H_2O$/70% ACN containing 0.10% formic acid for 5 min at a flow rate 0.5 mL/min. Mass Spectrometry acquisition was performed in the positive electrospray ionization mode with MRM. The capillary, cone, extractor and RF lens voltages were set at 2.8 kV, 40 V, 1 V and 0.1 V, respectively. The desolvation and cone gas (nitrogen) flow rates were 650 L/h and 50 L/h, respectively. The source temperature was set at 150° C. The desolvation temperature was 350° C. The MRM transitions used were 459.4→254.0 for compound 1, and 294.8→133.5 for the internal standard.

Time-kill assay. For the time kill assay, stationary-phase cultures of *C. difficile* were incubated with compound 1 or VAN at 8×, 16×, and 32×MIC in pre-reduced supplemented *brucella* broth. A control tube without antibiotic was also included. At intervals of 4, 8, and 24 h, 100-μL aliquots of the cultures were plated onto pre-reduced brain heart infusion broth agar media for colony counts. The limit of detection was 50 cfu/mL and a ≥3 $\log_{10}$ reduction of colonies from the starting inoculum was considered bactericidal. The experiment was done in triplicate.

Serial passage. Serial-passage assay for development of resistance in *C. difficile* strain ATCC43255 was performed in duplicate in pre-reduced supplemented *brucella* broth. The starting MIC for the strain against compound 1 and VAN using broth macrodilution assay was 0.125 μg/mL and 0.5 μg/mL respectively. Two-fold serial dilutions of the drugs were prepared from 2×MIC to 0.25×MIC, and cultures were added to a final concentration of $5\times10^5$ CFU/mL. Each day, wells with the highest concentration of drugs showing growth were used to inoculate the series of tubes the next day. The process was repeated for 25 passages. After 25 days, cultures showing a four-fold or higher increase in MIC were confirmed by three passages in drug-free media.

Macromolecular synthesis assay. The macromolecular synthesis assay was performed by established methods. The radioactive precursors and positive controls were [2,8-$^3$H]-adenine and ciprofloxacin for DNA, [5,6-$^3$H]-uridine and rifaximin for RNA, 1-[3,4,5-$^3$H(N)]-leucine and linezolid for protein, and N-acetyl-d-[6-$^3$H]glucosamine and oxacillin for the peptidoglycan synthesis. The radiolabeled precursors were purchased from Perkin Elmer (Waltham, MA, USA).

Scanning-electron microscopy. Bacteria in mid-exponential growth phase were incubated overnight with 4× to 32×MIC of compound 1. Following incubation, the cells were washed with PBS (3×) and applied onto poly-1-lysine (Santa Cruz Biotechnology, Dallas, TX) coated microglass coverslips (Electron Microscopy Sciences, Hatfield, PA) and incubated for 15 min. The cells were fixed for 1 h with 2% glutaraldehyde, followed by a wash (3×) with sodium cacodylate buffer at pH 7.4. The samples were fixed with 1% osmium tetroxide for 1 h and rinsed (3×) in the buffer. The samples were then put through a graded ethanol series for dehydration, followed by critical point drying. The samples were then mounted on SEM stubs and sputter-coated with iridium. Microscopy and imaging were performed on a Magellan 400 XHR instrument (FEI, Hillsboro, OR).

Animals. Female C57BL/6 mice weighing 18-20 g and 6-8 weeks of age were used for the efficacy study (Jackson, Bar Harbor, MI). Female CD-1 mice (24-31 g and 7-8 weeks of age) were used for the PK study. They were housed in groups of five mice in sterile polycarbonate shoeboxes with bedding consisting of ¼-inch corncob (The Andersons Ind., Maumee, OH) and Alpha-Dri (Shepherd Specialty Papers, Inc., Richland, MI). Mice were maintained on a 12-h light/dark cycle at 72° F. and were given Teklad 2918 irradiated extruded rodent diet and water ad libitum. All procedures were performed in accordance with and approved by the University of Notre Dame Institutional Animal Care and Use Committee.

*C. difficile* infection model. The recurrent *C. difficile* infection model reported by Chen et al. was used (Gastroenterology 2008, 135, 1984). Mice (n=10 per group, total 40 mice per study) were given antibiotic cocktail containing kanamycin (0.4 mg $L^{-1}$), gentamicin (0.035 mg $L^{-1}$), colistin (850 U $mL^{-1}$), metronidazole (0.215 mg $L^{-1}$) and vancomycin (0.045 mg $L^{-1}$), in sterile drinking water containing 5% sucrose for 3 days, followed by 2 days of regular water. Subsequently, mice were given a 10 mg/kg intraperitoneal injection of clindamycin. The following day, the mice were infected intragastrically with 104 CFU of *C. difficile* ATCC 43255. Mice were given single oral doses of compound 1 at 20 mg/kg and 40 mg/kg, VAN at 50 mg/kg, or vehicle (5% DMSO/95% water) once a day for 5 days. Body weights and survival were recorded for 25 days. The study was repeated a second time.

TABLE 9

MICs (μg/mL) of compound 1, VAN, MTZ, and FDX against *C. difficile* strains

| *C. difficile* strain ATCC/BEI designations | 1 | VAN | MTZ | FDX |
|---|---|---|---|---|
| BAA-1870 | 0.125 | 2 | 0.5 | 0.25 |
| BAA-1804 | 0.125 | 1 | 0.25 | 0.125 |
| BAA-1803 | 0.06 | 2 | 0.5 | 1 |
| BAA-1801 | 0.125 | 0.25 | 0.125 | 0.125 |
| BAA-1812 | 0.125 | 0.5 | 0.25 | 0.015 |
| BAA-1814 | 0.125 | 0.5 | 0.25 | 0.03 |
| ATCC43598 | 0.125 | 1 | 0.125 | 0.01 |
| NR49310 | 0.125 | 0.5 | 0.125 | ≤0.01 |
| NR49294 | 0.06 | 0.25 | 0.25 | 0.01 |
| NR49305 | 0.06 | 0.5 | 0.25 | 0.01 |
| ATCC43255 | 0.125 | 0.5 | 0.25 | 0.06 |
| NR49318 | 0.06 | 0.25 | 0.25 | 0.125 |
| NR49292 | 0.125 | 0.25 | 0.25 | 0.5 |
| NR49302 | 0.06 | 0.5 | 0.125 | 0.03 |
| 26675 | 0.25 | 1 | 4 | 4 |

TABLE 9-continued

MICs (μg/mL) of compound 1, VAN, MTZ, and FDX against *C. difficile* strains

| *C. difficile* strain ATCC/BEI designations | 1 | VAN | MTZ | FDX |
|---|---|---|---|---|
| 27173 | 0.125 | 0.5 | 4 | 0.01 |
| 27081 | 0.125 | 1 | 0.5 | >8 |
| 23828 | 0.25 | 2 | 0.5 | >8 |
| 24923 | 0.125 | 8 | 0.25 | 0.06 |
| 24531 | 0.25 | 4 | 0.5 | 0.01 |
| 23691 | 0.125 | 4 | 0.5 | 4 |
| NR-13427 | 0.125 | 1 | 1 | 0.03 |
| NR-13428 | 0.125 | 2 | 1 | ≤0.03 |
| NR-13429 | 0.06 | 0.5 | 1 | 0.25 |
| NR-13430 | 0.125 | 0.5 | 0.5 | ≤0.03 |
| NR-13431 | 0.06 | 0.25 | 0.5 | 0.125 |
| NR-13433 | 0.25 | 1 | 0.5 | 0.125 |
| NR-13434 | 0.125 | 0.5 | 0.5 | 0.06 |
| NR-13435 | 0.125 | 0.5 | 0.5 | ≤0.03 |
| NR-13436 | 0.125 | 0.5 | 0.5 | 0.125 |
| NR-13437 | 0.125 | 0.5 | 0.5 | 0.25 |
| NR-13438 | 0.125 | 0.5 | 0.5 | 0.06 |
| NR-13553 | 0.125 | 0.5 | 0.5 | ≤0.03 |
| NR-32882 | 0.125 | 0.5 | 0.25 | 0.06 |
| NR-32883 | 0.125 | 0.5 | 0.5 | 0.125 |
| NR-32884 | 0.125 | 0.5 | 0.5 | 0.03 |
| NR-32885 | 0.25 | 1 | 0.5 | 0.25 |
| NR-32886 | 0.125 | 0.5 | 0.5 | 0.03 |
| NR-32887 | 0.125 | 0.5 | 2 | 0.125 |
| NR-32888 | 0.125 | 0.5 | 0.5 | 0.03 |
| NR-32889 | 0.125 | 2 | 2 | 0.25 |
| NR-32890 | 0.25 | 2 | 0.5 | 0.06 |
| NR-32891 | 0.25 | 1 | 0.25 | 0.03 |
| NR-32892 | 0.125 | 0.5 | 0.5 | 0.03 |
| NR-32895 | 0.25 | 2 | 1 | 0.03 |
| NR-32896 | 0.25 | 2 | 1 | 0.03 |
| NR-32897 | 0.125 | 0.25 | 0.5 | 0.03 |
| NR-32900 | 0.125 | 1 | 1 | 0.03 |
| NR-32903 | 0.25 | 0.5 | 0.5 | 0.03 |
| NR-32904 | 0.125 | 0.25 | 0.5 | 0.03 |
| NR-49277 | 0.125 | 0.5 | 0.5 | 0.06 |
| NR-49278 | 0.125 | 0.5 | 0.5 | 0.25 |
| NR-49279 | 0.125 | 0.5 | 1 | 0.25 |
| NR-49280 | 0.125 | 1 | 1 | 0.125 |
| NR-49281 | 0.06 | 0.5 | 1 | 0.25 |
| NR-49282 | 0.125 | 0.5 | 0.5 | 0.06 |
| NR-49283 | 0.06 | 0.5 | 0.5 | 0.03 |
| NR-49284 | 0.25 | 0.5 | 0.5 | 0.06 |
| NR-49285 | 0.03 | 0.25 | 0.5 | 0.06 |
| NR-49286 | 0.125 | 0.5 | 1 | 0.25 |
| NR-49287 | 0.06 | 0.5 | 0.5 | 0.25 |
| NR-49288 | 0.125 | 0.5 | 0.5 | 0.25 |
| NR-49289 | 0.25 | 0.5 | 0.5 | 0.03 |
| NR-49290 | 0.125 | 0.5 | 1 | 0.06 |
| NR-49291 | 0.125 | 1 | 1 | 0.25 |
| NR-49293 | 0.125 | 0.5 | 0.5 | ≤0.03 |
| NR-49295 | 0.125 | 0.5 | 0.5 | ≤0.03 |
| NR-49296 | 0.125 | 0.5 | 0.5 | ≤0.03 |
| NR-49297 | 0.06 | 0.5 | 0.5 | 0.0125 |
| NR-49298 | 0.06 | 1 | 1 | 0.125 |
| NR-49299 | 0.125 | 0.5 | 0.5 | 0.125 |
| NR-49300 | 0.125 | 0.5 | 0.5 | 0.03 |
| NR-49301 | 0.125 | 0.5 | 0.5 | 0.03 |
| NR-49303 | 0.125 | 0.5 | 0.5 | 0.03 |
| NR-49304 | 0.25 | 0.5 | 0.5 | 0.06 |
| NR-49306 | 0.25 | 1 | 0.5 | 0.03 |
| NR-49307 | 0.125 | 1 | 0.5 | 0.03 |
| NR-49308 | 0.125 | 0.5 | 0.5 | 0.125 |
| NR-49309 | 0.125 | 1 | 0.25 | 0.03 |
| NR-49311 | 0.25 | 0.5 | 0.5 | 0.03 |
| NR-49312 | 0.125 | 0.5 | 0.5 | 0.125 |
| NR-49313 | 0.06 | 0.5 | 0.5 | 0.03 |
| NR-49314 | 0.125 | 0.5 | 0.5 | 0.25 |
| NR-49315 | 0.125 | 0.5 | 0.5 | 0.06 |
| NR-49316 | 0.125 | 0.5 | 0.5 | 0.125 |
| NR-49317 | 0.125 | 0.5 | 0.5 | 0.06 |
| NR-49319 | 0.125 | 0.5 | 0.5 | 0.125 |
| NR-49320 | 0.125 | 1 | 0.5 | 0.125 |
| NR-49321 | 0.25 | 0.25 | 0.5 | 0.125 |

TABLE 9-continued

MICs (μg/mL) of compound 1, VAN, MTZ, and FDX against *C. difficile* strains

| *C. difficile* strain ATCC/BEI designations | 1 | VAN | MTZ | FDX |
|---|---|---|---|---|
| NR-49323 | 0.125 | 0.5 | 0.25 | ≤0.03 |
| NR-49324 | 0.125 | 0.5 | 0.25 | 0.06 |
| NR-49325 | 0.125 | 0.5 | 0.5 | 0.03 |
| NR-49326 | 0.125 | 0.5 | 0.5 | 0.03 |
| NR-49327 | 0.25 | 0.5 | 0.5 | 0.03 |
| NR-49328 | 0.06 | 0.25 | 0.25 | 0.03 |
| NR-49329 | 0.125 | 0.25 | 0.25 | 0.03 |
| HM-88 | 0.25 | 0.5 | 0.25 | 0.03 |
| HM-89 | 0.125 | 0.25 | 0.25 | 0.03 |
| HM-745 | 0.125 | 0.5 | 0.5 | 0.125 |
| HM-746 | 0.125 | 0.5 | 0.25 | ≤0.03 |
| HM-747 | 0.125 | 0.5 | 0.5 | 0.06 |

Example 3. Synthesis Experimental for SAR of the Picolinamide Antibacterials

General Synthetic Procedures. Solvents and chemicals were used as supplied. Reaction progress was monitored by analytical thin-layer chromatography (TLC) on Merck pre-coated silica gel aluminium plates (200 μm, 60 $F_{254}$, Merck KGaA, Darmstadt, German) under 254 nm UV light. Purification of products was accomplished by silica chromatography using a Teledyne ISCO CombiFlash Rf 200i. Proton ($^1H$) and ($^{13}C$) NMR spectra were recorded on a Bruker Avance III HD 400 Nanobay (400 MHz for $^1H$ and 101 MHz for $^{13}C$, Bruker Biospin AG, Fallanden, France) at room temperature. The purity of the compounds was determined by a Waters Acquity UPLC system (Waters Corporation, Milford, MA, USA) with an Ascentis $C_{18}$ column (3 m, 2.1 mm i.d.×100 mm, Supelco) with UV detection was at 245-300 nm. The purity of all final compounds was ≥95% by HPLC. High-resolution mass spectra (HRMS) were obtained on a Bruker-Q II TOF electrospray mass spectrometer.

The synthetic schemes (and the general procedures A, B, C, D, E, and F below) apply to all 108 analogs. Detailed syntheses of 112, 113 and 5 are known. The crystal structure of 87 was solved (Scheme 5 and Table 10) as unambiguous proof of its structure. Synthetic procedures and characterizations are provided on pages S2 and S5. Spectra for representative compounds are given on page S45.

General procedure (A) for phenylnicotinonitrile, phenylisonicotinonitrile, phenylpicolinonitrile, 2-phenylpyrimidine-4-carbonitrile, and 6-phenyl-pyrazine-2-carbonitrile derivatives. Tetrahydrofuran (75 mL), water (30 mL), and $K_2CO_3$ (8.28 g, 60.0 mmol) were added with stirring to a 250-mL flask under an atmosphere of argon. The given boronic acid (23.8 mmol) and the respective bromonicotinonitrile, bromoisonicotinonitrile, bromopicolinonitrile, 2-chloropyrimidine-4-carbonitrile, or 6-chloropyrazine-2-carbonitrile (21.7 mmol) were added after 5 min of stirring. The reaction was purged with argon for 20 min. Tetrakis (triphenylphosphine)-palladium(0) ($Pd(PPh_3)_4$, 750 mg, 0.7 mmol) was added. The reaction mixture was heated to 80° C. overnight. The reaction was quenched by adjusting the solution to pH 4 with 1 M aqueous HCl. The resulting solution was washed with EtOAc (3×60 mL). The organic layers were combined, dried ($Na_2SO_4$), and evaporated to dryness in vacuo. The crude product was purified by silica chromatography using gradient elution from 9:1 hexanes/EtOAc to EtOAc, affording the desired phenylnicotinonitrile, phenylisonicotinonitrile, phenylpicolinonitrile, 2-phenylpyrimidine-4-carbonitrile, or 6-phenylpyrazine-2-carbonitrile. Isolated yields were typically 61-79%.

General procedure (B) for phenoxyisonicotinonitrile and phenoxypicolinonitrile derivatives. The given phenol (23.8 mmol), the respective chloroisonicotinonitrile or chloropicolinonitrile (21.7 mmol), $K_2CO_3$ (23.8 mmol), and dry DMF (40 mL) were added to a 125-mL oven-dried flask and heated at 120° C. for 1 h. The reaction mixture was cooled and concentrated under reduced pressure. The residue was taken up in EtOAc (120 mL). The organic solution was washed with water (2×120 mL) and brine (120 mL), dried ($Na_2SO_4$), and evaporated under reduced pressure affording the crude material. Its purification used silica chromatography with gradient elution from 9:1 hexanes/EtOAc to EtOAc. The purified sample was evaporated to dryness to give the phenoxyisonicotinonitrile or phenylisopicolinonitrile. Isolated yields were typically 70-87%.

General procedure (C) for nicotinic, isonicotinic, picolinic, pyrimidine-4-carbxylic, and pyrazine-2-carboxylic acid derivatives. The phenyl-nicotinonitrile, phenyl-isonicotinonitrile, phenyl-picolinonitrile, 2-phenylpyrimidine-4-carbonitrile, or 6-phenylpyrazine-2-carbonitrile (10 mmol), ethanol (40 mL), and water (20 mL) were added to a 250-mL flask. Sodium hydroxide (1.00 g, 25.1 mmol) was added after 5 min. The reaction was stirred at reflux overnight. The solution was cooled to room temperature, and the solvent was halved by evaporation under reduced pressure. The desired nicotinic, isonicotinic, picolinic, pyrimidine-4-carbxylic, or pyrazine-2-carboxylic acid precipitated from the solution upon acidification to pH 3. The precipitate was filtered and washed with water (3×10 mL). The solid was then dried under reduced pressure. Isolated yields were typically 57-97%.

General procedure (D) for the amide formation on nicotinic, isonicotinic, picolinic, pyrimidine-4-carboxylic, and pyrazine-2-carboxylic acid derivatives. The nicotinic, isonicotinic, picolinic, pyrimidine-4-carbxylic, or pyrazine-2-carboxylic acid (6.00 mmol), the 1,3-oxazol-2-amine or other amine (9.00 mmol), pyridine (2 mL), and EtOAc (4 mL) were added to a 20-mL glass vial, under an atmosphere of argon. The heterogeneous mixture was cooled to below −20° C. and 50% propane phosphonic acid anhydride in DMF (T3P 50% DMF, 6 mL) was added slowly. The resulting solution was allowed to reach room temperature as it was stirred overnight. The solution was chilled at −5° C. and 1.5 mL of a 0.5 M aqueous HCl solution was added. The mixture was stirred for 1 h. The precipitate was filtered and rinsed with water (3×5 mL). The solid was dissolved with EtOAc (20 mL). This solution was washed with a saturated aqueous $NaHCO_3$ (10 mL) and brine (10 mL), dried ($Na_2SO_4$), and filtered. The solvent from the filtrate was evaporated under reduced pressure to afford the crude product. The product was purified by silica chromatography using gradient elution from 9:1 hexanes/EtOAc to EtOAc. Isolated yields were typically 8-71%.

General procedure (E) for the saponification of phenoxypicolinic derivatives. To a solution of NaOH (338 mg, 8.4 mmol) in 20 mL of dioxane and 20 mL of water, was added the respective phenoxypicolinic derivative containing ester (1 g, 2.1 mmol). The reaction mixture was stirred at 60° C. for 3 h. The solvent was evaporated under reduced pressure. The resulting solid was taken up in water (10 mL). Concentrated HCl was added dropwise to the solution to bring to pH 3. The precipitated carboxylic acid was collected by filtration and dried under reduced pressure. Isolated yields were typically 73-91%.

General procedure (F) for the sodium salt preparation of phenoxypicolinic derivatives. The carboxylic acid obtained by the general procedure E (0.7 mmol) was dissolved in 6 mL of DMF and added to a 25 mL flask. A solution of $NaHCO_3$ (0.7 mmol: 1.15 mL of 50 g $L^{-1}$ in water) was added dropwise over 5 min. The solution was stirred at room temperature for 2 h. The organic solvent was removed under reduced pressure. The solid was washed with methanol (0.5 mL) over a small Buchner funnel and dried under reduced pressure. Isolated yields were typically 91-94%.

N-(3-(3,4-dichlorophenoxy)benzyl)oxazol-2-amine (3). A drop of acetic acid was added to a solution of 3-(3,4-dichlorophenoxy)benzaldehyde (0.78 g, 2.92 mmol) and 2-aminoxazole (0.26 g, 3.07 mmol) in $CH_2Cl_2$ (10 mL). After 15 min of stirring, solid $NaBH(OAc)_3$ (0.68 g, 3.21 mmol) was added and the reaction was stirred at room temperature overnight. The solution was diluted with DCM (10 mL) and rinsed with water (20 mL, 3×). The organic phases were collected, dried ($Na_2SO_4$) and purified by silica chromatography (EtOAc/hexanes=1/9), affording a colorless liquid (860 mg, 88%). $^1H$ NMR (400 MHz, $CDCl_3$) δ ppm 7.37 (d, J=8.8 Hz, 1H), 7.33 (t, J=8.0 Hz, 1H), 7.11-7.28 (m, 2H), 7.07 (d, J=2.8 Hz, 1H), 7.01 (d, J=1.8 Hz, 1H), 6.92 (ddd, J=0.9, 2.4, 8.2 Hz, 1H), 6.84 (dd, J=2.8, 8.8 Hz, 1H), 6.77 (s, 1H), 5.22 (br s, 1H), 4.51 (d, J=3.2 Hz, 2H). $^{13}C$ NMR (101 MHz, $CDCl_3$) δ ppm 156.8, 141.1, 133.5, 132.64, 132.61, 131.3, 130.5, 126.9, 126.6, 123.3, 120.7, 118.5, 118.4, 118.3, 47.1. HRMS (m/z): $[M+H]^+$, calcd for $C_{16}H_{13}Cl_2N_2O_2$, 335.0349; found, 335.0345.

Scheme 7. Synthetic route for accessing compound 4

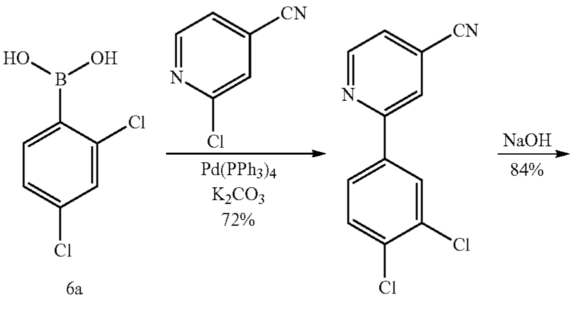

6a

7a

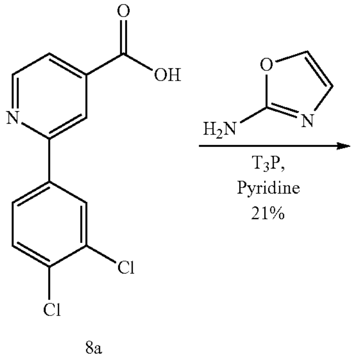

8a

-continued

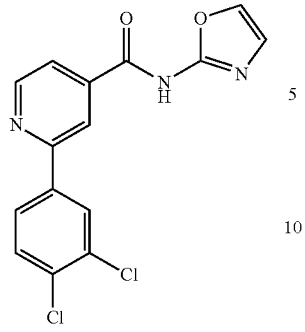

4

2-(3,4-dichlorophenyl)isonicotinonitrile (7a). This compound was prepared by the general procedure A, affording 7a as a white powder in 72% yield (3.86 g). $^1$H NMR (400 MHz, DMSO-$d_6$) δ ppm 8.89 (dd, J=1.0, 4.9 Hz, 1H), 8.57 (t, J=1.2 Hz, 1H), 8.37 (d, J=2.2 Hz, 1H), 8.12 (dd, J=2.2, 8.3 Hz, 1H), 7.86 (dd, J=1.5, 4.9 Hz, 1H), 7.76 (d, J=8.6 Hz, 1H); $^{13}$C NMR (101 MHz, DMSO-$d_6$) δ ppm 154.9, 151.2, 137.7, 133.3, 132.4, 131.5, 128.9, 127.2, 125.3, 123.0, 121.2, 117.2. HRMS (m/z): $[M+H]^+$, calcd for $C_{12}H_7Cl_2N_2$, 248.9981; found, 248.9993.

2-(3,4-dichlorophenyl)isonicotinic acid (8a). This compound was prepared by the general procedure C, affording 8a as a white powder in 84% yield (2.26 g). $^1$H NMR (400 MHz, DMSO-$d_6$) δ ppm 13.79 (br s, 1H), 8.87 (dd, J=0.9, 5.0 Hz, 1H), 8.36-8.41 (m, 2H), 8.14 (dd, J=2.2, 8.3 Hz, 1H), 7.83 (dd, J=1.5, 4.9 Hz, 1H), 7.77 (d, J=8.3 Hz, 1H); $^{13}$C NMR (101 MHz, DMSO-$d_6$) δ ppm 166.0, 154.5, 150.8, 139.7, 138.4, 132.2, 131.9, 131.1, 128.5, 126.8, 122.3, 119.5. HRMS (m/z): $[M+H]^+$, calcd for $C_{12}H_8Cl_2NO_2$, 267.9927; found, 267.9934.

2-(3,4-Dichlorophenyl)-N-(oxazol-2-yl)isonicotinamide (4). This compound was prepared by the general procedure D (Scheme 7), affording 4 as a white powder in 21% yield (416 mg). $^1$H NMR (400 MHz, DMSO-$d_6$) δ ppm 11.98 (br s, 1H), 8.87 (d, J=5.1 Hz, 1H), 8.52 (s, 1H), 8.39 (s, 1H), 8.16 (d, J=8.6 Hz, 1H), 7.99 (br s, 1H), 7.87 (d, J=5.4 Hz, 1H), 7.80 (d, J=8.3 Hz, 1H), 7.25 (br s, 1H). $^{13}$C NMR (101 MHz, DMSO-$d_6$) δ ppm 163.2, 154.3, 152.9, 150.6, 141.3, 138.5, 137.0, 132.3, 131.9, 131.1, 128.4, 127.0, 126.8, 121.5, 118.5; HRMS (m/z): $[M+H]^+$, calcd for $C_{15}H_{10}Cl_2N_3O_2$, 334.0145; found, 334.0157.

2-(3,4-Dichlorophenyl)-N-(4-methyloxazol-2-yl)isonicotinamide (14). This compound was prepared by the general procedures A, C and D affording 14 as a colorless powder (97 mg, 19%). $^1$H NMR (400 MHz, DMSO-$d_6$) δ ppm 11.94 (br s, 1H), 8.87 (d, J=4.9 Hz, 1H), 8.50 (s, 1H), 8.31-8.43 (m, 1H), 8.08-8.22 (m, 1H), 7.84-7.95 (m, 1H), 7.75-7.84 (m, 1H), 7.66 (br s, 1H), 2.12 (d, J=1.5 Hz, 3H). $^{13}$C NMR (101 MHz, DMSO-$d_6$) δ ppm 154.7, 151.0, 139.1, 132.7, 132.3, 131.6, 128.9, 127.2, 122.1, 118.9, 31.1. HRMS (m/z): $[M+H]^+$, calcd for $C_{16}H_{12}Cl_2N_3O_2$, 348.0301; found, 348.0290.

Ethyl 2-(2-(3,4-dichlorophenyl)isonicotinamido)oxazole-4-carboxylate (15). This compound was prepared by the general procedures A, C and D affording 15 as a white powder (185 mg, 40%). $^1$H NMR (400 MHz, DMSO-$d_6$) δ ppm 12.32 (br s, 1H), 8.81-8.99 (m, 1H), 8.74 (br s, 1H), 8.54 (br s, 1H), 8.40 (br s, 1H), 8.17 (d, J=9.1 Hz, 1H), 7.68-7.94 (m, 2H), 4.30 (q, J=7.2 Hz, 2H), 1.30 (t, J=7.1 Hz, 3H). $^{13}$C NMR (101 MHz, DMSO-$d_6$) δ ppm 163.5, 161.1, 154.8, 154.0, 151.2, 142.6, 141.6, 139.0, 132.8, 132.39, 132.35, 131.6, 128.9, 127.3, 122.0, 118.9, 61.1, 14.6. HRMS (m/z): $[M+H]^+$, calcd for $C_{18}H_{14}Cl_2N_3O_4$, 406.0356; found, 406.0376.

2-(3,4-Dichlorophenyl)-N-(thiazol-2-yl)isonicotinamide (16). This compound was prepared by the general procedures A, C and D affording 16 as a light yellow-colored powder (103 mg, 20%). $^1$H NMR (400 MHz, DMSO-$d_6$) δ ppm 13.02 (br s, 1H), 8.87 (d, J=5.4 Hz, 1H), 8.59-8.71 (m, 1H), 8.40 (d, J=2.2 Hz, 1H), 8.18 (dd, J=2.2, 8.6 Hz, 1H), 7.93 (dd, J=1.6, 5.0 Hz, 1H), 7.79 (d, J=8.6 Hz, 1H), 7.62 (d, J=3.4 Hz, 1H), 7.36 (d, J=3.4 Hz, 1H). $^{13}$C NMR (101 MHz, DMSO-$d_6$) δ ppm 163.9, 159.0, 154.7, 151.1, 141.1, 139.0, 138.0, 132.8, 132.3, 131.5, 128.8, 127.2, 122.0, 118.8, 114.9. HRMS (m/z): $[M+H]^+$, calcd for $C_{15}H_{10}Cl_2N_3OS$, 349.9916; found, 349.9933.

2-(3,4-Dichlorophenyl)-N-(1H-imidazol-2-yl)isonicotinamide (17). This compound was prepared by the general procedures A, C, and D affording 17 as a colorless powder (146 mg, 29%). $^1$H NMR (400 MHz, DMSO-$d_6$) δ ppm 12.09 (br s, 2H), 8.82 (d, J=4.9 Hz, 1H), 8.56 (s, 1H), 8.37 (d, J=2.2 Hz, 1H), 8.13 (dd, J=2.2, 8.6 Hz, 1H), 7.93 (dd, J=1.6, 5.0 Hz, 1H), 7.81 (d, J=8.3 Hz, 1H), 6.89 (s, 2H). $^{13}$C NMR (101 MHz, DMSO-$d_6$) δ ppm 166.8, 154.4, 150.8, 145.8, 145.0, 139.5, 132.5, 132.3, 131.6, 128.8, 127.1, 122.2, 119.0, 116.4. HRMS (m/z): $[M+H]^+$, calcd for $C_{15}H_{11}Cl_2N_4O$, 333.0304; found, 333.0301.

2-(3,4-Dichlorophenyl)-N-(isoxazol-3-yl)isonicotinamide (18). This compound was prepared by the general procedures A, C and D affording 18 as a colorless powder (120 mg, 24%). $^1$H NMR (400 MHz, DMSO-$d_6$) δ ppm 11.85 (s, 1H), 8.93 (d, J=1.7 Hz, 1H), 8.88 (dd, J=0.6, 5.0 Hz, 1H), 8.54-8.66 (m, 1H), 8.42 (d, J=2.2 Hz, 1H), 8.19 (dd, J=2.2, 8.6 Hz, 1H), 7.89 (dd, J=1.6, 5.0 Hz, 1H), 7.81 (d, J=8.6 Hz, 1H), 7.12 (d, J=1.7 Hz, 1H). $^{13}$C NMR (101 MHz, DMSO-$d_6$) δ ppm 164.1, 161.0, 158.2, 154.7, 151.1, 141.9, 139.0, 132.8, 132.3, 131.6, 128.9, 127.3, 122.0, 118.8, 100.1. HRMS (m/z): $[M+H]^+$, calcd for $C_{15}H_{10}Cl_2N_3O_2$, 334.0145; found, 334.0136.

2-(3,4-Dichlorophenyl)-N-(5-methyl-1,3,4-oxadiazol-2-yl)isonicotinamide (19). This compound was prepared by the general procedures A, C and D affording 19 as a colorless powder (129 mg, 25%). $^1$H NMR (400 MHz, DMSO-$d_6$) δ ppm 13.90 (br s, 1H), 8.82-8.92 (m, 1H), 8.38 (d, J=2.2 Hz, 2H), 8.14 (dd, J=2.2, 8.3 Hz, 1H), 7.84 (dd, J=1.5, 4.9 Hz, 1H), 7.77 (d, J=8.3 Hz, 1H), 2.19-2.25 (m, 3H). $^{13}$C NMR (101 MHz, DMSO-$d_6$) δ ppm 168.0, 165.5, 156.0, 153.9, 150.2, 139.4, 137.9, 131.6, 131.3, 130.5, 127.9, 126.2, 121.8, 118.9, 10.2. HRMS (m/z): $[M+H]^+$, calcd for $C_{15}H_{11}Cl_2N_4O_2$, 349.0254; found, 349.0249.

2-(3,4-Dichlorophenyl)-N-methylisonicotinamide (20). Compound 8a (200 mg, 0.7 mmol) was stirred in thionyl chloride (3 mL) at reflux overnight. The solvent was removed under vacuo. The residual solid was dissolved in 5 mL of a $MeNH_2$ solution 2.0 M in THF and stirred at room temperature for 4 h. The THF was removed under vacuo. The solid was dissolved in EtOAc (20 mL) and washed with a saturated solution of $NaHCO_3$ (10 mL) and brine (10 mL). The organic layer was dried ($Na_2SO_4$) and evaporated under reduced pressure affording 20 as a colorless powder (168 mg, 80%). $^1$H NMR (400 MHz, DMSO-$d_6$) δ ppm 8.90 (br s, 1H), 8.79-8.83 (m, 1H), 8.33-8.42 (m, 2H), 8.09-8.20 (m, 1H), 7.80 (d, J=8.6 Hz, 1H), 7.76 (dd, J=1.5, 4.9 Hz, 1H), 2.85 (d, J=4.7 Hz, 3H). $^{13}$C NMR (101 MHz, DMSO-$d_6$) δ ppm 165.2, 154.5, 150.9, 143.2, 139.2, 132.6, 132.3, 131.6, 128.8, 127.2, 121.5, 118.2, 26.7. HRMS (m/z): $[M-H]^-$, calcd for $C_{13}H_{11}Cl_2N_2O$, 281.0243; found, 281.0249.

N-(benzo[d]oxazol-2-yl)-2-(3,4-dichlorophenyl)isonicotinamide (21). This compound was prepared by the general procedures A, C, and D affording 21 as a colorless powder (253 mg, 13%). $^1$H NMR (400 MHz, DMSO-$d_6$) δ ppm 12.55-12.84 (m, 1H), 8.89 (d, J=4.9 Hz, 1H), 8.56 (s, 1H), 8.32-8.48 (m, 1H), 8.09-8.24 (m, 1H), 7.93 (d, J=5.6 Hz, 1H), 7.80 (d, J=8.3 Hz, 1H), 7.65-7.73 (m, 1H), 7.56-7.65 (m, 1H), 7.27-7.45 (m, 2H). $^{13}$C NMR (101 MHz, DMSO-$d_6$) δ ppm 157.3, 154.7, 151.1, 146.9, 142.8, 139.1, 132.7, 132.3, 131.6, 128.9, 127.2, 125.4, 124.6, 123.9, 122.2, 119.2, 115.7, 110.8, 108.8. HRMS (m/z): $[M+H]^+$, calcd for $C_{19}H_{12}Cl_2N_3O_2$, 384.0301; found, 384.0317.

2-(3,4-Dichlorophenyl)-N-(oxazolo[4,5-b]pyridin-2-yl) isonicotinamide (22). This compound was prepared by the general procedures A, C, and D affording 22 as a colorless powder (72 mg, 12%). $^1$H NMR (400 MHz, DMSO-$d_6$) δ ppm 12.76 (br s, 1H), 8.89 (d, J=4.9 Hz, 1H), 8.58 (s, 1H), 8.42 (d, J=2.2 Hz, 1H), 8.38 (dd, J=1.6, 5.0 Hz, 1H), 8.18 (dd, J=2.2, 8.6 Hz, 1H), 8.04 (dd, J=1.0, 7.8 Hz, 1H), 7.92 (dd, J=1.6, 5.0 Hz, 1H), 7.83 (d, J=8.3 Hz, 1H), 7.29 (dd, J=5.1, 8.1 Hz, 1H). $^{13}$C NMR (101 MHz, DMSO-$d_6$) δ ppm 154.6, 151.0, 145.7, 140.7, 139.2, 132.7, 132.4, 131.7, 128.9, 127.3, 122.3, 119.3, 119.2, 117.7. HRMS (m/z): $[M+H]^+$, calcd for $C_{18}H_{11}Cl_2N_4O_2$, 385.0254; found, 385.0241.

Ethyl 2-(2-(3,4-dichlorophenyl)isonicotinamido)oxazole-5-carboxylate (23). This compound was prepared by the general procedures A, C, and D affording 23 as a colorless powder (500 mg, 33%). $^1$H NMR (400 MHz, DMSO-$d_6$) δ ppm 12.40-12.68 (m, 1H), 8.90 (d, J=5.6 Hz, 1H), 8.51-8.61 (m, 1H), 8.42 (d, J=2.2 Hz, 1H), 8.18 (dd, J=2.2, 8.3 Hz, 1H), 7.96-8.07 (m, 1H), 7.88 (dd, J=1.6, 5.0 Hz, 1H), 7.83 (d, J=8.6 Hz, 1H), 4.33 (q, J=7.1 Hz, 2H), 1.31 (t, J=7.1 Hz, 3H). $^{13}$C NMR (101 MHz, DMSO-$d_6$) δ ppm 169.0, 168.5, 158.3, 153.9, 150.4, 149.4, 139.9, 137.1, 133.7, 132.2, 132.1, 131.6, 128.6, 127.0, 122.6, 119.5, 60.4, 14.8. HRMS (m/z): $[M+H]^+$, calcd for $C_{18}H_{14}Cl_2N_3O_4$, 406.0356; found, 406.0346.

2-(2-(3,4-Dichlorophenyl)isonicotinamido)oxazole-5-carboxylic acid (24). To a solution of LiOH (1.08 g, 25.8 mmol) in 48 mL of 1:1 THF/water, was added 23 (7 g, 17.2 mmol). The reaction mixture was stirred at 60° C. for 3 h. The solvent was evaporated under reduced pressure. The residual solid was taken up in water (25 mL). Concentrated HCl was added dropwise until pH 2, causing the precipitation of 24, which was filtered and dried under reduced pressure to afford a yellow-colored powder (5.51 g, 85%). $^1$H NMR (400 MHz, $CDCl_3$) δ ppm 13.57 (br s, 1H), 12.46 (br s, 1H), 8.90 (d, J=5.1 Hz, 1H), 8.56 (s, 1H), 8.41 (d, J=2.2 Hz, 1H), 8.18 (dd, J=2.1, 8.4 Hz, 1H), 7.91 (s, 1H), 7.88 (dd, J=1.6, 5.0 Hz, 1H), 7.83 (d, J=8.6 Hz, 1H). $^{13}$C NMR (101 MHz, $CDCl_3$) δ ppm 158.7, 154.7, 151.1, 139.0, 132.8, 132.3, 131.6, 128.9, 127.3, 122.1, 119.1. HRMS (m/z): $[M+H]^+$, calcd for $C_{16}H_{10}Cl_2N_3O_4$, 378.0043; found, 378.0056.

Hept-6-yn-1-yl 2-(2-(3,4-dichlorophenyl)isonicotinamido)oxazole-5-carboxylate (25). 1-Ethyl-3-(3-dimethylaminopropyl)carbodiimide hydrochloride (200 mg, 0.6 mmol) was added to a solution of 24 (200 mg, 0.5 mmol) and 4-dimethylaminopyridine (71 mg, 0.6 mmol) in dry pyridine (5 mL) in an oven-dried flask, chilled to ice-water temperature under a nitrogen atmosphere. After 5 min, 6-heptyn-1-ol (60 mg, 0.5 mmol) was added via a syringe. The solution was allowed to warm to room temperature overnight. The reaction mixture was concentrated under reduced pressure. EtOAc (25 mL) was added and the organic solution was washed with water (2×25 mL) and brine (25 mL). The organic layer was dried ($Na_2SO_4$) and evaporated under reduced pressure affording the crude material, which was purified by silica chromatography using gradient elution from 9:1 hexanes/EtOAc to EtOAc, affording 25 as a light yellow-colored powder (62 mg, 25%). $^1$H NMR (400 MHz, $CDCl_3$) δ ppm 11.22 (br s, 1H), 8.89 (d, J=5.4 Hz, 1H), 8.48 (br s, 1H), 8.21 (d, J=2.2 Hz, 1H), 8.03 (br s, 1H), 7.97 (dd, J=2.2, 8.6 Hz, 1H), 7.70 (s, 1H), 7.50-7.58 (m, 1H), 4.33 (t, J=6.7 Hz, 2H), 2.19-2.27 (m, 2H), 1.97 (t, J=2.7 Hz, 1H), 1.77 (quin, J=7.0 Hz, 2H), 1.47-1.64 (m, 4H). $^{13}$C NMR (101 MHz, $CDCl_3$) δ ppm 157.1, 155.8, 150.4, 137.7, 134.1, 133.3, 130.9, 129.0, 126.2, 120.9, 118.9, 84.1, 68.6, 65.8, 28.1, 27.9, 24.9, 18.3. HRMS (m/z): $[M+H]^+$, calcd for $C_{23}H_{20}Cl_2N_3O_4$, 472.0825; found, 472.0806.

6-Hydroxyhexyl 2-(2-(3,4-dichlorophenyl)isonicotinamido)oxazole-5-carboxylate (26). This compound was prepared by the same procedure for 24, affording 26 as a colorless powder (225 mg, 44%). $^1$H NMR (400 MHz, DMSO-$d_6$) δ ppm 12.52 (br s, 1H), 8.85-8.93 (m, 1H), 8.49-8.60 (m, 1H), 8.34-8.46 (m, 1H), 8.10-8.25 (m, 1H), 7.95-8.08 (m, 1H), 7.76-7.92 (m, 2H), 4.37 (br s, 1H), 4.22-4.33 (m, 2H), 3.39 (t, J=6.4 Hz, 2H), 1.61-1.81 (m, 2H), 1.32-1.48 (m, 6H). $^{13}$C NMR (101 MHz, DMSO-$d_6$) δ ppm 157.5, 154.8, 151.1, 139.0, 132.8, 132.4, 131.7, 128.9, 127.3, 122.1, 119.1, 65.4, 61.1, 32.9, 28.7, 25.7, 25.6. HRMS (m/z): $[M+H]^+$, calcd for $C_{22}H_{22}Cl_2N_3O_5$, 478.0931; found, 478.0945.

6-((Tert-butoxycarbonyl)amino)hexyl 2-(2-(3,4-dichlorophenyl)isonicotinamido) oxazole-5-carboxylate (27). This compound was prepared by the same procedure for 24, affording 27 as a light yellow-colored powder (653 mg, 43%). $^1$H NMR (400 MHz, DMSO-$d_6$) δ ppm 8.69-8.78 (m, 1H), 8.49 (t, J=1.22 Hz, 1H), 8.30 (d, J=2.2 Hz, 1H), 8.06 (dd, J=2.2, 8.6 Hz, 1H), 7.96 (dd, J=1.5, 4.9 Hz, 1H), 7.78 (d, J=8.3 Hz, 1H), 7.61 (s, 1H), 6.75-6.85 (m, 1H), 4.19 (t, J=6.72 Hz, 2H), 2.91 (q, J=6.8 Hz, 2H), 1.58-1.71 (m, 2H), 1.21-1.45 (m, 15H). $^{13}$C NMR (101 MHz, DMSO-$d_6$) δ ppm 167.7, 167.3, 157.3, 155.0, 152.9, 149.3, 148.3, 138.8, 136.2, 132.7, 131.2, 131.0, 130.5, 127.6, 125.9, 121.6, 118.4, 76.7, 63.2, 28.8, 27.7, 25.3, 24.5. HRMS (m/z): $[M+H]^+$, calcd for $C_{27}H_{31}Cl_2N_4O_6$, 577.1615; found, 577.1629.

(2-(3,4-Dichlorophenyl)isonicotinamido)-N,N-dimethyloxazole-5-carboxamide (28). This compound was prepared starting from 8a and 2-amino-N,N-dimethyloxazole-carboxamide, following the general procedure D affording 28 as a yellow-colored powder (162 mg, 11%). $^1$H NMR (400 MHz, DMSO-$d_6$) δ ppm 12.36 (br s, 1H), 8.89 (d, J=5.1 Hz, 1H), 8.56 (s, 1H), 8.35-8.50 (m, 1H), 8.13-8.27 (m, 1H), 7.88 (dd, J=1.3, 5.0 Hz, 1H), 7.83 (d, J=8.6 Hz, 1H), 7.73 (s, 1H), 3.16-3.31 (m, 3H), 2.90-3.11 (m, 3H). $^{13}$C NMR (101 MHz, DMSO-$d_6$) δ ppm 157.8, 154.8, 151.1, 139.0, 132.8, 132.4, 131.6, 128.9, 127.3, 122.1, 119.1. HRMS (m/z): $[M+H]^+$, calcd for $C_{18}H_{15}Cl_2N_4O_3$, 405.0516; found, 405.0512.

2-(3,4-Dichlorophenyl)-N-(5-(morpholine-4-carbonyl) oxazol-2-yl)isonicotinamide (29). This compound was prepared by the same procedure for 28, affording 29 as a light yellow-colored powder (200 mg, 15%). $^1$H NMR (400 MHz, DMSO-$d_6$) δ ppm 12.43 (br s, 1H), 8.89 (d, J=5.1 Hz, 1H), 8.54 (s, 1H), 8.40 (d, J=2.2 Hz, 1H), 8.17 (dd, J=2.2, 8.6 Hz, 1H), 7.88 (dd, J=1.6, 5.0 Hz, 1H), 7.82 (d, J=8.3 Hz, 1H), 7.75 (s, 1H), 3.72 (br s, 4H), 3.68 (br s, 4H). $^{13}$C NMR (101 MHz, DMSO-$d_6$) δ ppm 156.9, 154.8, 151.1, 141.9, 140.6, 139.0, 132.8, 132.4, 131.6, 128.9, 127.3, 122.1, 119.1, 66.6. HRMS (m/z): $[M+H]^+$, calcd for $C_{20}H_{17}Cl_2N_4O_4$, 447.0621; found, 447.0614.

Tert-butyl 4-(2-(2-(3,4-Dichlorophenyl)isonicotinamido) oxazole-5-carbonyl) piperazine-1-carboxylate (30). This compound was prepared by the same procedure for 28, affording 30 as a colorless powder (345 mg, 20%). $^1$H NMR (400 MHz, DMSO-$d_6$) δ ppm 12.42 (br s, 1H), 8.86 (d, J=5.1 Hz, 1H), 8.52 (s, 1H), 8.38 (s, 1H), 8.15 (d, J=8.3 Hz, 1H), 7.86 (d, J=5.1 Hz, 1H), 7.79 (d, J=8.6 Hz, 1H), 7.74 (s, 1H), 3.70 (br s, 4H), 3.43 (br s, 4H), 1.42 (s, 9H). $^{13}$C NMR (101 MHz, DMSO-$d_6$) δ ppm 156.9, 154.7, 154.2, 151.1, 141.6, 140.7, 138.9, 132.8, 132.3, 131.6, 128.9, 127.2, 122.1, 119.0, 79.7, 28.5. HRMS (m/z): $[M+H]^+$, calcd for $C_{25}H_{26}Cl_2N_5O_5$, 546.1306; found, 546.1313.

2-(3,4-Dichlorophenyl)-N-(5-(piperazine-1-carbonyl) oxazol-2-yl)isonicotinamide dihydrochloride (31). Compound 30 (50 mg, 0.1 mmol) was added to 5 mL of 1 M HCl in dioxane and stirred overnight. The solvent was then removed under vacuo and the solid was triturated with $Et_2O$ (2×5 mL), affording 31 as a yellow-colored powder (38 mg, 82%). $^1$H NMR (400 MHz, DMSO-$d_6$) δ ppm 9.53 (br s, 1H), 8.90 (d, J=5.1 Hz, 1H), 8.60 (s, 1H), 8.44 (d, J=2.2 Hz, 1H), 8.20 (dd, J=2.1, 8.4 Hz, 1H), 7.87-7.93 (m, 1H), 7.79-7.87 (m, 2H), 5.44 (br s, 2H), 3.96 (br s, 4H), 3.63-3.74 (m, 2H), 3.42-3.54 (m, 2H), 3.39 (s, 1H). $^{13}$C NMR (101 MHz, DMSO-$d_6$) δ ppm 157.3, 154.7, 151.1, 146.9, 142.9, 139.1, 132.7, 132.3, 131.6, 128.9, 127.2, 125.4, 124.6, 122.2, 119.2, 117.3, 110.8, 72.6, 71.0, 63.3, 60.6. HRMS (m/z): $[M+H]^+$, calcd for $C_{20}H_{18}Cl_2N_5O_3$, 446.0781; found, 446.0785.

2-(4-Chlorophenyl)-N-(oxazol-2-yl)isonicotinamide (32). This compound was prepared by the general procedures A, C, and D affording 32 as a colorless powder (159 mg, 35%). $^1$H NMR (400 MHz, DMSO-$d_6$) δ ppm 12.00 (br s, 1H), 8.86 (d, J=5.1 Hz, 1H), 8.47 (s, 1H), 8.20 (d, J=8.3 Hz, 2H), 7.98 (br s, 1H), 7.84 (d, J=4.3 Hz, 1H), 7.60 (d, J=8.7 Hz, 2H), 7.25 (s, 1H). $^{13}$C NMR (101 MHz, DMSO-$d_6$) δ ppm 156.3, 151.2, 137.7, 135.2, 129.7, 129.2, 121.7, 118.9. HRMS (m/z): $[M+H]^+$, calcd for $C_{15}H_{11}C_1N_3O_2$, 300.0534; found, 300.0523.

2-(3-Chlorophenyl)-N-(oxazol-2-yl)isonicotinamide (33). This compound was prepared by the general procedures A, C, and D affording 33 as a colorless powder (133 mg, 30%). $^1$H NMR (400 MHz, DMSO-$d_6$) δ ppm 11.98 (br s, 1H), 8.88 (d, J=4.9 Hz, 1H), 8.50 (s, 1H), 8.22 (s, 1H), 8.15 (d, J=5.9 Hz, 1H), 8.00 (br s, 1H), 7.83-7.91 (m, 1H), 7.51-7.63 (m, 2H), 7.26 (br s, 1H). $^{13}$C NMR (101 MHz, DMSO-$d_6$) δ ppm 155.7, 151.0, 140.6, 134.3, 131.3, 129.8, 126.9, 125.8, 121.9, 119.0. HRMS (m/z): $[M+H]^+$, calcd for $C_{15}H_{11}C_1N_3O_2$, 300.0534; found, 300.0528.

2-(2-Chlorophenyl)-N-(oxazol-2-yl)isonicotinamide (34). This compound was prepared by the general procedures A, C, and D affording 34 as an off-white-colored powder (84 mg, 19%). $^1$H NMR (400 MHz, DMSO-$d_6$) δ ppm 11.96 (br s, 1H), 8.89 (d, J=5.4 Hz, 1H), 8.15 (br s, 1H), 7.80-8.04 (m, 2H), 7.56-7.75 (m, 2H), 7.44-7.56 (m, 2H), 7.25 (br s, 1H). $^{13}$C NMR (101 MHz, DMSO-$d_6$) δ ppm 157.5, 150.7, 138.8, 132.2, 131.6, 130.9, 130.5, 127.9, 123.0, 121.4. HRMS (m/z): $[M+H]^+$, calcd for $C_{15}H_{11}ClN_3O_2$, 300.0534; found, 300.0524.

2-(3,4-Difluorophenyl)-N-(oxazol-2-yl)isonicotinamide (35). This compound was prepared by the general procedures A, C, and D affording 35 as a colorless powder (164 mg, 36%). $^1$H NMR (400 MHz, DMSO-$d_6$) δ ppm 12.00 (br s, 1H), 8.87 (d, J=4.9 Hz, 1H), 8.50 (s, 1H), 8.15-8.25 (m, 1H), 7.95-8.11 (m, 2H), 7.85 (d, J=5.4 Hz, 1H), 7.56-7.69 (m, 1H), 7.26 (s, 1H). $^{13}$C NMR (101 MHz, DMSO-$d_6$) δ 166.6, 155.1, 151.0, 150.6 (dd, $J_{CF}$=53.1, 234.3 Hz, 1C), 141.5 (dd, $J_{CF}$=7.3, 40.2 Hz, 1C), 137.3, 136.2, 127.3, 124.2 (dd, $J_{CF}$=2.9, 6.4 Hz, 1C), 121.7, 119.7, 118.8, 117.4 (dd, $J_{CF}$=18.1, 231.5 Hz, 1C), 116.2. $^{19}$F NMR (376 MHz, DMSO-$d_6$) δ ppm −137.93, −137.99. HRMS (m/z): $[M+H]^+$, calcd for $C_{15}H_{10}F_2N_3O_2$, 302.0736; found, 302.0741.

2-(4-Fluorophenyl)-N-(oxazol-2-yl)isonicotinamide (36). This compound was prepared by the general procedures A, C, and D affording 36 as a colorless powder (128 mg, 30%). $^1$H NMR (400 MHz, DMSO-$d_6$) δ ppm 12.03 (br s, 1H), 8.85 (d, J=4.9 Hz, 1H), 8.45 (s, 1H), 8.23 (dd, J=5.6, 8.56 Hz, 2H), 8.00 (br s, 1H), 7.82 (d, J=5.1 Hz, 1H), 7.38 (t, J=8.9 Hz, 2H), 7.26 (s, 1H). $^{13}$C NMR (101 MHz, DMSO-$d_6$) δ ppm 164.0, 163.6 (d, $J_{CF}$=246.7 Hz, 1C), 156.4, 153.4, 150.9, 141.6, 137.5, 135.1, 129.5 (d, $J_{CF}$=8.6 Hz, 2C), 127.4, 121.1, 118.5, 116.3 (d, $J_{CF}$=21.5 Hz, 2C). $^{19}$F NMR (376 MHz, DMSO-$d_6$) δ ppm −112.37. HRMS (m/z): $[M+H]^+$, calcd for $C_{15}H_{11}FN_3O_2$, 284.0830; found, 284.0843.

2-(3-Fluorophenyl)-N-(oxazol-2-yl)isonicotinamide (37). This compound was prepared by the general procedures A, C, and D affording 37 as a gray powder (142 mg, 33%). $^1$H NMR (400 MHz, DMF-$d_7$) 6 ppm 12.18 (br s, 1H), 8.94 (d, J=5.1 Hz, 1H), 8.64 (s, 1H), 8.12 (d, J=8.1 Hz, 1H), 7.95-8.08 (m, 3H), 7.57-7.69 (m, 1H), 7.21-7.43 (m, 2H). $^{13}$C NMR (101 MHz, DMF-$d_7$) 6 ppm 164.6, 156.0, 150.7, 141.2 (d, $J_{CF}$=8.7 Hz, 1C), 131.0 (d, $J_{CF}$=8.5 Hz, 1C), 122.89, 122.86, 121.5, 118.6, 116.3 (d, $J_{CF}$=21.6 Hz, 1C), 113.5 (d, $J_{CF}$=23.3 Hz, 1C), 100.0. $^{19}$F NMR (376 MHz, DMSO-$d_6$) δ ppm −112.73. HRMS (m/z): $[M+H]^+$, calcd for $C_{15}H_{11}FN_3O_2$, 284.0830; found, 284.0830.

2-(2-Fluorophenyl)-N-(oxazol-2-yl)isonicotinamide (38). This compound was prepared by the general procedures A, C, and D affording 38 as a slightly pink-colored powder (143 mg, 33%). $^1$H NMR (400 MHz, DMSO-$d_6$) δ ppm 12.06 (br s, 1H), 8.91 (d, J=4.9 Hz, 1H), 8.29 (br s, 1H), 7.94-8.04 (m, 2H), 7.91 (d, J=4.7 Hz, 1H), 7.49-7.58 (m, 1H), 7.33-7.44 (m, 2H), 7.26 (br s, 1H). $^{13}$C NMR (101 MHz, DMSO-$d_6$) δ ppm 160.3 (d, $J_{CF}$=248.9 Hz, 1C), 153.9, 151.0, 131.8 (d, $J_{CF}$=8.5 Hz, 1C), 131.4 (d, $J_{CF}$=2.5 Hz, 1C), 126.9 (d, $J_{CF}$=11.2 Hz, 1C), 125.4 (d, $J_{CF}$=3.4 Hz, 1C), 122.6 (d, $J_{CF}$=7.7 Hz, 1C), 121.4, 116.9 (d, $J_{CF}$=22.6 Hz, 1C). $^{19}$F NMR (376 MHz, DMSO-$d_6$) δ ppm −117.19. HRMS (m/z): $[M+H]^+$, calcd for $C_{15}H_{11}FN_3O_2$, 284.0830; found, 284.0826.

2-(4-Chloro-3-fluorophenyl)-N-(oxazol-2-yl)isonicotinamide (39). This compound was prepared by the general procedures A, C, and D affording 39 as a colorless powder (180 mg, 38%). $^1$H NMR (400 MHz, DMSO-$d_6$) δ ppm 12.03 (br s, 1H), 8.87 (d, J=5.1 Hz, 1H), 8.52 (s, 1H), 8.17 (d, J=11.0 Hz, 1H), 8.06 (d, J=8.07 Hz, 1H), 7.98 (br s, 1H), 7.79-7.93 (m, 1H), 7.76 (t, J=8.0 Hz, 1H), 7.25 (br s, 1H). $^{13}$C NMR (101 MHz, DMSO-$d_6$) δ ppm 158.1 (d, $J_{CF}$=246.1 Hz, 1C), 154.9, 151.1, 139.7 (d, $J_{CF}$=6.9 Hz, 1C), 131.6, 124.3 (d, $J_{CF}$=3.2 Hz, 1C), 122.1, 121.2 (d, $J_{CF}$=17.7 Hz, 1C), 119.0, 115.3 (d, $J_{CF}$=22.5 Hz, 1C). $^{19}$F NMR (376 MHz, DMSO-$d_6$) δ ppm −115.71. HRMS (m/z): $[M+H]^+$, calcd for $C_{15}H_{10}ClFN_3O_2$, 318.0440; found, 318.0439.

2-(3-Chloro-4-fluorophenyl)-N-(oxazol-2-yl)isonicotinamide (40). This compound was prepared by the general procedures A, C, and D affording 40 as a colorless powder (123 mg, 26%). $^1$H NMR (400 MHz, DMSO-$d_6$) δ ppm 12.05 (br s, 1H), 8.86 (d, J=4.9 Hz, 1H), 8.50 (s, 1H), 8.35 (d, J=6.4 Hz, 1H), 8.19 (br s, 1H), 7.99 (br s, 1H), 7.86 (d, J=4.2 Hz, 1H), 7.58 (t, J=8.8 Hz, 1H), 7.27 (s, 1H). $^{13}$C NMR (101 MHz, DMSO-$d_6$) δ ppm 13C NMR (101 MHz, DMSO) δ 158.5 (d, $J_{CF}$=249.5 Hz, 1C), 154.9, 151.0, 136.3 (d, $J_{CF}$=3.4 Hz, 1C), 129.2, 127.9 (d, $J_{CF}$=7.8 Hz, 1C), 121.7, 120.7 (d, $J_{CF}$=17.9 Hz, 1C), 118.8, 117.8 (d, $J_{CF}$=21.2

Hz, 1C). $^{19}$F NMR (376 MHz, DMSO-$d_6$) δ ppm −115.59. HRMS (m/z): $[M+H]^+$, calcd for $C_{15}H_{10}ClFN_3O_2$, 318.0440; found, 318.0455.

2-(3,5-Dichlorophenyl)-N-(oxazol-2-yl)isonicotinamide (41). This compound was prepared by the general procedures A, C and D affording 41 as a colorless powder (64 mg, 17%). $^1$H NMR (400 MHz, DMSO-$d_6$) δ ppm 12.03 (br s, 1H), 8.89 (d, J=4.9 Hz, 1H), 8.55 (s, 1H), 8.21 (d, J=2.0 Hz, 2H), 8.01 (s, 1H), 7.90 (dd, J=1.5, 4.9 Hz, 1H), 7.75 (t, J=2.0 Hz, 1H), 7.26 (s, 1H). $^{13}$C NMR (101 MHz, DMSO-$d_6$) δ ppm 154.3, 151.1, 141.9, 135.3, 129.30, 129.25, 126.7, 125.8, 122.5, 119.3, 100.0. HRMS (m/z): $[M+H]^+$, calcd for $C_{15}H_{10}Cl_2N_3O_2$, 334.0145; found, 334.0143.

2-(3,5-Difluorophenyl)-N-(oxazol-2-yl)isonicotinamide (42). This compound was prepared by the general procedures A, C, and D affording 42 as a colorless powder (96 mg, 13%). $^1$H NMR (400 MHz, DMSO-$d_6$) δ ppm 11.99 (br s, 1H), 8.89 (d, J=5.1 Hz, 1H), 8.54 (s, 1H), 7.99 (br s, 1H), 7.79-7.95 (m, 3H), 7.40 (t, J=9.1 Hz, 1H), 7.26 (s, 1H). $^{13}$C NMR (101 MHz, DMSO-$d_6$) δ ppm 163.4 (dd, $J_{CF}$=245.7, 13.3 Hz, 2C), 154.6, 151.1, 142.2 (dd, $J_{CF}$=18.3, 9.2 Hz, 1C), 122.5, 119.2, 110.3 (d, $J_{CF}$=19.2, 7.4 Hz, 1C), 105.3 (t, $J_{CF}$=26.0 Hz, 1C). $^{19}$F NMR (376 MHz, DMSO-$d_6$) δ ppm −109.11. HRMS (m/z): $[M+H]^+$, calcd for $C_{15}H_{10}F_2N_3O_2$, 302.0736; found, 302.0747.

2-(3-Chloro-5-fluorophenyl)-N-(oxazol-2-yl)isonicotinamide (43). This compound was prepared by the general procedures A, C, and D affording 43 as a colorless powder (253 mg, 24%). $^1$H NMR (400 MHz, DMSO-$d_6$) δ ppm 12.03 (br s, 1H), 8.89 (d, J=5.1 Hz, 1H), 8.55 (s, 1H), 8.11 (s, 1H), 7.94-8.04 (m, 2H), 7.90 (d, J=4.2 Hz, 1H), 7.59 (td, J=2.2, 8.6 Hz, 1H), 7.27 (s, 1H). $^{13}$C NMR (101 MHz, DMSO-$d_6$) δ ppm 163.2 (d, $J_{CF}$=247.0 Hz, 1C), 154.4 (d, $J_{CF}$=2.9 Hz, 1C), 151.1, 142.2 (d, $J_{CF}$=9.0 Hz, 1C), 135.2 (d, $J_{CF}$=11.1 Hz, 1C), 123.3 (d, $J_{CF}$=2.8 Hz, 1C), 122.5, 119.3, 117.3 (d, $J_{CF}$=25.3 Hz, 1C), 113.0 (d, $J_{CF}$=23.2 Hz, 1C). $^{19}$F NMR (376 MHz, DMSO-$d_6$) δ ppm −110.09. HRMS (m/z): $[M+H]^+$, calcd for $C_{15}H_{10}ClFN_3O_2$, 318.0440; found, 318.0439.

N-(Oxazol-2-yl)-2-(4-(trifluoromethyl)phenyl)isonicotinamide (44). This compound was prepared by the general procedures A, C and D affording 44 as a light pink-colored powder (182 mg, 36%). $^1$H NMR (400 MHz, DMSO-$d_6$) δ ppm 12.05 (br s, 1H), 8.87-8.97 (m, 1H), 8.57 (s, 1H), 8.40 (d, J=8.3 Hz, 2H), 8.02 (br s, 1H), 7.92 (d, J=8.6 Hz, 3H), 7.27 (br s, 1H). $^{13}$C NMR (101 MHz, DMSO-$d_6$) δ ppm 165.5, 154.7, 150.4, 150.1, 141.3, 139.1, 129.0 (q, $J_{CF}$=32.0 Hz, 1C), 126.9, 125.2 (q, $J_{CF}$=3.6 Hz, 2C), 123.7 (q, $J_{CF}$=272.1 Hz, 1C), 121.9, 121.1, 119.1, 118.3. $^{19}$F NMR (376 MHz, DMSO-$d_6$) δ ppm −61.08. HRMS (m/z): $[M+H]^+$, calcd for $C_{16}H_{11}F_3N_3O_2$, 334.0798; found, 334.0802.

N-(Oxazol-2-yl)-2-(3-(trifluoromethyl)phenyl)isonicotinamide (45). This compound was prepared by the general procedures A, C, and D affording 45 as a colorless powder (147 mg, 29%). $^1$H NMR (400 MHz, DMSO-$d_6$) δ ppm 12.11 (br s, 1H), 8.92 (d, J=4.9 Hz, 1H), 8.58 (s, 1H), 8.42-8.54 (m, 2H), 8.01 (br s, 1H), 7.73-7.94 (m, 3H), 7.28 (s, 1H). $^{13}$C NMR (101 MHz, DMSO-$d_6$) δ ppm 160.1, 155.6, 151.1, 139.5, 131.2, 130.6, 130.2 (q, $J_{CF}$=31.8 Hz, 1C), 126.5 (q, $J_{CF}$=3.6 Hz, 1C), 124.7 (q, $J_{CF}$=272.3 Hz, 1C), 123.6 (q, $J_{CF}$=3.9 Hz, 1C), 122.1, 119.1. $^{19}$F NMR (376 MHz, DMSO-$d_6$) δ ppm −61.11. HRMS (m/z): $[M+H]^+$, calcd for $C_{16}H_{11}F_3N_3O_2$, 334.0798; found, 334.0794.

N-(Oxazol-2-yl)-2-(4-(trifluoromethoxy)phenyl)isonicotinamide (46). This compound was prepared by the general procedures A, C, and D affording 46 as a colorless powder (166 mg, 32%). $^1$H NMR (400 MHz, DMSO-$d_6$) δ ppm 12.03 (br s, 1H), 8.88 (d, J=5.1 Hz, 1H), 8.44-8.56 (m, 1H), 8.25-8.37 (m, 2H), 8.00 (br s, 1H), 7.79-7.93 (m, 1H), 7.46-7.63 (m, 2H), 7.26 (br s, 1H). $^{13}$C NMR (101 MHz, DMSO-$d_6$) δ ppm 154.9, 150.0, 148.7, 136.7, 128.2, 120.7, 120.5, 119.5 (q, $J_{CF}$=256.8 Hz, 1C), 117.8. $^{19}$F NMR (376 MHz, DMSO-$d_6$) δ ppm −56.65. FIRMS (m/z): $[M+H]^+$, calcd for $C_{16}H_{11}F_3N_3O_3$, 350.0747; found, 350.0755.

N-(Oxazol-2-yl)-2-(3-(trifluoromethoxy)phenyl)isonicotinamide (47). This compound was prepared by the general procedures A, C, and D affording 47 as a light pink-colored powder (190 mg, 36%). $^1$H NMR (400 MHz, DMSO-$d_6$) δ ppm 12.11 (br s, 1H), 8.81-8.99 (m, 1H), 8.54 (br s, 1H), 8.23 (d, J=8.3 Hz, 1H), 8.15 (br s, 1H), 8.01 (br s, 1H), 7.81-7.94 (m, 1H), 7.60-7.79 (m, 1H), 7.44-7.59 (m, 1H), 7.22-7.38 (m, 1H), 7.18 (d, J=8.1 Hz, 1H). $^{13}$C NMR (101 MHz, DMSO-$d_6$) δ ppm 155.5, 151.1, 149.5, 142.3, 140.9, 137.8, 137.1, 131.5, 129.4, 128.7, 126.2, 125.8, 122.4, 122.0, 120.6 (q, $J_{CF}$=256.5 Hz, 1C), 119.5, 119.0. $^{19}$F NMR (376 MHz, DMSO-$d_6$) δ ppm −56.71. HRMS (m/z): $[M+H]^+$, calcd for $C_{16}H_{11}F_3N_3O_3$, 350.0747; found, 350.0741.

2-(4-Bromophenyl)-N-(oxazol-2-yl)isonicotinamide (48). This compound was prepared by the general procedures A, C and D affording 48 as a beige-colored powder (42 mg, 8%). $^1$H NMR (400 MHz, DMSO-$d_6$) δ ppm 12.00 (br s, 1H), 8.73-8.99 (m, 1H), 8.48 (br s, 1H), 8.07-8.25 (m, 2H), 7.94-8.06 (m, 1H), 7.80-7.94 (m, 1H), 7.75 (d, J=8.56 Hz, 2H), 7.13-7.41 (m, 1H). $^{13}$C NMR (101 MHz, DMSO-$d_6$) δ ppm 163.9, 156.2, 153.4, 151.0, 141.6, 137.7, 137.4, 132.3, 129.2, 127.5, 123.7, 121.5, 118.6. HRMS (m/z): $[M+H]^+$, calcd for $C_{15}H_{11}BrN_3O_2$, 344.0029; found, 344.0031.

2-(4-Nitrophenyl)-N-(oxazol-2-yl)isonicotinamide (49). This compound was prepared by the general procedures A, C, and D affording 49 as a yellow-colored powder (90 mg, 19%). $^1$H NMR (400 MHz, DMSO-$d_6$) δ ppm 12.14 (br s, 1H), 8.94 (d, J=5.1 Hz, 1H), 8.61 (s, 1H), 8.42-8.50 (m, 2H), 8.34-8.42 (m, 2H), 8.00 (br s, 1H), 7.95 (d, J=5.6 Hz, 1H), 7.28 (s, 1H). $^{13}$C NMR (101 MHz, DMSO-$d_6$) δ ppm 155.0, 151.3, 148.4, 144.4, 128.4, 124.5, 122.6, 119.9. HRMS (m/z): $[M+H]^+$, calcd for $C_{15}H_{11}N_4O_4$, 311.0775; found, 311.0783.

2-(3-Nitrophenyl)-N-(oxazol-2-yl)isonicotinamide (50). This compound was prepared by the general procedures A, C, and D affording 50 as an off-white powder (72 mg, 15%). $^1$H NMR (400 MHz, DMSO-$d_6$) δ ppm 12.15 (br s, 1H), 8.99 (s, 1H), 8.93 (d, J=4.9 Hz, 1H), 8.58-8.67 (m, 2H), 8.30-8.39 (m, 1H), 8.01 (s, 1H), 7.93 (d, J=4.9 Hz, 1H), 7.85 (t, J=8.0 Hz, 1H), 7.28 (s, 1H). $^{13}$C NMR (101 MHz, DMSO-$d_6$) δ ppm 154.8, 151.2, 149.0, 140.1, 133.4, 132.0, 131.9, 131.1, 129.3, 129.2, 124.6, 122.4, 121.7, 119.2. HRMS (m/z): $[M+H]^+$, calcd for $C_{15}H_{11}N_4O_4$, 311.0775; found, 311.0786.

2-(4-Methoxyphenyl)-N-(oxazol-2-yl)isonicotinamide (51). This compound was prepared by the general procedures A, C, and D affording 51 as an off-white powder (87 mg, 20%). $^1$H NMR (400 MHz, DMSO-$d_6$) δ ppm 12.01 (br s, 1H), 8.81 (d, J=5.1 Hz, 1H), 8.40 (s, 1H), 8.08-8.26 (m, 2H), 8.00 (br s, 1H), 7.63-7.86 (m, 1H), 7.27 (s, 1H), 6.96-7.19 (m, 2H), 3.85 (s, 3H). $^{13}$C NMR (101 MHz, DMSO-$d_6$) δ ppm 164.1, 161.0, 157.2, 153.5, 150.7, 141.4, 137.4, 131.0, 128.6, 127.4, 120.2, 117.7, 114.7, 55.7. HRMS (m/z): $[M+H]^+$, calcd for $C_{16}H_{14}N_3O_3$, 296.1029; found, 296.1033. 2-(4-Isopropoxyphenyl)-N-(oxazol-2-yl)isonicotinamide (52). This compound was prepared by the general procedures A, C, and D affording 52 as a light yellow-colored powder (112 mg, 23%). $^1$H NMR (400 MHz, DMSO-$d_6$) δ ppm 11.94 (br s, 1H), 8.80 (d, J=5.1 Hz, 1H), 8.39 (s, 1H), 8.05-8.18 (m, 2H), 8.01 (br s, 1H), 7.75 (br s, 1H), 7.25 (br s, 1H), 6.91-7.14 (m, 2H), 4.72 (td, J=6.1, 12.0 Hz, 1H), 1.31 (d, J=6.1 Hz, 6H). $^{13}$C NMR (101 MHz, DMSO-$d_6$) δ ppm 164.1, 159.3, 157.2, 153.4, 150.7, 141.3, 137.5, 130.7, 128.7, 127.5, 120.1, 117.6, 116.1, 69.7, 22.3. HRMS (m/z): $[M+H]^+$, calcd for $C_{18}H_{18}N_3O_3$, 324.1343; found, 324.1356.

2-(3,4-Dimethoxyphenyl)-N-(oxazol-2-yl)isonicotinamide (53). This compound was prepared by the general procedures A, C and D affording 53 as a light yellow-colored powder (138 mg, 28%). $^1$H NMR (400 MHz, DMSO-$d_6$) δ ppm 11.92 (br s, 1H), 8.63-8.92 (m, 1H), 8.25-8.54 (m, 1H), 8.02 (br s, 1H), 7.60-7.88 (m, 3H), 7.24 (br s, 1H), 7.11 (d, J=8.1 Hz, 1H), 3.84 (s, 6H). $^{13}$C NMR (101 MHz, DMSO-$d_6$) δ ppm 163.2, 156.1, 152.3, 149.7, 149.6, 148.4, 140.3, 136.5, 130.1, 126.4, 119.1, 119.0, 116.8, 111.2, 109.3, 55.0. HRMS (m/z): $[M+H]^+$, calcd for $C_{17}H_{16}N_3O_4$, 326.1135; found, 326.1140.

2-(3-Chloro-4-methoxyphenyl)-N-(oxazol-2-yl)isonicotinamide (54). This compound was prepared by the general procedures A, C, and D affording 54 as a light yellow-colored powder (83 mg, 17%). $^1$H NMR (400 MHz, DMSO-$d_6$) δ ppm 11.98 (br s, 1H), 8.82 (d, J=4.9 Hz, 1H), 8.44 (s, 1H), 8.20-8.29 (m, 1H), 8.05-8.20 (m, 1H), 8.00 (br s, 1H), 7.72-7.88 (m, 1H), 7.27-7.41 (m, 1H), 7.26 (s, 1H), 3.95 (s, 3H). $^{13}$C NMR (101 MHz, DMSO-$d_6$) δ ppm 164.0, 156.1, 155.8, 153.4, 150.8, 141.5, 137.5, 131.9, 128.5, 127.5, 127.3, 122.2, 120.8, 118.0, 113.5, 56.8. HRMS (m/z): $[M+H]^+$, calcd for $C_{16}H_{13}ClN_3O_3$, 330.0640; found, 330.0628.

2-(3-Cyanophenyl)-N-(oxazol-2-yl)isonicotinamide (55). This compound was prepared by the general procedures A, C, and D affording 55 as a colorless powder (101 mg, 23%). $^1$H NMR (400 MHz, DMSO-$d_6$) δ ppm 12.07 (br s, 1H), 8.90 (d, J=4.9 Hz, 1H), 8.58 (d, J=8.6 Hz, 2H), 8.51 (d, J=7.8 Hz, 1H), 7.93-8.03 (m, 2H), 7.89 (d, J=4.9 Hz, 1H), 7.77 (t, J=8.0 Hz, 1H), 7.26 (s, 1H). $^{13}$C NMR (101 MHz, DMSO-$d_6$) δ ppm 155.2, 151.1, 142.5, 139.7, 136.7, 133.4, 131.8, 130.73, 130.70, 122.2, 119.2, 119.1, 112.6. HRMS (m/z): $[M+H]^+$, calcd for $C_{16}H_{11}N_4O_2$, 291.0877; found, 291.0869.

2-(4-(Benzyloxy)phenyl)-N-(oxazol-2-yl)isonicotinamide (56). This compound was prepared by the general procedures A, C and D affording 56 as a colorless powder (182 mg, 33%). $^1$H NMR (400 MHz, DMSO-$d_6$) δ ppm 11.93 (br s, 1H), 8.80 (d, J=5.1 Hz, 1H), 8.39 (s, 1H), 8.09-8.19 (m, J=8.6 Hz, 2H), 8.00 (br s, 1H), 7.74 (br s, 1H), 7.47-7.54 (m, 2H), 7.39-7.45 (m, 2H), 7.31-7.39 (m, 1H), 7.24 (br s, 1H), 7.14-7.22 (m, 2H), 5.08-5.26 (m, 2H). $^{13}$C NMR (101 MHz, DMSO-$d_6$) δ ppm 160.1, 157.1, 150.7, 137.4, 131.2, 128.9, 1128.6, 128.4, 128.3, 117.7, 115.6, 69.8. HRMS (m/z): $[M+H]^+$, calcd for $C_{22}H_{18}N_3O_3$, 372.1343; found, 372.1358.

2-(3-(Benzyloxy)phenyl)-N-(oxazol-2-yl)isonicotinamide (57). This compound was prepared by the general procedures A, C, and D affording 57 as a light pink-colored powder (154 mg, 28%). $^1$H NMR (400 MHz, DMSO-$d_6$) δ ppm 11.95 (br s, 1H), 8.86 (d, J=5.1 Hz, 1H), 8.45 (s, 1H), 8.01 (br s, 1H), 7.73-7.88 (m, 3H), 7.38-7.53 (m, 5H), 7.31-7.38 (m, 1H), 7.21-7.28 (m, 1H), 7.15 (dd, J=1.5, 8.3 Hz, 1H), 5.22 (s, 2H). $^{13}$C NMR (101 MHz, DMSO-$d_6$) δ ppm 164.0, 159.4, 157.1, 153.4, 151.0, 150.8, 141.5, 140.1, 137.5, 130.5, 128.9, 128.3, 128.2, 121.3, 119.8, 118.8, 116.3, 113.6, 69.8. HRMS (m/z): $[M+H]^+$, calcd for $C_{22}H_{18}N_3O_3$, 372.1343; found, 372.1354.

Tert-butyl (4-(4-(oxazol-2-ylcarbamoyl)pyridin-2-yl)phenyl)carbamate (58). This compound was prepared by the general procedures A, C, and D affording 58 as a colorless powder (173 mg, 29%). $^1$H NMR (400 MHz, DMSO-$d_6$) δ ppm 12.02 (br s, 1H), 9.60 (s, 1H), 8.80 (d, J=4.9 Hz, 1H), 8.39 (s, 1H), 8.05-8.14 (m, 2H), 7.98 (s, 1H), 7.75 (dd, J=1.5, 5.1 Hz, 1H), 7.55-7.67 (m, 2H), 7.25 (s, 1H), 1.49 (s, 9H). $^{13}$C NMR (101 MHz, DMSO-$d_6$) δ ppm 157.2, 153.1, 150.7, 141.4, 137.0, 132.1, 127.7, 120.4, 118.5, 117.8, 79.8, 28.6. HRMS (m/z): $[M+H]^+$, calcd for $C_{20}H_{21}N_4O_4$, 381.1557; found, 381.1548.

Tert-butyl (3-(4-(oxazol-2-ylcarbamoyl)pyridin-2-yl)phenyl)carbamate (59). This compound was prepared by the general procedures A, C, and D affording 59 as a colorless powder (143 mg, 25%). $^1$H NMR (400 MHz, DMSO-$d_6$) δ ppm 12.01 (br s, 1H), 9.52 (s, 1H), 8.86 (d, J=4.9 Hz, 1H), 8.38 (s, 2H), 7.84 (d, J=5.1 Hz, 1H), 7.76 (d, J=7.6 Hz, 1H), 7.47-7.59 (m, 1H), 7.34-7.46 (m, 1H), 7.26 (br s, 1H), 1.49 (s, 9H). $^{13}$C NMR (101 MHz, DMSO-$d_6$) δ ppm 166.7, 162.8, 157.4, 153.3, 150.8, 140.6, 139.1, 129.7, 129.6, 121.1, 121.0, 119.8, 119.3, 118.6, 116.9, 79.6, 28.6. HRMS (m/z): $[M+H]^+$, calcd for $C_{20}H_{21}N_4O_4$, 381.1557; found, 381.1552.

N-(Oxazol-2-yl)-2-phenylisonicotinamide (60). This compound was prepared by the general procedures A, C, and D affording 60 as a yellow-colored powder (87 mg, 22%). $^1$H NMR (400 MHz, DMSO-$d_6$) δ ppm 8.69 (d, J=4.9 Hz, 1H), 8.35-8.56 (m, 1H), 7.98-8.14 (m, 2H), 7.77-7.97 (m, 1H), 7.36-7.57 (m, 4H), 6.89 (s, 1H). $^{13}$C NMR (101 MHz, DMSO-$d_6$) δ ppm 167.2, 165.6, 156.4, 150.0, 149.4, 139.5, 131.8, 129.4, 129.3, 126.9, 126.8, 121.8, 119.2. HRMS (m/z): $[M+H]^+$, calcd for $C_{15}H_{12}N_3O_2$, 266.0924; found, 266.0917.

N-(Oxazol-2-yl)-2-(quinolin-3-yl)isonicotinamide (61). This compound was prepared by the general procedures A, C, and D affording 61 as a beige-colored powder (170 mg, 36%). $^1$H NMR (400 MHz, DMSO-$d_6$) δ ppm 12.01-12.26 (m, 1H), 9.68 (d, J=2.2 Hz, 1H), 9.05-9.13 (m, 1H), 8.94 (d, J=5.4 Hz, 1H), 8.68 (s, 1H), 8.14 (d, J=6.6 Hz, 1H), 8.09 (d, J=9.3 Hz, 1H), 8.00 (s, 1H), 7.91 (dd, J=1.6, 5.0 Hz, 1H), 7.82 (ddd, J=1.5, 6.9, 8.5 Hz, 1H), 7.63-7.72 (m, 1H), 7.28 (d, J=1.0 Hz, 1H). $^{13}$C NMR (101 MHz, DMSO-$d_6$) δ ppm 155.2, 151.2, 149.5, 148.3, 142.5, 136.7, 134.3, 131.2, 130.9, 129.4, 129.2, 127.8, 127.7, 127.2, 121.8, 119.4. HRMS (m/z): $[M+H]^+$, calcd for $C_{18}H_{13}N_4O_2$, 317.1033; found, 317.1046.

2-Morpholino-N-(oxazol-2-yl)isonicotinamide (62). This compound was prepared from commercial 2-morpholin-4-yl-isonicotinic acid following the general procedure D affording 62 as a pale yellow-colored powder (56 mg, 13%). $^1$H NMR (400 MHz, DMSO-$d_6$) δ ppm 11.67 (br s, 1H), 8.28 (d, J=5.1 Hz, 1H), 7.98 (br s, 1H), 7.32 (br s, 1H), 7.15-7.26 (m, 1H), 7.03-7.15 (m, 1H), 3.66-3.77 (m, 4H), 3.46-3.57 (m, 4H). $^{13}$C NMR (101 MHz, DMSO-$d_6$) δ ppm 158.9, 147.9, 136.4, 126.4, 110.4, 104.6, 65.3, 44.4. HRMS (m/z): $[M+H]^+$, calcd for $C_{13}H_{15}N_4O_3$, 275.1139; found, 275.1149.

N-(Oxazol-2-yl)-2-(trifluoromethyl)isonicotinamide (63). This compound was prepared from commercial 2-(trifluoromethyl)isonicotinic acid following the general procedure D affording 63 as a pale red-colored powder (42 mg, 11%). $^1$H NMR (400 MHz, DMSO-$d_6$) δ ppm 12.43 (br s, 1H), 8.98 (d, J=4.9 Hz, 1H), 8.36 (s, 1H), 8.23 (d, J=4.9 Hz, 1H), 7.95 (s, 1H), 7.31 (s, 1H). $^{13}$C NMR (101 MHz, DMSO-$d_6$) δ ppm 164.3, 151.0, 150.7, 146.5 (q, $J_{CF}$=34.1 Hz, 1C), 126.0, 125.2, 120.9 (q, $J_{CF}$=274.1 Hz, 1C), 118.9, 118.3 (q, $J_{CF}$=2.8 Hz, 1C). $^{19}$F NMR (376 MHz, DMSO-$d_6$) δ ppm −66.58. HRMS (m/z): $[M+H]^+$, calcd for $C_{10}H_7F_3N_3O_2$, 258.0485; found, 258.0486.

Scheme 8: Synthetic route for accessing comounds 64

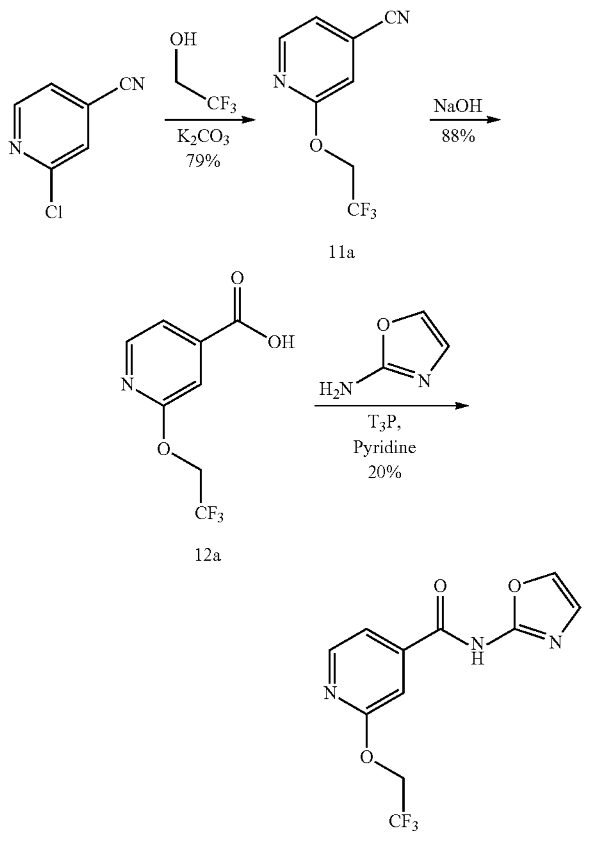

11a

12a

64

2-(2,2,2-Trifluoroethoxy)isonicotinonitrile (11a). 2,2,2-Trifluoroethanol (2.71 g, 23.8 mmol) and 50 mL of dry THF were added to an oven-dry flask under a nitrogen atmosphere and cooled to −5° C. Powdered NaH (570 mg, 23.8 mmol) was added in small portions over 10 min. The solution was stirred for 30 min, and solid 2-chloro-4-cyanopyridine (3.0 g, 21.7 mmol) was added in small portions over 10 min. After 1 h, the solution was heated at 50° C. for 1 h. The reaction mixture was cooled and a drop of water was added to quench the reaction. The solvent was removed in vacuo and the residue was purified by silica chromatography using gradient elution from 9:1 Hexane/EtOAc to EtOAc, affording 11a as a colorless liquid (3.45 g, 79%). $^{1}$H NMR (400 MHz, $CDCl_3$) δ ppm 8.33 (d, J=5.1 Hz, 1H), 7.21 (td, J=1.1, 5.1 Hz, 1H), 7.11-7.18 (m, 1H), 4.74-4.89 (m, 2H)$^{13}$C NMR (101 MHz, DMSO-$d_6$) δ ppm 161.9, 148.2, 123.28, 123.27 (q, $J_{CF}$=277.5 Hz, 1C), 119.4, 116.0, 114.2, 62.5 (q, $J_{CF}$=36.4 Hz, 1C). $^{19}$F NMR (376 MHz, DMSO-$d_6$) δ ppm −72.43. HRMS (m/z): [M+H]$^+$, calcd for $C_8H_4F_3N_2O$, 201.0281; found, 201.0272.

2-(2,2,2-Trifluoroethoxy)isonicotinic acid (12a). This compound was prepared starting from 11a, following the general procedure C affording 12a as a white solid (3.45 g, 79%). $^{1}$H NMR (400 MHz, DMSO-$d_6$) δ ppm 13.75 (br s, 1H), 8.34 (d, J=5.4 Hz, 1H), 7.49 (d, J=5.2 Hz, 1H), 7.30 (s, 1H), 4.77-5.06 (m, 2H). $^{13}$C NMR (101 MHz, DMSO-$d_6$) δ ppm 165.9, 162.3, 148.2, 142.8, 124.4 (q, $J_{CF}$=277.8 Hz, 1C), 118.0, 110.7, 62.1 (q, $J_{CF}$=34.8 Hz, 1C). $^{19}$F NMR (376 MHz, DMSO-$d_6$) δ ppm −72.56. HRMS (m/z): [M+H]$^+$, calcd for $C_8H_7F_3NO_3$, 222.0373; found, 222.0368.

N-(Oxazol-2-yl)-2-(2,2,2-trifluoroethoxy)isonicotinamide (64). This compound was prepared starting from 12a by the general procedure D affording 64 as a white powder (87 mg, 20%). $^{1}$H NMR (400 MHz, DMSO-$d_6$) δ ppm 12.01 (br s, 1H), 8.39 (d, J=5.4 Hz, 1H), 7.96 (s, 1H), 7.60 (d, J=5.4 Hz, 1H), 7.48 (s, 1H), 7.26 (s, 1H), 5.07 (q, J=9.1 Hz, 2H). $^{13}$C NMR (101 MHz, DMSO-$d_6$) δ ppm 161.2, 147.0, 135.6, 123.5 (q, $J_{CF}$=277.8 Hz, 1C), 116.4, 108.9, 61.1 (q, $J_{CF}$=34.7 Hz, 1C). $^{19}$F NMR (376 MHz, DMSO-$d_6$) δ ppm −72.38. HRMS (m/z): [M+H]$^+$, calcd for $C_{11}H_9F_3N_3O_3$, 288.0591; found, 288.0600.

N-(Oxazol-2-yl)-2-(3,3,3-trifluoropropoxy)isonicotinamide (65). This compound was prepared by the same procedure for 64, affording 65 as a white powder (109 mg, 24%). $^{1}$H NMR (400 MHz, DMSO-$d_6$) δ ppm 11.82 (br s, 1H), 8.36 (d, J=5.4 Hz, 1H), 7.97 (br s, 1H), 7.41-7.60 (m, 1H), 7.34 (s, 1H), 7.24 (br s, 1H), 4.55 (t, J=6.0 Hz, 2H), 2.70-2.93 (m, 2H). $^{13}$C NMR (101 MHz, DMSO-$d_6$) δ ppm 162.5, 147.2, 136.4, 126.4, 126.2 (q, $J_{CF}$=276.9 Hz, 1C), 115.1, 108.8, 58.5, 31.9 (q, $J_{CF}$=27.7 Hz, 1C). $^{19}$F NMR (376 MHz, DMSO-$d_6$) δ ppm −63.06. HRMS (m/z): [M+H] V, calcd for $Cl_2H_{11}F_3N_3O_3$, 302.0747; found, 302.0737.

Scheme 9: Synthetic route for accessing compound 66

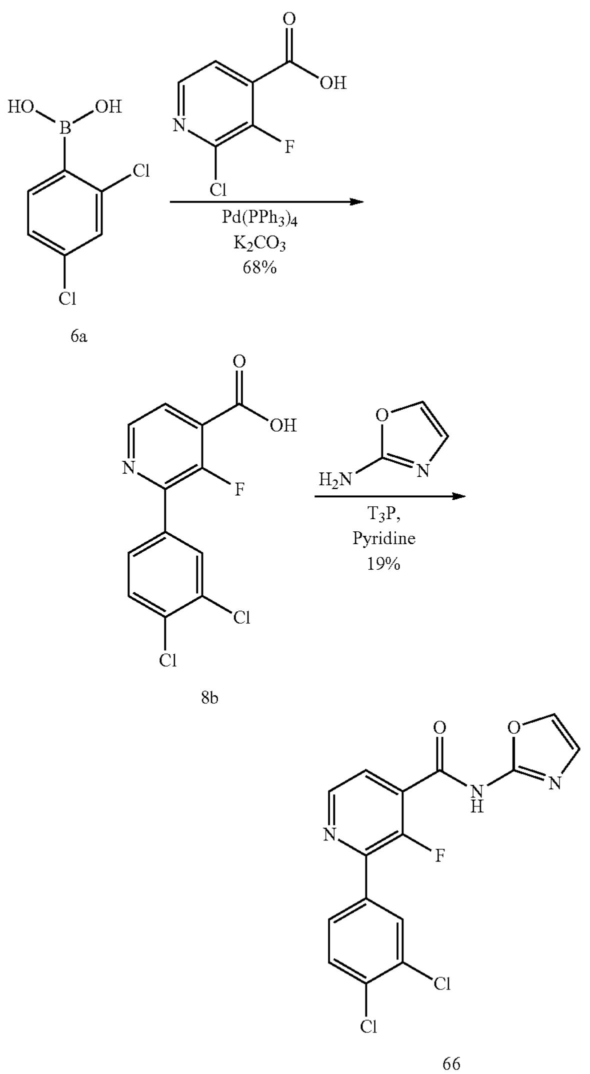

6a

8b

66

2-(3,4-Dichlorophenyl)-3-fluoroisonicotinic acid (8b). 1,4-Dioxane (75 mL) and a 2M aqueous solution of $Na_2CO_3$ (25 mL), were added to a 250 mL flask under an argon atmosphere. 3,4-Dichlorobenzeneboronic acid (4.07 g, 21.36 mmol) and 2-chloro-3-fluoroisonicotinic acid (2.50 g, 14.24 mmol) were added after 5 min. Argon was bubbled through a needle into the solution for 20 min. $Pd(PPh_3)_4$ (493 mg, 0.4 mmol) was added. The reaction mixture was heated at reflux and aged overnight. The solution was allowed to cool to room temperature. The solvent was evaporated under reduced pressure to a quarter of the initial volume. Aqueous 6 M HCl was added to achieve a pH 3. The precipitate was collected by filtration and washed with water (3×10 mL). The solid was dried under reduced pressure, and crystallized from ethanol to afford 8b as an off-white-colored solid (3.20 g, 68%). $^1$H NMR (400 MHz, DMSO-$d_6$) δ ppm 14.11 (br s, 1H), 8.63 (d, J=4.9 Hz, 1H), 8.08 (dd, J=0.9, 2.1 Hz, 1H), 7.86 (td, J=1.8, 8.6 Hz, 1H), 7.72-7.82 (m, 2H). $^{13}$C NMR (101 MHz, DMF-$d_7$) 6 ppm 164.2, 155.0 (d, $J_{CF}$=270.5 Hz, 1C), 146.4 (d, $J_{CF}$=6.9 Hz, 1C), 144.7 (d, $J_{CF}$=11.8 Hz, 1C), 135.4 (d, $J_{CF}$=5.2 Hz, 1C), 132.8, 131.9, 131.3, 130.9 (d, $J_{CF}$=5.8 Hz, 1C), 129.3 (d, $J_{CF}$6.8 Hz, 1C), 128.7, 125.2. $^{19}$F NMR (376 MHz, DMSO-$d_6$) δ ppm −124.59. HRMS (m/z): $[M+H]^+$, calcd for $C_{12}H_7Cl_2FNO_2$, 285.9832; found, 285.9828.

2-(3,4-Dichlorophenyl)-3-fluoro-N-(oxazol-2-yl)isonicotinamide (66). This compound was prepared starting from 8c, following the general procedure D affording 66 as a colorless powder (98 mg, 19%). $^1$H NMR (400 MHz, DMSO-$d_6$) δ ppm 12.15 (br s, 1H), 8.68 (d, J=4.9 Hz, 1H), 8.09-8.21 (m, 1H), 7.88-8.02 (m, 2H), 7.80-7.87 (m, 1H), 7.69-7.79 (m, 1H), 7.21 (br s, 1H). $^{13}$C NMR (101 MHz, DMF-$d_7$) 6 ppm 154.1 (d, $J_{CF}$=265.4 Hz, 1C), 146.4 (d, $J_{CF}$=5.6 Hz, 1C), 144.0 (d, $J_{CF}$=10.8 Hz, 1C), 136.5, 135.7 (d, $J_{CF}$=4.4 Hz, 1C), 133.2, 132.9, 132.2, 131.3, 130.8 (d, $J_{CF}$=5.3 Hz, 1C), 129.1 (d, $J_{CF}$=6.7 Hz, 1C), 124.2. $^{19}$F NMR (376 MHz, DMSO-$d_6$) δ ppm −117.19. HRMS (m/z): $[M+H]^+$, calcd for $C_{15}H_9Cl_2FN_3O_2$, 352.0050; found, 352.0065.

2-(3-Chloro-4-fluorophenyl)-3-fluoro-N-(oxazol-2-yl) isonicotinamide (67). This compound was prepared by the same procedure for 66, affording 67 as a colorless powder (79 mg, 16%). $^1$H NMR (400 MHz, DMSO-$d_6$) δ ppm 12.16 (br s, 1H), 8.67 (d, J=4.7 Hz, 1H), 8.11 (d, J=7.3 Hz, 1H), 7.96 (s, 2H), 7.74 (t, J=5.0 Hz, 1H), 7.62 (t, J=9.1 Hz, 1H), 7.21 (br s, 1H). $^{13}$C NMR (101 MHz, DMSO-$d_6$) δ ppm 158.4 (d, $J_{CF}$=249.9 Hz, 1C), 153.6 (d, $J_{CF}$=264.9 Hz, 1C), 146.5 (d, $J_{CF}$=6.3 Hz, 1C), 144.1 (d, $J_{CF}$=11.0 Hz, 1C), 132.7 (dd, $J_{CF}$=5.3, 3.4 Hz, 1C), 132.5 (d, $J_{CF}$=2.8 Hz, 1C), 132.0 (d, $J_{CF}$=9.8 Hz, 1C), 131.2 (d, $J_{CF}$=5.5 Hz, 1C), 130.03 (d, $J_{CF}$=14.4 Hz, 1C), 130.02, 129.2 (d, $J_{CF}$=11.7 Hz, 1C), 124.0, 120.4 (d, $J_{CF}$=18.0 Hz, 1C), 117.8 (d, $J_{CF}$=21.3 Hz, 1C). $^{19}$F NMR (376 MHz, DMSO-$d_6$) δ ppm −114.61, −126.43. HRMS (m/z): $[M+H]^+$, calcd for $C_{15}H_9ClF_2N_3O_2$, 336.0346; found, 336.0352.

2-(3,4-Difluorophenyl)-3-fluoro-N-(oxazol-2-yl)isonicotinamide (68). This compound was prepared by the same procedure as for 66, affording 68 as a colorless powder (201 mg, 42%). $^1$H NMR (400 MHz, DMSO-$d_6$) δ ppm 12.13 (br s, 1H), 8.58-8.72 (m, 1H), 7.90-8.04 (m, 2H), 7.77-7.86 (m, 1H), 7.73 (t, J=4.8 Hz, 1H), 7.64 (td, J=8.6, 10.8 Hz, 1H), 7.21 (br s, 1H). $^{13}$C NMR (101 MHz, DMSO-$d_6$) δ ppm 153.6 (d, $J_{CF}$=264.9 Hz, 1C), 150.7 (dd, $J_{CF}$=248.7, 12.3 Hz, 1C), 149.9 (dd, $J_{CF}$=245.5, 12.6 Hz, 1C), 146.4 (d, $J_{CF}$=6.4 Hz, 1C), 144.1 (dd, $J_{CF}$=8.5, 3.3 Hz, 1C), 132.4 (dd, $J_{CF}$=9.4, 5.7 Hz, 1C), 126.4 (td, $J_{CF}$=6.9, 3.4 Hz, 1C), 123.9, 118.4 (d, $J_{CF}$=17.2 Hz, 1C), 118.2 (dd, $J_{CF}$=18.6, 5.1 Hz, 1C). $^{19}$F NMR (376 MHz, DMSO-$d_6$) δ ppm −19F NMR (376 MHz, DMSO) δ −126.48, −136.73 (d, J=28.1 Hz), −137.90 (d, J=24.4 Hz). HRMS (m/z): [M+H]V, calcd for $C_{15}H_9F_3N_3O_2$, 320.0641; found, 320.0653.

2-(3-Chlorophenyl)-3-fluoro-N-(oxazol-2-yl)isonicotinamide (69). This compound was prepared by the same procedure for 66, affording 69 as a colorless powder (123 mg, 26%). $^1$H NMR (400 MHz, DMSO-$d_6$) δ ppm 12.15 (br s, 1H), 8.68 (d, J=4.9 Hz, 1H), 7.95 (br s, 2H), 7.82-7.93 (m, 1H), 7.74 (t, J=4.8 Hz, 1H), 7.54-7.64 (m, 2H), 7.21 (br s, 1H). $^{13}$C NMR (101 MHz, DMSO-$d_6$) δ ppm 163.4, 155.2 (d, $J_{CF}$=244.0 Hz, 1C), 149.6 (d, $J_{CF}$=3.1 Hz, 1C), 149.4, 124.4, 123.2, 122.8 (d, $J_{CF}$=7.5 Hz, 1C), 121.2, 120.5 (d, $J_{CF}$=19.4 Hz, 1C), 118.0 (d, $J_{CF}$=22.7 Hz, 1C), 116.8, 115.0. $^{19}$F NMR (376 MHz, DMSO-$d_6$) δ ppm −126.31. HRMS (m/z): $[M+H]^+$, calcd for $C_{15}H_{10}ClFN_3O_2$, 318.0440; found, 318.0455.

2-(3,4-Dichlorophenyl)-5-fluoro-N-(oxazol-2-yl)isonicotinamide (70). This compound was prepared by the same procedure for 66, affording 70 as a colorless powder (130 mg, 25%). $^1$H NMR (400 MHz, DMSO-$d_6$) δ ppm 12.20 (br s, 1H), 8.82 (s, 1H), 8.40 (d, J=5.4 Hz, 1H), 8.34 (d, J=2.2 Hz, 1H), 8.10 (dd, J=2.2, 8.6 Hz, 1H), 7.97 (s, 1H), 7.76 (d, J=8.6 Hz, 1H), 7.22 (br s, 1H). $^{13}$C NMR (101 MHz, DMSO-$d_6$) δ ppm 155.6 (d, $J_{CF}$=261.6 Hz, 1C), 150.7 (d, $J_{CF}$=4.8 Hz, 1C), 139.6 (d, $J_{CF}$=25.3 Hz, 1C), 138.1, 136.8, 132.6, 132.4, 131.6, 128.8, 127.1, 121.0, 100.0. $^{19}$F NMR (376 MHz, DMSO-$d_6$) δ ppm −131.03. HRMS (m/z): $[M+H]^+$, calcd for $C_{15}H_9Cl_2FN_3O_2$, 352.0050; found, 352.0057.

2-(3-Chlorophenyl)-5-fluoro-N-(oxazol-2-yl)isonicotinamide (71). This compound was prepared by the same procedure for 66, affording 71 as a colorless powder (174 mg, 37%). $^1$H NMR (400 MHz, DMSO-$d_6$) δ ppm 12.17 (br s, 1H), 8.83 (s, 1H), 8.36 (d, J=5.4 Hz, 1H), 8.17 (s, 1H), 8.02-8.13 (m, 1H), 7.97 (s, 1H), 7.48-7.62 (m, 2H), 7.22 (br s, 1H). $^{13}$C NMR (101 MHz, DMSO-$d_6$) δ ppm 151.7 (d, $J_{CF}$=4.6 Hz, 1C), 139.7, 139.5 (d, $J_{CF}$=24.9 Hz, 1C), 134.3, 131.3, 129.6, 126.8, 125.7, 120.9. $^{19}$F NMR (376 MHz, DMSO-$d_6$) δ ppm −131.60. HRMS (m/z): $[M+H]^+$, calcd for $C_{15}H_{10}ClFN_3O_2$, 318.0440; found, 318.0454.

2-(3,4-Difluorophenyl)-5-fluoro-N-(oxazol-2-yl)isonicotinamide (72). This compound was prepared by the same procedure for 66, affording 72 as a colorless powder (142 mg, 30%). $^1$H NMR (400 MHz, DMSO-$d_6$) δ ppm 12.17 (br s, 1H), 8.82 (s, 1H), 8.35 (d, J=5.4 Hz, 1H), 8.10-8.24 (m, 1H), 7.91-8.06 (m, 2H), 7.59 (q, J=9.3 Hz, 1H), 7.22 (br s, 1H). $^{13}$C NMR (101 MHz, DMSO-$d_6$) δ ppm 155.4 (d, $J_{CF}$=261.0 Hz, 1C), 151.1 (d, $J_{CF}$=4.3 Hz, 1C), 150.7 (dd, $J_{CF}$=14.9, 250.8 Hz, 1C), 150.3 (dd, $J_{CF}$=15.1, 247.4 Hz, 1C), 139.4 (d, $J_{CF}$=24.7 Hz, 1C), 136.8, 135.2 (t, $J_{CF}$=4.6 Hz, 1C), 131.7, 124.0 (t, $J_{CF}$=4.7 Hz, 1C), 120.6, 118.5 (t, $J_{CF}$=8.9 Hz, 1C), 116.1 (dd, $J_{CF}$=4.3, 14.8 Hz, 1C), 107.3. $^{19}$F NMR (376 MHz, DMSO-$d_6$) δ ppm −131.82, −137.88, −137.94. HRMS (m/z): $[M+H]^+$, calcd for $C_{15}H_9F_3N_3O_2$, 320.0641; found, 320.0647.

2-(3-Chloro-4-fluorophenyl)-5-fluoro-N-(oxazol-2-yl) isonicotinamide (73). This compound was prepared by the same procedure for 66, affording 73 as a colorless powder (161 mg, 30%). $^1$H NMR (400 MHz, DMSO-$d_6$) δ ppm 12.12 (br s, 1H), 8.82 (s, 1H), 8.27-8.42 (m, 2H), 8.08-8.19 (m, 1H), 7.97 (br s, 1H), 7.58 (t, J=8.9 Hz, 1H), 7.22 (br s, 1H). $^{13}$C NMR (101 MHz, DMSO-$d_6$) δ ppm 158.4 (d, $J_{CF}$=249.5 Hz, 1C), 151.0 (d, $J_{CF}$=4.6 Hz, 1C), 145.6, 139.6 (d, $J_{CF}$=1.9 Hz, 1C), 135.4 (d, $J_{CF}$=1.4 Hz, 1C), 129.2, 127.8 (d, $J_{CF}$=7.9 Hz, 1C), 120.8, 120.7 (d, $J_{CF}$=9.0 Hz, 1C), 117.9 (d, $J_{CF}$=21.2 Hz, 1C). $^{19}$F NMR (376 MHz, DMSO-$d_6$) δ ppm −115.77, −131.85. HRMS (m/z): $[M+H]^+$, calcd for $C_{15}H_9ClF_2N_3O_2$, 336.0346; found, 336.0342.

2-(4-Chloro-3-fluorophenyl)-5-fluoro-N-(oxazol-2-yl) isonicotinamide (74). This compound was prepared by the same procedure for 66, affording 74 as a colorless powder (142 mg, 27%). $^1$H NMR (400 MHz, DMSO-$d_6$) δ ppm 12.19 (br s, 1H), 8.84 (s, 1H), 8.39 (d, J=5.4 Hz, 1H), 8.14 (dd, J=2.0, 11.0 Hz, 1H), 7.90-8.05 (m, 2H), 7.75 (t, J=8.2 Hz, 1H), 7.22 (br s, 1H). $^{13}$C NMR (101 MHz, DMSO-$d_6$) δ ppm 158.1 (d, $J_{CF}$=246.0 Hz, 1C), 155.5 (d, $J_{CF}$=260.0 Hz, 1C), 154.2, 150.92 (d, $J_{CF}$=2.2 Hz, 1C), 150.87 (d, $J_{CF}$=2.2 Hz, 1C), 139.6 (d, $J_{CF}$=24.9 Hz, 1C), 138.7 (d, $J_{CF}$=7.1 Hz, 1C), 131.7, 124.2 (d, $J_{CF}$=2.8 Hz, 1C), 121.1 (d, $J_{CF}$=17.5 Hz, 1C), 120.9, 115.2 (d, $J_{CF}$22.8 Hz, 1C). $^{19}$F NMR (376 MHz, DMSO-$d_6$) δ ppm −115.63, −131.09. HRMS (m/z): $[M+H]^+$, calcd for $C_{15}H_9ClF_2N_3O_2$, 336.0346; found, 336.0344.

6-(3,4-Dichlorophenyl)-N-(oxazol-2-yl)picolinamide (75). This compound was prepared by the general procedures A, C, and D affording 75 as a colorless powder (219 mg, 44%). $^1$H NMR (400 MHz, DMSO-$d_6$) δ ppm 11.59 (s, 1H), 8.81 (s, 1H), 8.38 (d, J=7.8 Hz, 2H), 8.14-8.22 (m, 1H), 8.09-8.14 (m, 1H), 8.07 (s, 1H), 7.79 (d, J=8.6 Hz, 1H), 7.27 (s, 1H). $^{13}$C NMR (101 MHz, DMSO-$d_6$) δ ppm 162.6, 152.4, 152.0, 147.9, 138.9, 137.2, 137.1, 131.9, 131.4, 130.2, 128.6, 126.8, 126.6, 123.6, 121.7. HRMS (m/z): $[M+H]^+$, calcd for $C_{15}H_{10}Cl_2N_3O_2$, 334.0145; found, 334.0137.

6-(3-Chlorophenyl)-N-(oxazol-2-yl)picolinamide (76). This compound was prepared by the general procedures A, C, and D affording 76 as a colorless powder (245 mg, 55%). $^1$H NMR (400 MHz, DMSO-$d_6$) δ ppm 11.54 (s, 1H), 8.59 (s, 1H), 8.25-8.39 (m, 2H), 8.17 (t, J=7.7 Hz, 1H), 8.11 (dd, J=1.0, 7.8 Hz, 1H), 8.02-8.08 (m, 1H), 7.50-7.60 (m, 2H), 7.27 (s, 1H). $^{13}$C NMR (101 MHz, DMSO-$d_6$) δ ppm 162.7, 153.4, 152.0, 147.9, 138.8, 137.1, 133.4, 129.9, 129.0, 126.6, 126.5, 125.3, 123.6, 121.5. HRMS (m/z): $[M+H]^+$, calcd for $C_{15}H_{11}ClN_3O_2$, 300.0534; found, 300.0526.

6-(3-Chloro-4-fluorophenyl)-N-(oxazol-2-yl)picolinamide (77). This compound was prepared by the general procedures A, C, and D affording 77 as a colorless powder (233 mg, 49%). $^1$H NMR (400 MHz, DMSO-$d_6$) δ ppm 11.49-11.63 (m, 1H), 8.72-8.84 (m, 1H), 8.41 (tdd, J=2.0, 4.5, 8.7 Hz, 1H), 8.31-8.37 (m, 1H), 8.12-8.19 (m, 1H), 8.08-8.12 (m, 1H), 8.07 (s, 1H), 7.53-7.62 (m, 1H), 7.27 (s, 1H). $^{13}$C NMR (101 MHz, DMSO-$d_6$) δ ppm 162.6, 157.6 (d, $J_{CF}$=249.6 Hz, 1C), 152.6, 152.1, 147.8, 138.8, 137.1, 134.4 (d, $J_{CF}$=3.3 Hz, 1C), 129.1, 127.5 (d, $J_{CF}$=7.7 Hz, 1C), 126.6, 123.4, 121.4, 119.7 (d, $J_{CF}$=17.8 Hz, 1C), 116.5 (d, $J_{CF}$=21.1 Hz, 1C). $^{19}$F NMR (376 MHz, DMSO-$d_6$) δ ppm −115.32. HRMS (m/z): $[M+H]^+$, calcd for $C_{15}H_{10}ClFN_3O_2$, 318.0440; found, 318.0429.

6-(4-Chloro-3-fluorophenyl)-N-(oxazol-2-yl)picolinamide (78). This compound was prepared by the general procedures A, C, and D affording 78 as a colorless powder (250 mg, 52%). $^1$H NMR (400 MHz, DMSO-$d_6$) δ ppm 11.47-11.66 (m, 1H), 8.70 (d, J=11.5 Hz, 1H), 8.32-8.43 (m, 1H), 8.25 (d, J=8.6 Hz, 1H), 8.15-8.21 (m, 1H), 8.09-8.15 (m, 1H), 8.07 (s, 1H), 7.68-7.81 (m, 1H), 7.24-7.33 (m, 1H). $^{13}$C NMR (101 MHz, DMSO-$d_6$) δ ppm 169.7, 162.5, 157.2 (d, $J_{CF}$=245.3 Hz, 1C), 152.5, 152.0, 147.8, 138.9, 137.9 (d, $J_{CF}$=7.2 Hz, 1C), 137.1, 130.2, 126.6, 123.6 (d, $J_{CF}$=17.4 Hz, 1C), 121.7, 120.3 (d, $J_{CF}$=17.8 Hz, 1C), 115.2 (d, $J_{CF}$=22.8 Hz, 1C). $^{19}$F NMR (376 MHz, DMSO-$d_6$) δ ppm −115.96. HRMS (m/z): [M+H]V, calcd for $C_{15}H_{10}ClFN_3O_2$, 318.0440; found, 318.0436.

6-(4-Fluorophenyl)-N-(oxazol-2-yl)picolinamide (79). This compound was prepared by the general procedures A, C, and D affording 79 as a colorless powder (270 mg, 64%). $^1$H NMR (400 MHz, DMSO-$d_6$) δ ppm 11.48 (s, 1H), 8.42-8.56 (m, 2H), 8.29 (d, J=7.8 Hz, 1H), 8.14 (t, J=7.8 Hz, 1H), 8.00-8.10 (m, 2H), 7.30-7.40 (m, 2H), 7.26 (s, 1H). $^{13}$C NMR (101 MHz, DMSO-$d_6$) δ ppm 163.8 (d, $J_{CF}$=247.3 Hz, 1C), 163.6, 155.0, 153.2, 148.8, 139.6, 138.0, 134.2 (d, $J_{CF}$=2.8 Hz, 1C), 130.1 (d, $J_{CF}$=8.5 Hz, 2C), 127.7, 124.1, 121.8, 116.0 (d, $J_{CF}$=21.4 Hz, 2C). $^{19}$F NMR (376 MHz, DMSO-$d_6$) δ ppm −112.12. HRMS (m/z): $[M+H]^+$, calcd for $C_{15}H_{11}FN_3O_2$, 284.0830; found, 284.0836.

6-(3,4-Difluorophenyl)-N-(oxazol-2-yl)picolinamide (80). This compound was prepared by the general procedures A, C, and D affording 80 as a colorless powder (259 mg, 57%). $^1$H NMR (400 MHz, DMSO-$d_6$) δ ppm 11.56 (s, 1H), 8.66-8.80 (m, 1H), 8.30-8.39 (m, 1H), 8.20-8.28 (m, 1H), 8.17 (t, J=7.8 Hz, 1H), 8.00-8.13 (m, 2H), 7.51-7.65 (m, 1H), 7.19-7.32 (m, 1H). $^{13}$C NMR (101 MHz, DMSO-$d_6$) δ ppm 162.6, 152.7, 152.1, 149.9 (dd, $J_{CF}$=12.5, 248.5 Hz, 1C), 149.4 (dd, $J_{CF}$=12.2, 244.2 Hz, 1C), 147.8, 138.8, 137.1, 134.3 (dd, $J_{CF}$=3.4, 6.2 Hz, 1C), 126.6, 123.6 (dd, $J_{CF}$=3.2, 6.7 Hz, 1C), 123.3, 121.4, 117.1 (d, $J_{CF}$=17.1 Hz, 1C), 116.2 (d, $J_{CF}$=18.7 Hz, 1C). $^{19}$F NMR (376 MHz, DMSO-$d_6$) δ ppm 19F NMR (376 MHz, DMSO) −138.29 (d, J=22.3 Hz, 1F), −137.44 (d, J=22.3 Hz, 1F). HRMS (m/z): $[M+H]^+$, calcd for $C_{15}H_{10}F_2N_3O_2$, 302.0736; found, 302.0738.

5-(3-Chloro-4-fluorophenyl)-N-(oxazol-2-yl)nicotinamide (81). This compound was prepared by the general procedures A, C and D affording 81 as a colorless powder (37 mg, 8%). $^1$H NMR (400 MHz, DMSO-$d_6$) δ ppm 11.91 (br s, 1H), 9.14 (br s, 1H), 9.10 (br s, 1H), 8.63 (br s, 1H), 8.14 (d, J=7.8 Hz, 1H), 7.99 (br s, 1H), 7.89 (br s, 1H), 7.61 (t, J=9.1 Hz, 1H), 7.25 (br s, 1H). $^{13}$C NMR (101 MHz, DMSO-$d_6$) δ ppm 158.0 (d, $J_{CF}$=248.5 Hz, 1C), 151.2 (d, $J_{CF}$=2.8 Hz, 1C), 149.0, 134.6 (d, $J_{CF}$=3.9 Hz, 1C), 134.2, 133.4, 129.8, 128.4 (d, $J_{CF}$=7.6 Hz, 1C), 120.9 (d, $J_{CF}$=17.9 Hz, 1C), 118.1 (d, $J_{CF}$=21.2 Hz, 1C). $^{19}$F NMR (376 MHz, DMSO-$d_6$) δ ppm −116.85. HRMS (m/z): $[M+H]^+$, calcd for $C_{15}H_{10}ClFN_3O_2$, 318.0440; found, 318.0432.

5-(3,4-Difluorophenyl)-N-(oxazol-2-yl)nicotinamide (82). This compound was prepared by the general procedures A, C, and D affording 82 as a colorless powder (84 mg, 19%). $^1$H NMR (400 MHz, DMSO-$d_6$) δ ppm 11.96 (br s, 1H), 9.13 (s, 1H), 9.10 (s, 1H), 8.63 (t, J=2.2 Hz, 1H), 7.92-8.08 (m, 2H), 7.71-7.80 (m, 1H), 7.63 (td, J=8.6, 10.7 Hz, 1H), 7.25 (s, 1H). $^{13}$C NMR (101 MHz, DMSO-$d_6$) δ ppm 170.8, 151.5 (t, $J_{CF}$=12.1 Hz, 1C), 150.1 (d, $J_{CF}$=216.0 Hz, 1C), 149.1 (t, $J_{CF}$13.0 Hz, 1C), 134.3 (dd, $J_{CF}$=2.9, 5.9 Hz, 1C), 134.2, 133.5, 124.6 (dd, $J_{CF}$=3.4, 6.6 Hz, 1C), 117.8 (dd, $J_{CF}$=17.8, 191.8 Hz, 1C). $^{19}$F NMR (376 MHz, DMSO-$d_6$) δ ppm −137.65, −137.71. HRMS (m/z): $[M+H]^+$, calcd for $C_{15}H_{10}F_2N_3O_2$, 302.0736; found, 302.0728.

2-(3,4-Dichlorophenyl)-N-(oxazol-2-yl)pyrimidine-4-carboxamide (83). This compound was prepared by the general procedures A, C and D affording 83 as a colorless powder (209 mg, 42%). $^1$H NMR (400 MHz, DMSO-$d_6$) δ ppm 11.98 (s, 1H), 9.23 (d, J=5.1 Hz, 1H), 9.00 (s, 1H), 8.65 (d, J=8.8 Hz, 1H), 8.09 (s, 1H), 8.06 (dd, J=1.1, 5.0 Hz, 1H), 7.85 (dd, J=1.2, 8.3 Hz, 1H), 7.30 (s, 1H). $^{13}$C NMR (101 MHz, DMSO-$d_6$) δ ppm 161.5, 160.6, 160.1, 155.4, 151.7, 137.3, 136.2, 133.7, 131.3, 130.4, 129.7, 127.9, 126.7, 117.2. HRMS (m/z): $[M+H]^+$, calcd for $C_{14}H_9Cl_2N_4O_2$, 335.0097; found, 335.0089.

2-(3-Chlorophenyl)-N-(oxazol-2-yl)pyrimidine-4-carboxamide (84). This compound was prepared by the general procedures A, C, and D affording 84 as a colorless powder (175 mg, 39%). $^1$H NMR (400 MHz, DMSO-$d_6$) δ ppm 11.96 (s, 1H), 9.23 (d, J=4.4 Hz, 1H), 8.81 (br s, 1H), 8.64 (d, J=7.6 Hz, 1H), 8.12 (s, 1H), 8.07 (d, J=4.9 Hz, 1H), 7.52-7.70 (m, 2H), 7.33 (s, 1H). $^{13}$C NMR (101 MHz, DMSO-$d_6$) δ ppm 162.6, 162.4, 161.0, 156.4, 152.8, 138.7, 138.3, 134.3, 131.7, 131.0, 128.7, 127.8, 127.5, 118.1. HRMS (m/z): $[M+H]^+$, calcd for $C_{14}H_{10}ClN_4O_2$, 301.0487; found, 301.0494.

N-(Oxazol-2-yl)-2-(3-(trifluoromethyl)phenyl)pyrimidine-4-carboxamide (85). This compound was prepared by the general procedures A, C, and D affording 85 as a colorless powder (168 mg, 38%). $^1$H NMR (400 MHz, DMSO-$d_6$) δ ppm 12.02 (br s, 1H), 9.27 (d, J=4.9 Hz, 1H), 9.04 (d, J=8.3 Hz, 1H), 8.98 (s, 1H), 8.07-8.15 (m, 2H), 7.93-8.01 (m, 1H), 7.77-7.88 (m, 1H), 7.33 (d, J=1.0 Hz, 1H). $^{13}$C NMR (101 MHz, DMSO-$d_6$) δ ppm 162.3, 161.1, 156.6, 152.8, 138.2, 137.7, 133.0, 130.3, 130.1 (q, $J_{CF}$=32.1 Hz, 1C), 128.3 (q, $J_{CF}$=3.6 Hz, 1C), 127.7, 125.4 (q, $J_{CF}$=3.8 Hz, 1C), 124.7 (q, $J_{CF}$=272.0 Hz, 1C), 118.3. $^{19}$F NMR (376 MHz, DMSO-$d_6$) δ ppm −60.97. HRMS (m/z): $[M+H]^+$, calcd for $C_{15}H_{10}F_3N_4O_2$, 335.0750; found, 335.0763.

6-(3,4-Dichlorophenyl)-N-(oxazol-2-yl)pyrazine-2-carboxamide (86). This compound was prepared by the general procedures A, C, and D affording 86 as a colorless powder (168 mg, 33%). $^1$H NMR (400 MHz, DMSO-$d_6$) δ ppm 11.90 (br s, 1H), 9.62 (s, 1H), 9.24 (s, 1H), 8.77-8.91 (m, 1H), 8.47 (dd, J=2.2, 8.6 Hz, 1H), 8.09 (d, J=1.0 Hz, 1H), 7.83 (d, J=8.6 Hz, 1H), 7.30 (d, J=1.0 Hz, 1H). $^{13}$C NMR (101 MHz, DMSO-$d_6$) δ ppm 162.7, 152.9, 148.1, 145.8, 143.6, 143.2, 138.1, 135.7, 133.9, 132.6, 131.5, 129.9, 128.0, 127.7. HRMS (m/z): $[M+H]^+$, calcd for $C_{14}H_9Cl_2N_4O_2$, 335.0097; found, 335.0112.

Scheme 10. Synthetic route for accessing compound 87

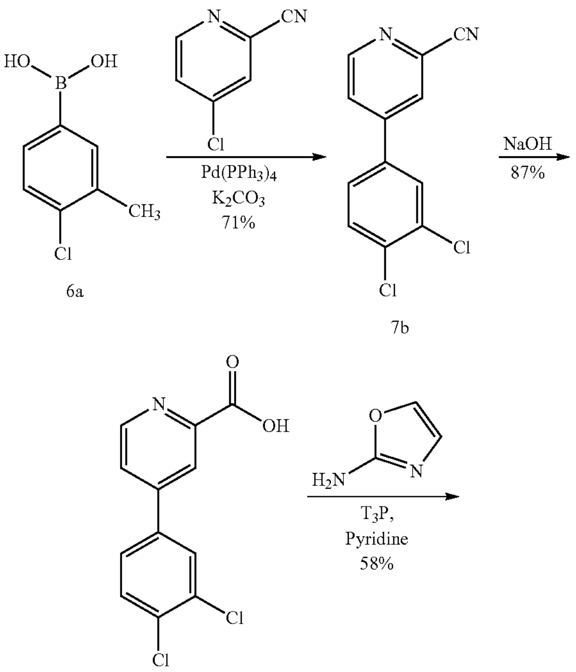

6a 7b 8c

-continued

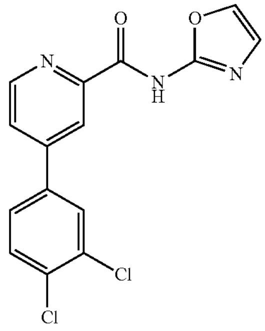

87

(3,4-Dichlorophenyl)picolinonitrile (7b). This compound was prepared by the general procedure A, affording 7b as a white powder in 71% yield (3.80 g). $^1$H NMR (400 MHz, DMSO-$d_6$) δ ppm 8.83 (dd, J=0.6, 5.3 Hz, 1H), 8.52 (dd, J=0.7, 2.0 Hz, 1H), 8.26 (d, J=2.5 Hz, 1H), 8.15 (dd, J=1.9, 5.4 Hz, 1H), 7.93 (dd, J=2.2, 8.6 Hz, 1H), 7.83 (d, J=8.6 Hz, 1H). $^{13}$C NMR (101 MHz, DMSO-$d_6$) δ ppm 152.3, 146.6, 136.2, 134.0, 133.6, 132.8, 131.9, 129.7, 127.9, 127.1, 125.5, 118.0. HRMS (m/z): $[M-H]^-$, calcd for $C_{12}H_5Cl_2N_2$, 246.9835; found, 246.9842.

4-(3,4-Dichlorophenyl)picolinic acid (8c). This compound was prepared by the general procedure C, affording 8c as a white powder in 87% yield (1.40 g). $^1$H NMR (400 MHz, DMSO-$d_6$) δ ppm 8.77 (dd, J=0.6, 5.0 Hz, 1H), 8.32 (dd, J=0.7, 2.0 Hz, 1H), 8.16 (d, J=2.2 Hz, 1H), 8.01 (dd, J=1.8, 5.0 Hz, 1H), 7.86 (dd, J=2.2, 8.3 Hz, 1H), 7.78 (d, J=8.3 Hz, 1H). $^{13}$C NMR (101 MHz, DMSO-$d_6$) δ ppm 166.5, 150.6, 149.7, 146.5, 137.5, 133.0, 132.7, 131.8, 129.5, 127.8, 124.9, 122.5. HRMS (m/z): $[M-H]^-$, calcd for $C_{12}H_6Cl_2NO_2$, 265.9781; found, 265.9793.

4-(3,4-Dichlorophenyl)-N-(oxazol-2-yl)picolinamide (87). This compound was prepared by the general procedure D, affording 87 as a colorless powder in 58% yield (293 mg). $^1$H NMR (400 MHz, DMSO-$d_6$) δ ppm 11.52 (s, 1H), 8.79 (d, J=5.1 Hz, 1H), 8.37 (d, J=2.0 Hz, 1H), 8.18 (d, J=2.2 Hz, 1H), 8.06 (dd, J=2.0, 5.1 Hz, 1H), 7.95-8.04 (m, 1H), 7.88 (dd, J=2.2, 8.6 Hz, 1H), 7.78 (d, J=8.3 Hz, 1H), 7.22 (d, J=1.0 Hz, 1H). $^{13}$C NMR (101 MHz, DMSO-$d_6$) δ ppm 163.2, 153.0, 150.0, 149.9, 146.9, 137.8, 137.4, 133.1, 132.7, 131.8, 129.6, 127.9, 127.7, 125.4, 120.7. HRMS (m/z): $[M+H]^+$, calcd for $C_{15}H_{10}Cl_2N_3O_2$, 334.0145; found, 334.0156.

4-(4-Chlorophenyl)-N-(oxazol-2-yl)picolinamide (88). This compound was prepared by the general procedures A, C and D affording 88 as a colorless powder (222 mg, 49%). $^1$H NMR (400 MHz, DMSO-$d_6$) δ ppm 11.50 (br s, 1H), 8.79 (d, J=5.1 Hz, 1H), 8.37 (s, 1H), 8.02 (d, J=3.2 Hz, 1H), 7.89-7.99 (m, 2H), 7.59-7.67 (m, 2H), 7.18 (s, 1H). $^{13}$C NMR (101 MHz, DMSO-$d_6$) δ ppm 162.8, 150.1, 150.0, 136.6, 129.8, 129.7, 129.3, 129.0, 127.3, 124.4, 120.6. HRMS (m/z): $[M+H]^+$, calcd for $C_{15}H_{11}ClN_3O_2$, 300.0534; found, 300.0545.

4-(4-Fluorophenyl)-N-(oxazol-2-yl)picolinamide (89). This compound was prepared by the general procedures A, C and D affording 89 as a light yellow-colored powder (133 mg, 31%). $^1$H NMR (400 MHz, DMSO-$d_6$) δ ppm 11.51 (s, 1H), 8.77 (d, J=5.4 Hz, 1H), 8.30-8.38 (m, 1H), 7.99-8.05 (m, 2H), 7.91-7.99 (m, 2H), 7.33-7.43 (m, 2H), 7.22 (d, J=1.0 Hz, 1H). $^{13}$C NMR (101 MHz, DMSO-$d_6$) δ ppm 163.7 (d, $J_{CF}$=247.6 Hz, 1C), 163.3, 153.0, 150.0, 149.8, 148.4, 137.8, 133.2 (d, $J_{CF}$=3.1 Hz, 1C), 129.9 (d, $J_{CF}$=8.7 Hz, 2C), 127.7, 125.2, 120.4, 116.8 (d, $J_{CF}$=21.6 Hz, 2C). $^{19}$F NMR (376 MHz, DMSO-$d_6$) δ ppm −111.81. HRMS (m/z): $[M+H]^+$, calcd for $C_{15}H_{11}FN_3O_2$, 284.0830; found, 284.0824.

4-(3,4-Difluorophenyl)-N-(oxazol-2-yl)picolinamide (90). This compound was prepared by the general procedures A, C, and D affording 90 as a colorless powder (165 mg, 37%). $^1$H NMR (400 MHz, DMSO-$d_6$) δ ppm 11.54 (s, 1H), 8.65-8.88 (m, 1H), 8.38 (dd, J=0.6, 1.8 Hz, 1H), 8.01-8.13 (m, 3H), 7.76-7.84 (m, 1H), 7.62 (td, J=8.6, 10.5 Hz, 1H), 7.25 (d, J=1.2 Hz, 1H). $^{13}$C NMR (101 MHz, DMSO-$d_6$) δ ppm 163.2, 153.0, 150.9 (dd, $J_{CF}$=252.5, 15.6 Hz, 1C), 150.4 (dd, $J_{CF}$=255.2, 21.8 Hz, 1C), 150.0, 149.9, 147.3, 137.8, 134.3 (dd, $J_{CF}$=6.2, 3.7 Hz, 1C), 127.6, 125.3, 124.8 (dd, $J_{CF}$=6.8, 3.4 Hz, 1C), 120.5, 118.8 (d, $J_{CF}$=17.2 Hz, 1C), 117.0 (d, $J_{CF}$=18.2 Hz, 1C). $^{19}$F NMR (376 MHz, DMSO-$d_6$) δ ppm −137.05, −137.11, −137.33, −137.39. HRMS (m/z): [M+H]V, calcd for $C_{15}H_{10}F_2N_3O_2$, 302.0736; found, 302.0730.

4-(3-Chloro-4-fluorophenyl)-N-(oxazol-2-yl)picolinamide (91). This compound was prepared by the general procedures A, C, and D affording 91 as a colorless powder (63 mg, 13%). $^1$H NMR (400 MHz, DMSO-$d_6$) δ ppm 11.51 (s, 1H), 8.80 (d, J=5.4 Hz, 1H), 8.39 (d, J=2.2 Hz, 1H), 8.21 (dd, J=2.5, 7.09 Hz, 1H), 8.08 (dd, J=2.0, 5.1 Hz, 1H), 8.01 (s, 1H), 7.90-7.99 (m, 1H), 7.61 (t, J=8.9 Hz, 1H), 7.22 (s, 1H). $^{13}$C NMR (101 MHz, DMSO-$d_6$) δ ppm 163.3, 158.6 (d, $J_{CF}$=249.9 Hz, 1C), 153.0, 150.0, 149.9, 147.2, 137.8, 134.7 (d, $J_{CF}$=3.7 Hz, 1C), 130.0, 128.6 (d, $J_{CF}$=7.8 Hz, 1C), 127.7, 125.4, 121.1 (d, $J_{CF}$=17.9 Hz, 1C), 120.7, 118.2 (d, $J_{CF}$=21.2 Hz, 1C). $^{19}$F NMR (376 MHz, DMSO-$d_6$) δ ppm −115.06. HRMS (m/z): $[M+H]^+$, calcd for $C_{15}H_{10}ClFN_3O_2$, 318.0440; found, 318.0438.

4-(4-Chloro-3-fluorophenyl)-N-(oxazol-2-yl)picolinamide (92). This compound was prepared by the general procedures A, C, and D affording 92 as a colorless powder (38 mg, 8%). $^1$H NMR (400 MHz, DMSO-$d_6$) δ ppm 11.52 (s, 1H), 8.82 (d, J=5.1 Hz, 1H), 8.36-8.46 (m, 1H), 8.03-8.12 (m, 2H), 8.01 (s, 1H), 7.73-7.87 (m, 2H), 7.22 (s, 1H). $^{13}$C NMR (101 MHz, DMSO-$d_6$) δ ppm 162.2, 157.1 (d, $J_{CF}$=246.9 Hz, 1C), 151.9, 149.0, 148.9, 146.1 (d, $J_{CF}$=1.7 Hz, 1C), 136.84 (d, $J_{CF}$=7.4 Hz, 1C), 136.77, 130.9, 126.6, 124.3, 123.9 (d, $J_{CF}$=3.5 Hz, 1C), 120.5 (d, $J_{CF}$=17.6 Hz, 1C), 119.5, 115.1 (d, $J_{CF}$=22.4 Hz, 1C). $^{19}$F NMR (376 MHz, DMSO-$d_6$) δ ppm −115.10. HRMS (m/z): $[M+H]^+$, calcd for $C_{15}H_{10}ClFN_3O_2$, 318.0440; found, 318.0453.

4-(3-Fluorophenyl)-N-(oxazol-2-yl)picolinamide (93). This compound was prepared by the general procedures A, C, and D affording 93 as a colorless powder (35 mg, 8%). $^1$H NMR (400 MHz, DMSO-$d_6$) δ ppm 11.51 (s, 1H), 8.82 (d, J=5.1 Hz, 1H), 8.33-8.44 (m, 1H), 8.08 (dd, J=2.0, 5.1 Hz, 1H), 8.01 (s, 1H), 7.71-7.85 (m, 2H), 7.62 (dt, J=6.1, 8.1 Hz, 1H), 7.38 (dt, J=2.7, 8.6 Hz, 1H), 7.22 (s, 1H). $^{13}$C NMR (101 MHz, DMSO-$d_6$) δ ppm 162.3, 162.2 (d, $J_{CF}$=244.3 Hz, 1C), 151.9, 149.0, 148.9, 147.1 (d, $J_{CF}$=2.2 Hz, 1C), 138.2 (d, $J_{CF}$=8.0 Hz, 1C), 136.8, 130.8 (d, $J_{CF}$=8.4 Hz, 1C), 126.6, 124.4, 122.7 (d, $J_{CF}$=2.7 Hz, 1C), 119.6, 116.0 (d, $J_{CF}$=21.1 Hz, 1C), 113.5 (d, $J_{CF}$22.8 Hz, 1C). $^{19}$F NMR (376 MHz, DMSO-$d_6$) δ ppm −112.08. HRMS (m/z): $[M+H]^+$, calcd for $C_{15}H_{11}FN_3O_2$, 284.0830; found, 284.0833.

4-(3,5-Difluorophenyl)-N-(oxazol-2-yl)picolinamide (94). This compound was prepared by the general procedures A, C, and D affording 94 as a colorless powder (132 mg, 29%). $^1$H NMR (400 MHz, DMSO-$d_6$) δ ppm 11.52 (s, 1H), 8.83 (d, J=5.1 Hz, 1H), 8.41 (s, 1H), 8.05-8.20 (m, 1H), 8.01 (s, 1H), 7.73 (d, J=7.6 Hz, 2H), 7.43 (t, J=9.2 Hz, 1H), 7.22 (s, 1H). $^{13}$C NMR (101 MHz, DMSO-$d_6$) δ ppm 162.4 (dd, $J_{CF}$=246.6, 13.5 Hz, 2C), 162.2, 151.9, 149.02, 148.98, 146.0, 139.4 (t, $J_{CF}$9.9 Hz, 1C), 136.8, 126.6, 124.5, 119.8, 110.1 (dd, $J_{CF}$=19.1, 7.6 Hz, 2C), 104.5 (t, $J_{CF}$=25.9 Hz, 1C). $^{19}$F NMR (376 MHz, DMSO-$d_6$) δ ppm −108.59. HRMS (m/z): $[M+H]^+$, calcd for $C_{15}H_{10}F_2N_3O_2$, 302.0736; found, 302.0740.

N-(Oxazol-2-yl)-4-(4-(trifluoromethoxy)phenyl)picolinamide (95). This compound was prepared by the general procedures A, C and D affording 95 as a colorless powder (101 mg, 19%). $^1$H NMR (400 MHz, DMSO-$d_6$) δ ppm 11.51 (s, 1H), 8.82 (d, J=5.1 Hz, 1H), 8.30-8.50 (m, 1H), 7.87-8.13 (m, 4H), 7.56 (d, J=8.8 Hz, 2H), 7.22 (s, 1H). $^{13}$C NMR (101 MHz, DMSO-$d_6$) δ ppm 162.3, 151.9, 149.0, 148.8, 147.0, 136.8, 135.0, 128.8, 126.6, 124.3, 121.1, 119.54, 119.45 (q, $J_{CF}$=256.9 Hz, 1C). $^{19}$F NMR (376 MHz, DMSO-$d_6$) δ ppm −56.69. HRMS (m/z): $[M+H]^+$, calcd for $C_{16}H_{11}F_3N_3O_3$, 350.0747; found, 350.0755.

N-(Oxazol-2-yl)-4-(3-(trifluoromethoxy)phenyl)picolinamide (96). This compound was prepared by the general procedures A, C and D affording 96 as an off-white-colored powder (149 mg, 28%). $^1$H NMR (400 MHz, DMSO-$d_6$) δ ppm 11.54 (s, 1H), 8.83 (d, J=5.1 Hz, 1H), 8.40 (d, J=1.2 Hz, 1H), 8.10 (dd, J=2.0, 5.1 Hz, 1H), 8.00-8.05 (m, 1H), 7.90-8.00 (m, 2H), 7.72 (t, J=8.0 Hz, 1H), 7.50-7.60 (m, 1H), 7.23 (d, J=1.0 Hz, 1H). $^{13}$C NMR (101 MHz, DMSO-$d_6$) δ ppm 162.2, 151.9, 149.0, 148.9, 148.5, 146.7, 138.2, 136.8, 130.8, 126.6, 125.8, 124.5, 121.6, 119.7, 119.5 (d, $J_{CF}$=256.6 Hz, 1C), 119.4. $^{19}$F NMR (376 MHz, DMSO-$d_6$) δ ppm −56.68. HRMS (m/z): $[M+H]^+$, calcd for $C_{16}H_{11}F_3N_3O_3$, 350.0747; found, 350.0745.

N-(Oxazol-2-yl)-4-(4-(trifluoromethyl)phenyl)picolinamide (97). This compound was prepared by the general procedures A, C, and D affording 97 as a white powder (126 mg, 25%). $^1$H NMR (400 MHz, DMSO-$d_6$) δ ppm 11.54 (s, 1H), 8.86 (d, J=5.1 Hz, 1H), 8.42 (s, 1H), 8.07-8.19 (m, 3H), 8.01 (s, 1H), 7.93 (d, J=8.6 Hz, 2H), 7.23 (s, 1H). $^{13}$C NMR (101 MHz, DMSO-$d_6$) δ ppm 162.2, 151.9, 149.1, 148.9, 146.9, 139.8, 136.8, 129.3 (q, $J_{CF}$=32.1 Hz, 1C), 127.6, 126.6, 125.6 (q, $J_{CF}$=3.7 Hz, 2C), 124.6, 123.5 (q, $J_{CF}$=272.2 Hz, 1C), 119.8. $^{19}$F NMR (376 MHz, DMSO-$d_6$) δ ppm −61.20. HRMS (m/z): $[M+H]^+$, calcd for $C_{16}H_{11}F_3N_3O_2$, 334.0798; found, 334.0797.

N-(Oxazol-2-yl)-4-(3-(trifluoromethyl)phenyl)picolinamide (98). This compound was prepared by the general procedures A, C, and D affording 98 as a colorless powder (119 mg, 24%). $^1$H NMR (400 MHz, DMSO-$d_6$) δ ppm 11.58 (s, 1H), 8.85 (d, J=4.9 Hz, 1H), 8.45 (dd, J=0.5, 1.7 Hz, 1H), 8.18-8.27 (m, 2H), 8.15 (dd, J=2.0, 5.1 Hz, 1H), 8.04 (d, J=1.0 Hz, 1H), 7.90 (d, J=7.8 Hz, 1H), 7.81 (t, J=7.7 Hz, 1H), 7.26 (d, J=1.0 Hz, 1H). $^{13}$C NMR (101 MHz, DMSO-$d_6$) δ ppm 163.3, 153.0, 150.0, 149.9, 147.9, 138.0, 137.8, 131.8, 130.9, 130.6 (q, $J_{CF}$=31.9 Hz, 1C), 127.7, 126.8 (q, $J_{CF}$=3.7 Hz, 1C), 125.6, 124.5 (q, $J_{CF}$=272.6 Hz, 1C), 124.3 (q, $J_{CF}$=3.8 Hz, 1C), 120.9. $^{19}$F NMR (376 MHz, DMSO-$d_6$) δ ppm −61.07. HRMS (m/z): $[M+H]^+$, calcd for $C_{16}H_{11}F_3N_3O_2$, 334.0798; found, 334.0792.

2-(3,4-Dichlorophenoxy)-N-(oxazol-2-yl)isonicotinamide (99). This compound was prepared by the general procedures B, C, and D affording 99 as a colorless powder (184 mg, 35%). $^1$H NMR (400 MHz, DMSO-$d_6$) δ ppm 12.05 (br s, 1H), 8.32 (dd, J=0.8, 4.72 Hz, 1H), 7.93 (br s, 1H), 7.60-7.75 (m, 2H), 7.47-7.60 (m, 2H), 7.12-7.31 (m, 2H). $^{13}$C NMR (101 MHz, DMSO-$d_6$) δ ppm 163.6, 153.6, 149.0, 132.4, 131.9, 127.8, 126.6, 124.4, 122.7, 118.6, 111.0. HRMS (m/z): [M+H]V, calcd for $C_{15}H_{10}Cl_2N_3O_3$, 350.0094; found, 350.0110.

2-(3-Chlorophenoxy)-N-(oxazol-2-yl)isonicotinamide (100). This compound was prepared by the general procedures B, C, and D affording 100 as a light pink-colored powder (157 mg, 33%). $^1$H NMR (400 MHz, DMSO-$d_6$) δ ppm 12.07 (br s, 1H), 8.34 (d, J=5.4 Hz, 1H), 7.95 (br s, 1H), 7.62-7.69 (m, 1H), 7.55 (s, 1H), 7.43-7.52 (m, 1H), 7.29-7.36 (m, 2H), 7.26 (s, 1H), 7.18 (td, J=1.5, 8.6 Hz, 1H). $^{13}$C NMR (101 MHz, DMSO-$d_6$) δ ppm 162.6, 153.9, 147.7, 133.0, 130.6, 124.3, 121.0, 119.6, 117.1, 109.6. HRMS (m/z): [M+H]$^+$, calcd for $C_{15}H_{11}ClN_3O_3$, 316.0483; found, 316.0480.

2-(3-Chloro-4-fluorophenoxy)-N-(oxazol-2-yl)isonicotinamide (101). This compound was prepared by the general procedures B, C, and D affording 101 as a light pink-colored powder (119 mg, 24%). $^1$H NMR (400 MHz, DMSO-$d_6$) δ ppm 11.93 (br s, 1H), 8.33 (d, J=5.1 Hz, 1H), 7.96 (br s, 1H), 7.64 (d, J=5.4 Hz, 1H), 7.42-7.59 (m, 3H), 7.14-7.31 (m, 2H). $^{13}$C NMR (101 MHz, DMSO-$d_6$) δ ppm 162.7, 153.9 (d, $J_{CF}$=243.6 Hz, 1C), 149.2, 147.6, 123.2, 121.7 (d, $J_{CF}$=7.4 Hz, 1C), 119.3 (d, $J_{CF}$=19.3 Hz, 1C), 116.9 (d, $J_{CF}$=22.6 Hz, 1C), 109.4. $^{19}$F NMR (376 MHz, DMSO-$d_6$) δ ppm −121.22. HRMS (m/z): [M+H]$^+$, calcd for $C_{15}H_{10}ClFN_3O_3$, 334.0389; found, 334.0381.

2-(4-Chloro-3-fluorophenoxy)-N-(oxazol-2-yl)isonicotinamide (102). This compound was prepared by the general procedures B, C, and D affording 102 as a colorless powder (221 mg, 44%). $^1$H NMR (400 MHz, DMSO-$d_6$) δ ppm 12.12 (br s, 1H), 8.35 (d, J=5.1 Hz, 1H), 7.96 (s, 1H), 7.61-7.77 (m, 2H), 7.53-7.61 (m, 1H), 7.43 (dd, J=2.7, 10.5 Hz, 1H), 7.27 (s, 1H), 7.11 (ddd, J=1.4, 2.6, 8.7 Hz, 1H). $^{13}$C NMR (101 MHz, DMSO-$d_6$) δ ppm 162.4, 156.8 (d, $J_{CF}$=247.3 Hz, 1C), 152.8 (d, $J_{CF}$=10.1 Hz, 1C), 147.7, 130.4, 118.3 (d, $J_{CF}$=3.5 Hz, 1C), 117.3, 114.9 (d, $J_{CF}$=17.6 Hz, 1C), 110.3 (d, $J_{CF}$=23.5 Hz, 1C), 109.6. $^{19}$F NMR (376 MHz, DMSO-$d_6$) δ ppm −113.37. HRMS (m/z): [M−H]$^-$, calcd for $C_{15}H_{10}ClFN_3O_3$, 334.0389; found, 334.0403.

N-(Oxazol-2-yl)-2-(3-(trifluoromethyl)phenoxy)isonicotinamide (103). This compound was prepared by the general procedures B, C, and D affording 103 as a light-pink-colored powder (103 mg, 20%). $^1$H NMR (400 MHz, DMSO-$d_6$) δ ppm 11.98 (br s, 1H), 8.35 (d, J=5.1 Hz, 1H), 7.97 (br s, 1H), 7.66-7.74 (m, 2H), 7.56-7.66 (m, 3H), 7.47-7.56 (m, 1H), 7.28 (br s, 1H). $^{13}$C NMR (101 MHz, DMSO-$d_6$) δ ppm 163.6, 154.4, 148.7, 131.5, 131.0 (q, $J_{CF}$=32.1 Hz, 1C), 126.2, 124.2 (q, $J_{CF}$=272.4 Hz, 1C), 122.0 (q, $J_{CF}$=3.6 Hz, 1C), 118.8 (q, $J_{CF}$=3.8 Hz, 1C), 118.2, 110.8. $^{19}$F NMR (376 MHz, DMSO-$d_6$) δ ppm −61.07. HRMS (m/z): [M+H]$^+$, calcd for $C_{16}H_{11}F_3N_3O_3$, 350.0747; found, 350.0762.

N-(Oxazol-2-yl)-2-(4-(trifluoromethoxy)phenoxy)isonicotinamide (104). This compound was prepared by the general procedures B, C, and D affording 104 as a colorless powder (163 mg, 30%). $^1$H NMR (400 MHz, DMSO-$d_6$) δ ppm 12.03 (br s, 1H), 8.34 (d, J=5.1 Hz, 1H), 7.97 (br s, 1H), 7.67 (d, J=5.9 Hz, 1H), 7.59 (s, 1H), 7.40-7.51 (m, 2H), 7.30-7.39 (m, 2H), 7.27 (br s, 1H). $^{13}$C NMR (101 MHz, DMSO-$d_6$) δ ppm 166.0, 164.0, 163.8, 152.8, 148.9, 148.7, 145.3, 144.1, 123.5, 123.1, 120.6 (q, $J_{CF}$=256.0 Hz, 1C), 118.0, 110.6. $^{19}$F NMR (376 MHz, DMSO-$d_6$) δ ppm −57.14. HRMS (m/z): [M+H]$^+$, calcd for $C_{16}H_{11}F_3N_3O_4$, 366.0696; found, 366.0702.

N-(Oxazol-2-yl)-2-(3-(trifluoromethoxy)phenoxy)isonicotinamide (105). This compound was prepared by the general procedures B, C, and D affording 105 as a white powder (170 mg, 31%). $^1$H NMR (400 MHz, DMSO-$d_6$) δ ppm (br s, 1H), 8.34 (d, J=5.4 Hz, 1H), 7.95 (br s, 1H), 7.67 (d, J=5.4 Hz, 1H), 7.50-7.62 (m, 2H), 7.18-7.32 (m, 4H). $^{13}$C NMR (101 MHz, DMSO-$d_6$) δ ppm 163.5, 155.1, 149.40, 149.38, 148.7, 131.5, 121.0, 120.5 (q, $J_{CF}$=256.8 Hz, 1C), 118.3, 117.6, 115.0, 110.8. $^{19}$F NMR (376 MHz, DMSO-$d_6$) δ ppm −56.94. HRMS (m/z): [M+H]$^+$, calcd for $C_{16}H_{11}F_3N_3O_4$, 366.0696; found, 366.0691.

4-(3,4-Difluorophenoxy)-N-(oxazol-2-yl)picolinamide (106). This compound was prepared by the general procedures B, C, and D affording 106 as a colorless powder (140 mg, 29%). $^1$H NMR (400 MHz, DMSO-$d_6$) δ ppm 11.47 (s, 1H), 8.64 (d, J=5.6 Hz, 1H), 7.83-8.11 (m, 1H), 7.46-7.70 (m, 3H), 7.29 (dd, J=2.7, 5.6 Hz, 1H), 7.10-7.24 (m, 2H). $^{13}$C NMR (101 MHz, DMSO-$d_6$) δ ppm 164.8, 161.8, 151.8, 150.4, 150.3, 149.3 (dd, $J_{CF}$=248.4, 14.0 Hz, 1C), 148.7 (dd, $J_{CF}$=8.9, 2.8 Hz, 1C), 146.9 (dd, $J_{CF}$=244.0, 12.5 Hz, 1C), 136.8, 126.6, 118.2 (d, $J_{CF}$=18.8 Hz, 1C), 117.4 (dd, $J_{CF}$=6.6, 3.6 Hz, 1C), 114.7, 110.8 (d, $J_{CF}$=19.7 Hz, 1C), 109.8. $^{19}$F NMR (376 MHz, DMSO-$d_6$) δ ppm −134.15, −141.35. HRMS (m/z): [M+H]$^+$, calcd for $C_{15}H_{10}F_2N_3O_3$, 318.0685; found, 318.0684.

4-(3-Fluorophenoxy)-N-(oxazol-2-yl)picolinamide (107). This compound was prepared by the general procedures B, C, and D affording 107 as a colorless powder (172 mg, 38%). $^1$H NMR (400 MHz, DMSO-$d_6$) δ ppm 11.47 (s, 1H), 8.65 (d, J=5.6 Hz, 1H), 7.99 (d, J=1.2 Hz, 1H), 7.48-7.63 (m, 2H), 7.31 (dd, J=2.6, 5.5 Hz, 1H), 7.19-7.29 (m, 3H), 7.09-7.15 (m, 1H). $^{13}$C NMR (101 MHz, DMSO-$d_6$) δ ppm 165.6, 163.4 (d, $J_{CF}$=246.2 Hz, 1C), 162.8, 154.9 (d, $J_{CF}$=11.0 Hz, 1C), 152.8, 151.4, 151.3, 137.9, 132.4 (d, $J_{CF}$=9.7 Hz, 1C), 127.7, 117.5 (d, $J_{CF}$=3.2 Hz, 1C), 116.1, 113.5 (d, $J_{CF}$=21.0 Hz, 1C), 111.0, 109.3 (d, $J_{CF}$=24.3 Hz, 1C). $^{19}$F NMR (376 MHz, DMSO-$d_6$) δ ppm −109.76. HRMS (m/z): [M+H]$^+$, calcd for $C_{15}H_{11}FN_3O_3$, 300.0779; found, 300.0774.

N-(Oxazol-2-yl)-4-(3-(trifluoromethoxy)phenoxy)picolinamide (108). This compound was prepared by the general procedures B, C, and D affording 108 as a colorless powder (148 mg, 27%). $^1$H NMR (400 MHz, DMSO-$d_6$) δ ppm 11.48 (s, 1H), 8.66 (d, J=5.4 Hz, 1H), 7.99 (d, J=1.00 Hz, 1H), 7.67 (t, J=8.2 Hz, 1H), 7.56 (d, J=2.7 Hz, 1H), 7.29-7.43 (m, 4H), 7.21 (d, J=1.2 Hz, 1H). $^{13}$C NMR (101 MHz, DMSO-$d_6$) δ ppm 165.5, 162.8, 154.8, 152.8, 151.5, 151.4, 149.8, 137.9, 132.6, 127.6, 120.5, 120.4 (q, $J_{CF}$=257.1 Hz, 1C), 118.9, 116.1, 114.8. $^{19}$F NMR (376 MHz, DMSO-$d_6$) δ ppm −56.95. HRMS (m/z): [M+H]$^+$, calcd for $C_{16}H_{11}F_3N_3O_4$, 366.0696; found, 366.0701.

N-(Oxazol-2-yl)-4-(4-(trifluoromethoxy)phenoxy)picolinamide (109). This compound was prepared by the general procedures B, C, and D affording 109 as a colorless powder (131 mg, 24%). $^1$H NMR (400 MHz, DMSO-$d_6$) δ ppm 11.47 (s, 1H), 8.65 (d, J=5.6 Hz, 1H), 7.99 (d, J=1.00 Hz, 1H), 7.49-7.60 (m, 3H), 7.36-7.47 (m, 2H), 7.30 (dd, J=2.7, 5.6 Hz, 1H), 7.20 (d, J=1.00 Hz, 1H). $^{13}$C NMR (101 MHz, DMSO-$d_6$) δ ppm 164.7, 161.8, 151.8, 151.5, 150.4, 150.3, 145.1, 136.8, 126.6, 122.9, 122.3, 119.5 (q, $J_{CF}$=256.4 Hz, 1C), 114.9, 109.9. $^{19}$F NMR (376 MHz, DMSO-$d_6$) δ ppm-56.09. HRMS (m/z): [M+H]$^+$, calcd for $C_{16}H_{11}F_3N_3O_4$, 366.0696; found, 366.0683.

N-(Oxazol-2-yl)-4-(4-((trifluoromethyl)thio)phenoxy)picolinamide (110). This compound was prepared by the general procedures B, C, and D affording 110 as a colorless powder (281 mg, 49%). $^1$H NMR (400 MHz, DMSO-$d_6$) δ ppm 11.49 (s, 1H), 8.68 (d, J=5.6 Hz, 1H), 7.99 (d, J=0.7 Hz, 1H), 7.80-7.93 (m, 2H), 7.59 (d, J=2.7 Hz, 1H), 7.40-7.47 (m, 2H), 7.37 (dd, J=2.6, 5.5 Hz, 1H), 7.20 (d, J=1.0 Hz, 1H). $^{13}$C NMR (101 MHz, DMSO-$d_6$) δ ppm 164.0, 161.7, 155.6, 151.7, 150.5, 150.4, 138.3, 136.8, 129.0 (q, $J_{CF}$=307.9 Hz, 1C), 126.6, 121.4, 119.2 (q, $J_{CF}$=2.1 Hz, 1C), 115.6, 110.5. $^{19}F$ NMR (376 MHz, DMSO-$d_6$) δ ppm −42.37. HRMS (m/z): $[M+H]^+$, calcd for $C_{16}H_{11}F_3N_3O_3S$, 382.0468; found, 382.0465.

4-(4-Methoxyphenoxy)-N-(oxazol-2-yl)picolinamide (111). This compound was prepared by the general procedures B, C, and D affording 111 as a colorless powder (162 mg, 35%). $^1H$ NMR (400 MHz, DMSO-$d_6$) δ ppm 11.44 (s, 1H), 8.58 (d, J=5.6 Hz, 1H), 7.95 (d, J=1.2 Hz, 1H), 7.44 (d, J=2.5 Hz, 1H), 7.14-7.26 (m, 4H), 6.98-7.12 (m, 2H), 3.80 (s, 3H). $^{13}C$ NMR (101 MHz, DMSO-$d_6$) δ ppm 166.8, 163.1, 157.5, 153.3, 151.4, 151.2, 146.8, 137.6, 127.6, 122.7, 116.0, 115.4, 110.1, 56.0. HRMS (m/z): $[M+H]^+$, calcd for $C_{16}H_{14}N_3O_4$, 312.0979; found, 312.0966.

Methyl 2-(4-(3,4-difluorophenoxy)picolinamido)benzo[d]oxazole-5-carboxylate (114). This compound was prepared by the general procedures B, C, and D affording 114 as a white powder (2.08 g, 65%). $^1H$ NMR (400 MHz, DMSO-$d_6$) δ ppm 12.17 (br s, 1H), 8.65 (d, J=5.6 Hz, 1H), 8.15 (d, J=1.5 Hz, 1H), 7.87-8.00 (m, 1H), 7.74 (d, J=8.6 Hz, 1H), 7.52-7.70 (m, 3H), 7.28 (dd, J=2.6, 5.5 Hz, 1H), 7.14-7.24 (m, 1H), 3.89 (s, 3H). $^{13}C$ NMR (101 MHz, DMSO-$d_6$) δ ppm 165.3, 164.8, 161.3, 155.3, 150.4, 150.3, 150.1, 149.4 (dd, $J_{CF}$=241.6, 12.2 Hz, 1C), 148.7 (dd, $J_{CF}$=8.9, 2.7 Hz, 1C), 146.9 (dd, $J_{CF}$=236.7, 13.2 Hz, 1C), 140.4, 125.9, 125.1, 119.0, 118.2 (d, $J_{CF}$=18.8 Hz, 1C), 117.4 (dd, $J_{CF}$=6.4, 3.6 Hz, 1C), 114.9, 110.8 (d, $J_{CF}$=19.8 Hz, 1C), 110.2, 110.0, 51.8. $^{19}F$ NMR (376 MHz, DMSO-$d_6$) δ ppm −134.09 (d, J=22.7 Hz, 1F), −141.33 (d, J=22.8 Hz, 1F). HRMS (m/z): $[M+H]^+$, calcd for $C_{21}H_{14}F_2N_3O_5$, 426.0896; found, 426.0902.

2-(4-(3,4-Difluorophenoxy)picolinamido)benzo[d]oxazole-5-carboxylic acid (115). This compound was prepared starting from 114, following the general procedure E affording 115 as an off-white-colored powder (780 mg, 81%). $^1H$ NMR (400 MHz, DMSO-$d_6$) δ ppm 13.10 (br s, 1H), 12.14 (br s, 1H), 8.68 (d, J=5.6 Hz, 1H), 8.16 (d, J=2.0 Hz, 1H), 7.96 (dd, J=1.7, 8.3 Hz, 1H), 7.78 (d, J=8.6 Hz, 1H), 7.54-7.70 (m, 3H), 7.32 (dd, J=2.5, 5.6 Hz, 1H), 7.13-7.26 (m, 1H). $^{13}C$ NMR (101 MHz, DMSO-$d_6$) δ ppm $^{13}C$ NMR (101 MHz, DMSO) δ 166.4, 164.8, 161.4, 155.1, 150.4, 150.1, 149.3 (dd, $J_{CF}$=248.4, 14.0 Hz, 1C), 148.7 (dd, $J_{CF}$=8.9, 2.8 Hz, 1C), 146.9 (dd, $J_{CF}$=244.0, 12.4 Hz, 1C), 140.1, 127.1, 125.3, 119.1, 118.2 (d, $J_{CF}$=18.8 Hz, 1C), 117.4 (dd, $J_{CF}$=6.6, 3.6 Hz, 1C), 114.9, 110.8 (d, $J_{CF}$=19.7 Hz, 1C), 110.2, 109.7. $^{19}F$ NMR (376 MHz, DMSO-$d_6$) δ ppm −134.08 (d, J=22.8 Hz, 1F), −141.31 (d, J=22.8 Hz, 1F). HRMS (m/z): $[M+H]^+$, calcd for $C_{20}H_{12}F_2N_3O_5$, 412.0740; found, 412.0726.

Sodium 2-(4-(3,4-difluorophenoxy)picolinamido)benzo[d]oxazole-5-carboxylate (116). This compound was prepared starting from 115, following the general procedure F affording 116 as an off-white-colored powder (228 mg, 91%). $^1H$ NMR (400 MHz, DMSO-$d_6$) δ ppm 8.50 (d, J=5.4 Hz, 1H), 8.15 (s, 1H), 7.75 (d, J=2.7 Hz, 1H), 7.66-7.73 (m, 1H), 7.56-7.65 (m, 1H), 7.49-7.56 (m, 1H), 7.11-7.17 (m, 2H), 7.07 (dd, J=2.7, 5.6 Hz, 1H). $^{13}C$ NMR (101 MHz, DMSO-$d_6$) δ ppm 171.6, 167.4, 166.9, 164.1, 156.1, 150.2, 149.30, 149.27 (dd, $J_{CF}$=248.2, 13.9 Hz, 1C), 149.1 (dd, $J_{CF}$=8.8, 2.7 Hz, 1C), 146.7 (dd, $J_{CF}$=243.5, 12.3 Hz, 1C), 142.2, 127.2, 123.3, 118.1 (d, $J_{CF}$=18.8 Hz, 1C), 117.7, 117.3 (dd, $J_{CF}$=6.4, 3.3 Hz, 1C), 113.2, 110.7 (d, $J_{CF}$=19.5 Hz, 1C), 110.2, 107.7. $^{19}F$ NMR (376 MHz, DMSO-$d_6$) δ ppm −136.57 (d, J=20.6 Hz, 1F), −144.06 (d, J=20.6 Hz, 1F). HRMS (m/z): $[M+H]^+$, calcd for $C_{20}H_{11}F_2N_3NaO_5$, 434.0559; found, 434.0561.

Hept-6-yn-1-yl 2-(4-(3,4-difluorophenoxy)picolinamido)benzo[d]oxazole-5-carboxylate (117). Dicyclohexylcarbodiimide (55 mg, 0.3 mmol) was added to a solution of 115 (100 mg, 0.2 mmol) and 4-dimethylaminopyridine (33 mg, 0.3 mmol) in dry DCM (5 mL) in an oven-dried flask, chilled to ice-water temperature, under an $N_2$ atmosphere. After 5 min, 6-heptyn-1-ol (27 mg, 0.2 mmol) was added via a syringe. The solution was stirred and allowed to warm to room temperature overnight. The reaction mixture was concentrated under reduced pressure. EtOAc (10 mL) was added.

The solution was washed with water (2×10 mL) and brine (10 mL). The organic layer was dried ($Na_2SO_4$) and evaporated under reduced pressure. The crude material was purified by silica chromatography using gradient elution from 9:1 hexanes/EtOAc to EtOAc, affording 117 as a colorless powder (81 mg, 67%). $^1H$ NMR (400 MHz, DMSO-$d_6$) δ ppm 12.15 (br s, 1H), 8.67 (d, J=5.6 Hz, 1H), 8.18 (d, J=1.7 Hz, 1H), 7.97 (dd, J=1.7, 8.6 Hz, 1H), 7.80 (d, J=8.3 Hz, 1H), 7.56-7.68 (m, 3H), 7.32 (dd, J=2.7, 5.6 Hz, 1H), 7.14-7.24 (m, 1H), 4.30 (t, J=6.5 Hz, 2H), 2.76 (t, J=2.7 Hz, 1H), 2.15-2.24 (m, 2H), 1.69-1.80 (m, 2H), 1.47-1.56 (m, 4H). $^{13}C$ NMR (101 MHz, DMSO-$d_6$) δ ppm 165.9, 162.4, 156.3, 151.5, 151.4, 151.1, 150.4 (dd, $J_{CF}$=248.3, 14.1 Hz, 1C), 149.7 (dd, $J_{CF}$=8.9, 2.9 Hz, 1C), 148.0 (dd, $J_{CF}$=244.1, 12.4 Hz, 1C), 141.4, 127.2, 126.1, 120.0, 119.3 (d, $J_{CF}$=18.7 Hz, 1C), 118.5 (dd, $J_{CF}$=6.6, 3.4 Hz, 1C), 116.0, 111.9 (d, $J_{CF}$=19.7 Hz, 1C), 111.2, 111.0, 84.9, 71.7, 65.2, 28.1, 28.0, 25.1, 18.1. $^{19}F$ NMR (376 MHz, DMSO-$d_6$) δ ppm −134.08 (d, J=22.7 Hz, 1F), −141.31 (d, J=22.9 Hz, 1F). HRMS (m/z): $[M+H]^+$, calcd for $C_{27}H_{22}F_2N_3O_5$, 506.1522; found, 506.1515.

2-(4-(4-(Trifluoromethoxy)phenyl)picolinamido)benzo[d]oxazole-6-carboxylic acid (118). This compound was prepared by the general procedures A, C, D, and E affording 118 as a colorless powder (180 mg, 73%). $^1H$ NMR (400 MHz, DMSO-$d_6$) δ ppm 13.10 (br s, 1H), 12.18 (br s, 1H), 8.86 (d, J=5.4 Hz, 1H), 8.41-8.46 (m, 1H), 8.18 (d, J=1.7 Hz, 1H), 8.11 (dd, J=2.0, 5.1 Hz, 1H), 8.04-8.09 (m, 2H), 7.97 (dd, J=1.8, 8.4 Hz, 1H), 7.80 (d, J=8.6 Hz, 1H), 7.58 (d, J=8.8 Hz, 2H). $^{13}C$ NMR (101 MHz, DMSO-$d_6$) δ ppm 167.5, 162.8, 156.3, 151.2, 150.1, 149.9, 149.7, 148.1, 141.3, 136.0, 129.8, 128.1, 126.3, 125.7, 122.2, 120.9, 120.5 (q, $J_{CF}$=256.9 Hz, 1C), 120.1, 110.7. $^{19}F$ NMR (376 MHz, DMSO-$d_6$) δ ppm −56.69. HRMS (m/z): $[M+H]^+$, calcd for $C_{21}H_{13}F_3N_3O_5$, 444.0802; found, 444.0791.

2-(4-(3-(Trifluoromethoxy)phenyl)picolinamido)benzo[d]oxazole-6-carboxylic acid (119). This compound was prepared by the general procedures A, C, D, and E affording 119 as a colorless powder (198 mg, 81%). $^1H$ NMR (400 MHz, DMSO-$d_6$) δ ppm 13.11 (br s, 1H), 12.19 (br s, 1H), 8.87 (d, J=5.1 Hz, 1H), 8.46 (s, 1H), 8.18 (d, J=1.7 Hz, 1H), 8.08-8.16 (m, 1H), 7.91-8.04 (m, 3H), 7.80 (d, J=8.6 Hz, 1H), 7.73 (t, J=7.8 Hz, 1H), 7.49-7.62 (m, 1H). $^{13}C$ NMR (101 MHz, DMSO-$d_6$) δ ppm 166.4, 161.8, 155.3, 150.1, 147.1, 148.8, 148.52, 148.51, 146.8, 140.3, 138.1, 130.8, 127.1, 125.9, 125.2, 124.8, 121.6, 120.1, 119.51 (q, $J_{CF}$=256.7 Hz, 1C), 119.46, 119.1, 109.7. $^{19}F$ NMR (376 MHz, DMSO-$d_6$) δ ppm −56.68. HRMS (m/z): $[M+H]^+$, calcd for $C_{21}H_{13}F_3N_3O_5$, 444.0802; found, 444.0790.

Example 4. General Biological Methods for SAR of the Picolinamide Antibacterials Screening for Pan-Assay-Interference Structures (PAINS). Active compounds were checked for pan-assay-interference structures (PAINS) using the PAINS remover.

Antibiotics. VAN and MTZ were purchased from Sigma-Aldrich (St. Louis, MO); FDX was purchased from BOC Sciences (Shirley, NY).

Bacterial Strains. *C. difficile* strains used in the study were obtained from Biodefense and Emerging Infections Research Resources Repository (BEI Resources, Manassas, VA) and from American Type Culture Collection (ATCC, Manassas, VA). Seven resistant clinical isolates of *C. difficile* were obtained from Cleveland VA Medical Center. Gut bacteria strains were obtained from BEI. MRSA strains (NRS70 and NRS119) were obtained from the Network on Antimicrobial Resistance in *Staphylococcus aureus* (NARSA). ATCC 29213 and *E. faecium* NCTC7171 (ATCC 19434) were purchased from ATCC (ATCC; Manassas, VA). All the strains were cultured and stored according to the supplier instructions.

Minimum-inhibitory Concentration Determination. MICs for *C. difficile* strains and other gut bacteria were determined with the broth microdilution method as previously described (J. Antimicrob. Chemother. 2013, 68, 515). ESKAPE panel and MRSA MICs were determined as described in the Clinical & Laboratory Standards Institute guidelines.

TABLE 10

Activity of Picolinamide Analogs against MSSA (ATCC 29213) and *E. faecium* (NCTC 7171).

| | *S. aureus* | *E. faecium* |
|---|---|---|
| 4 | 0.06 | 0.06 |
| 5 | 64 | ≥128 |
| 14 | 0.06 | 0.25 |
| 21 | 16 | 16 |
| 28 | 2 | 8 |
| 32 | 1 | 2 |
| 33 | 0.5 | 1 |
| 35 | 4 | 1 |
| 36 | 4 | 8 |
| 37 | 2 | 4 |
| 39 | 0.25 | 0.50 |
| 40 | 0.50 | 1 |
| 41 | 0.06 | 0.06 |
| 43 | 0.25 | 0.5 |
| 44 | 0.25 | 1 |
| 45 | 0.25 | 1 |
| 46 | 0.50 | 2 |
| 47 | 0.25 | 1 |
| 48 | 0.50 | 1 |
| 64 | 8 | 8 |
| 66 | 0.5 | 1 |
| 70 | 0.25 | 0.50 |
| 87 | ≥128 | ≥128 |
| 89 | ≥128 | ≥128 |
| 90 | ≥128 | ≥128 |
| 91 | ≥128 | ≥128 |
| 92 | ≥128 | ≥128 |
| 93 | ≥128 | ≥128 |
| 94 | ≥128 | ≥128 |
| 97 | ≥128 | ≥128 |
| 98 | ≥128 | ≥128 |
| 99 | 0.12 | 0.50 |
| 100 | 1 | 2 |
| 101 | 1 | 2 |
| 102 | 1 | 2 |
| 103 | 1 | 1 |
| 104 | 1 | 16 |
| 105 | 1 | 16 |
| 106 | 64 | 128 |
| 107 | 64 | 64 |
| 108 | 64 | 64 |
| 109 | ≥128 | ≥128 |
| 110 | ≥128 | ≥128 |
| 112 | 64 | ≥128 |
| 114 | 128 | ≥128 |
| 116 | 128 | 128 |

TABLE 10-continued

Activity of Picolinamide Analogs against MSSA (ATCC 29213) and *E. faecium* (NCTC 7171).

| | *S. aureus* | *E. faecium* |
|---|---|---|
| 117 | 32 | 128 |
| 118 | 8 | 64 |

XTT assay. XTT assays were performed with HeLa cells (ATCC CCL-2) in triplicate, as previously described (Lancet 2008, 371, 1486). $IC_{50}$ values were determined by nonlinear regression using GraphPad Prism 5 (San Diego, CA).

Pharmacokinetics (PK) Studies. Compounds 4, 87, 107, and 108 were dissolved in 10% DMSO, 25% propylene glycol, 15% Tween 80 and 50% water at concentrations of 5 mg/mL or 10 mg/mL. Compound 116 was dissolved in 5% DMSO, 95% water with 96 mg/mL of sodium bicarbonate. Mice (n=2 per time point) were given a single 100 μL oral gavage of the test compound (equivalent to either 10 mg/kg and/or 20 mg/kg), and terminal blood was collected in heparinized syringes by cardiac puncture at 30 min, 1 h, 2 h, 4 h, and 8 h. An average of 250 mg of feces were collected after 8 h from two mice housed in metabolism cages in each group for further analysis. Blood was centrifuged at 1000 g for 2 min at 4° C. to obtain plasma. Plasma and fecal samples were stored at −80° C. until analysis. A 45-μL aliquot of plasma was mixed with 5 μL of 50% acetonitrile/50% water and 100 μL of 20 μM solution of internal standard in acetonitrile. The precipitated protein was centrifuged at 21000 g for 15 min at 4° C. The supernatant was analyzed on a Waters Acquity UPLC (Waters Corporation, Milford, MA) with a triple quadrupole detector. Feces were homogenized in 1500 μL of 50% acetonitrile/50% water and centrifuged at 21000 g for 5 min. A 72-μL aliquot of the fecal supernatant was mixed with 8 μL of 50% acetonitrile/50% water and 40 μL of 50 μM solution of internal standard in 0.5% formic acid/99.5% acetonitrile. Concentrations in plasma and feces were determined from calibration curves in control plasma and feces relative to internal standard. The chromatographic conditions consisted of an Acquity UPLC YMC—Triart C18 2.0 mm×100 mm column eluted with 0.5 mL/min of 30% water/70% acetonitrile for 5 min. Mass spectrometry was performed in positive mode electrospray ionization. The capillary, cone, extractor, and RF lens voltages were 2.8 kV, 40V, 1 V, and 0.1 V, respectively. The desolvation and cone gas (nitrogen) flow rates were 650 L/h and 50 L/h, respectively. The source and desolvation temperatures were 150° C. and 350° C., respectively. The multiple-reaction monitoring transitions used for each compound were: 333.40→223.10 for 4, 333.70→221.60 for 87, 300→188.10 for 107, 365.90→254.10 for 108, 411.70→205.90 for 116, and 294.80→133.50 for the internal standard.

Animals. Female CD-1 mice (7-8 weeks old, 24-31 g body weight, Jackson Laboratories, Bar Harbor, ME) were used for the PK studies (Mice were housed in sterile polycarbonate shoeboxes containing 1 inch of corncob (The Andersons Ind., Maumee, OH) and Alpha-Dri (Shepherd Specialty Papers, Inc., Richland, MI) bedding under 72° F. with a 12 h light/dark cycle. Mice were given a Teklad 2918 irradiated extruded rodent diet (Envigo, Indianapolis, IN) and water ad libitum. All procedures were conducted in accordance with and approved by the University of Notre Dame Institutional Animal Care and Use Committee (IACUC).

Example 5. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

(I)

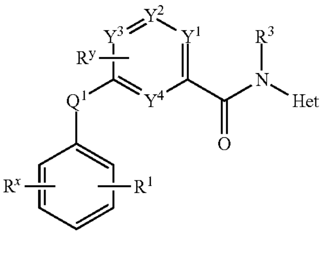

or a salt thereof, wherein

Het is

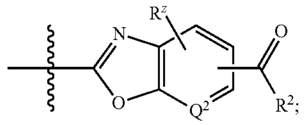

$Q^1$ is O, absent, S, or $NR^w$;

$Q^2$ is CH or N;

each $R^w$ is independently H, —($C_1$-$C_6$) alkyl, or a protecting group;

$R^x$, $R^y$, and $R^z$ are each independently H, halo, OH, CN, $CO_2H$, $NO_2$, —($C_1$-$C_6$) alkyl, —$CO_2$ ($C_1$-$C_6$) alkyl, —O($C_1$-$C_6$) alkyl, or —OC(═O) ($C_1$-$C_6$) alkyl;

$R^1$ is $OR^a$, $SR^a$, halo, CN, $NO_2$, —($C_1$-$C_6$) alkyl, $NR^w$, or heterocyclyl, wherein each $R^a$ is independently $CF_3$, —($C_1$-$C_6$) alkyl, —C(═O) ($C_1$-$C_6$) alkyl, or H;

$R^2$ is OH, —O($C_1$-$C_6$) alkyl, —O($C_3$-$C_6$) cycloalkyl, or —CCH;

$R^3$ is H, —($C_1$-$C_6$) alkyl or —($C_3$-$C_6$) cycloalkyl; and $Y^1$, $Y^2$, $Y^3$, and $Y^4$ are each independently CH or N wherein at least one of $Y^1$ to $Y^4$ is N;

wherein each ($C_1$-$C_6$) alkyl moiety is independently saturated or unsaturated and optionally substituted.

2. The compound of claim 1 wherein $Q^2$ is CH.

3. The compound of claim 1 wherein $R^x$, $R^y$, and $R^z$ are H.

4. The compound of claim 1 wherein $Y^1$ is N, and $Y^2$, $Y^3$, and $Y^4$ are CH.

5. The compound of claim 1 wherein $R^1$ is $OR^a$.

6. The compound of claim 1 wherein the compound is represented by Formula II:

(II)

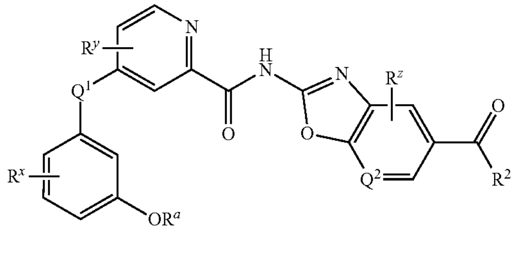

or a salt thereof.

7. The compound of claim 6 wherein $Q^1$ is O.

8. The compound of claim 6 wherein $R^a$ is $CF_3$.

9. The compound of claim 6 wherein $R^2$ is OH.

10. The compound of claim 6 wherein the compound is 2-(4-(3-(trifluoromethoxy) phenoxy) picolinamido)benzo[d] oxazole-5-carboxylic acid (1):

(1)

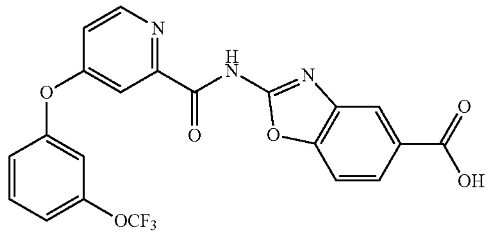

or a salt thereof.

11. A pharmaceutical composition comprising a compound of claim 1 and a pharmaceutically acceptable diluent, carrier, or excipient.

12. The composition of claim 11 wherein the compound is 2-(4-(3-(trifluoromethoxy) phenoxy) picolinamido)benzo [d]oxazole-5-carboxylic acid (1).

13. A method for treating a bacterial infection comprising administering to a subject in need thereof an effective antibacterial amount of a compound of claim 1 wherein the bacterial infection is thereby treated.

14. The method of claim 13 wherein the bacterial infection is a *Clostridioides difficile* (*C. difficile*) infection.

15. The method of claim 14 wherein the compound selectively inhibits the growth or proliferation of *C. difficile*.

16. The method of claim 15 wherein a minimum concentration to inhibit the growth or proliferation of 50% of *C. difficile* ($MIC_{50}$) is about 1 μg/mL or less.

17. The method of claim 15 wherein an effective antibacterial amount of the compound administered as a single dose is about 50 mg/kg or less.

18. The method of claim 13 wherein the compound is 2-(4-(3-(trifluoromethoxy) phenoxy) picolinamido)benzo[d] oxazole-5-carboxylic acid (1).

19. The method of claim 13 wherein the compound inhibits peptidoglycan biosynthesis.

* * * * *